(12) United States Patent
Zhang et al.

(10) Patent No.: US 11,485,752 B2
(45) Date of Patent: Nov. 1, 2022

(54) MODIFIED OLIGONUCLEOTIDES AND COMPOUND THAT CAN BE USED FOR SYNTHESIZING SAME

(71) Applicant: GUANGZHOU RIBOBIO CO., LTD., Guangzhou (CN)

(72) Inventors: Biliang Zhang, Guangdong (CN); Wei Wang, Guangdong (CN)

(73) Assignee: GUANGZHOU RIBOBIO CO., LTD., Guangzhou (CN)

( * ) Notice: Subject to any disclaimer, the term of this patent is extended or adjusted under 35 U.S.C. 154(b) by 0 days.

(21) Appl. No.: 16/756,855

(22) PCT Filed: Dec. 26, 2017

(86) PCT No.: PCT/CN2017/118591
§ 371 (c)(1),
(2) Date: Apr. 17, 2020

(87) PCT Pub. No.: WO2019/127004
PCT Pub. Date: Jul. 4, 2019

(65) Prior Publication Data
US 2020/0369703 A1 Nov. 26, 2020

(51) Int. Cl.
C07H 21/00 (2006.01)
C07H 21/02 (2006.01)
A61K 31/713 (2006.01)
A61K 31/7088 (2006.01)
C07H 15/04 (2006.01)
C12N 15/113 (2010.01)
C07H 15/12 (2006.01)
C07H 15/26 (2006.01)
C07H 15/08 (2006.01)

(52) U.S. Cl.
CPC ......... *C07H 15/04* (2013.01); *A61K 31/7088* (2013.01); *A61K 31/713* (2013.01); *C07H 15/08* (2013.01); *C07H 15/12* (2013.01); *C07H 15/26* (2013.01); *C07H 21/00* (2013.01); *C07H 21/02* (2013.01); *C12N 15/113* (2013.01)

(58) Field of Classification Search
None
See application file for complete search history.

(56) References Cited

U.S. PATENT DOCUMENTS

2015/0119445 A1 4/2015 Manoharan
2015/0126718 A1 5/2015 Prakash et al.

FOREIGN PATENT DOCUMENTS

CN 106471010 A 3/2017
CN 106589042 A 4/2017
(Continued)

OTHER PUBLICATIONS

U.S. Appl. No. 16/753,326, filed Apr. 2020, Zhang et al.*
(Continued)

*Primary Examiner* — Eric Olson
(74) *Attorney, Agent, or Firm* — Gang Yu

(57) ABSTRACT

The present disclosure falls within the field of biomedical technology, and in particular relates to modified oligonucleotides and a compound that can be used for synthesizing same and a method for modifying oligonucleotides. The present disclosure also relates to the use of the modified oligonucleotides for preventing and/or treating diseases associated with the liver in a subject.

3 Claims, 1 Drawing Sheet
Specification includes a Sequence Listing.

(56) References Cited

FOREIGN PATENT DOCUMENTS

| CN | 106795200 A | 5/2017 | |
|---|---|---|---|
| WO | 2013089522 A1 | 6/2013 | |
| WO | WO-2014179629 A2 * | 11/2014 | ........... C12N 15/113 |
| WO | 2016028649 A1 | 2/2016 | |
| WO | 2016055601 A1 | 4/2016 | |
| WO | 2017178656 A1 | 10/2017 | |

OTHER PUBLICATIONS

Dubber Michael et al. "Solid-Phase Synthesis of Multivalent Glycoconjugates on a DNA Synthesizer" Bioconjugate Chemistry, American Chemical Society, vol. 14, No. 1, Jan. 1, 2003 (Jan. 1, 2003), pp. 239-246.

JP examination report dated May 18, 2021 re: Application No. 2020-545836, pp. 1-6.

* cited by examiner

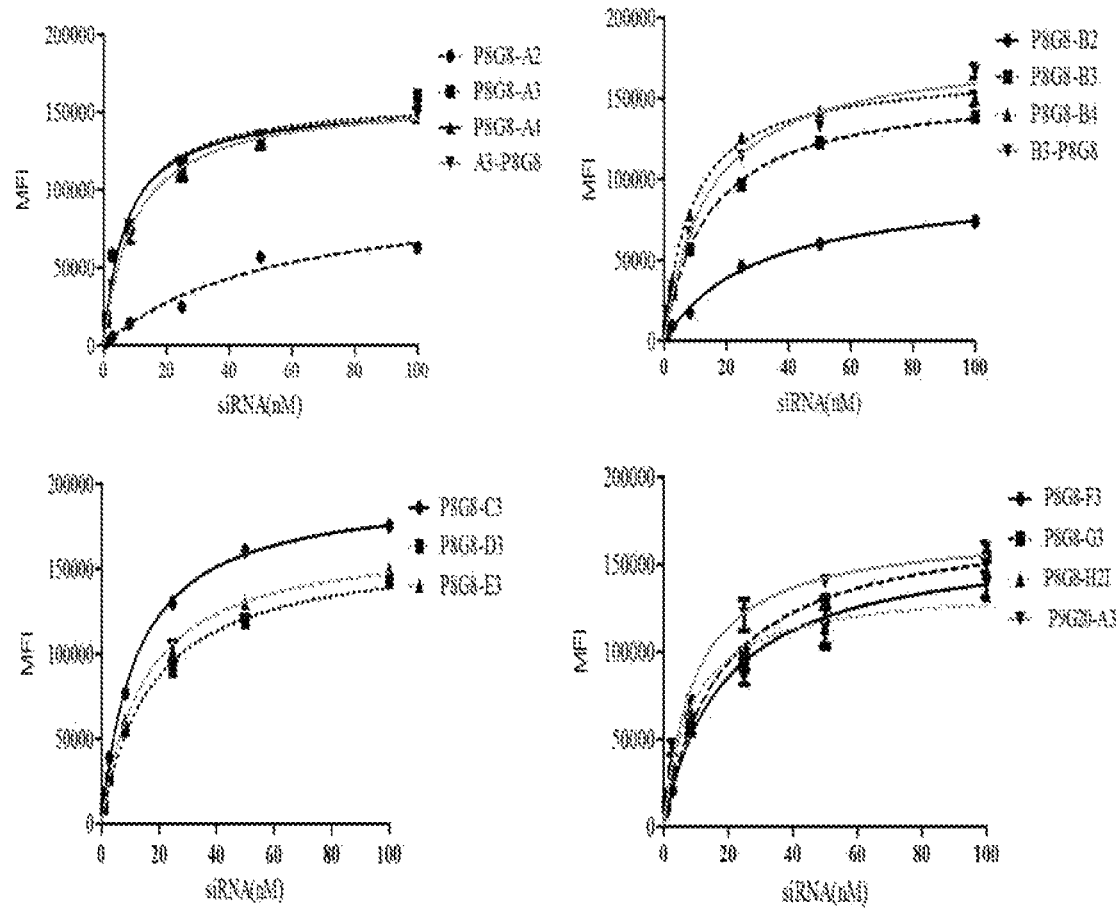

MODIFIED OLIGONUCLEOTIDES AND COMPOUND THAT CAN BE USED FOR SYNTHESIZING SAME

CROSS-REFERENCE TO RELATED PATENT APPLICATIONS

This application is the national stage entry of PCT/CN2017/118591, filed on Dec. 26, 2017, which is incorporated by reference in their entirety herein.

SEQUENCE LISTING

The instant application contains a Sequence Listing which has been submitted electronically in ASCII format and is hereby incorporated by reference in its entirety. Said ASCII copy created 30 Mar. 2020, is named "PN128044_Sequence_Listing.txt" and is 2.8 kilobytes in size, and contains three new sequences disclosed in Table 1 but not numbered (namely SEQ ID NO:5-7) and the four original sequences (SEQ ID NO: 1-4) are identical to the sequence listing filed in the corresponding international application No. PCT/CN2017/118591, so no new matter is added.

TECHNICAL FIELD

The present disclosure belongs to the technical field of biomedicine, and in particular relates to a modified oligonucleotide and a compound that can be used for synthesizing same and a method for modifying the oligonucleotide.

BACKGROUND

Asialoglycoprotein receptor (ASGPR) is an abundant endocytic receptor of hetero-oligomers, which exists mainly on the surface of the cell membrane of liver parenchymal cells facing the side of sinusoidal space and has specificity for sugar. As the terminal sialic acid of the glycoproteins is removed through hydrolysis by enzymes or acidolysis, the exposed penultimates are galactose residues. Therefore, the sugar-binding specificity of ASGPR is actually galactosyl, and it is also called galactose-specific receptor. ASGPRs are mainly distributed in the liver parenchymal cells, and low in content in other cells, so the ASGPRs become the best receptor for liver targeted transport.

Glycoproteins terminated with non-reducing galactose (Gal) or N-acetylgalactosamine (GalNAc) residues can be recognized by ASGPRs, wherein the affinity of GalNAc to ASGPR is about 50 times higher than that of Gal (Iobst S T et al, J Biol Chem, 1996, 271 (12): 6686-6693). In vitro experiments show that the affinity of clustered sugar residues is much higher than that of non-clustered sugar residues by simultaneously occupying the binding sites of the receptor with an affinity order of Tetraantennary>triantennal>>biantennal>>monoantennal galactosides (Lee Y C, et al, J Biol Chem, 1983, 258 (1): 199-202).

ASGPR receptor-mediated liver targeting oligonucleotide is a new breakthrough in the research field of nucleic acid innovative drugs. In 2012, Alnylam Pharmaceuticals Inc. covalently linked triantennary GalNAc structure previously studied with small interfering RNA (siRNA) to achieve liver-targeted delivery of siRNA in vivo. Using this technology, researchers have developed drugs for amyloidosis, hemophilia, hypercholesterolemia, liver porphyrin, hepatitis B and other diseases. A number of drug candidates have entered into clinical studies (http://www.alnylam.com/product-pipeline/). In 2014, ISIS Pharmaceuticals of the United States covalently linked triantennary GalNAc and antisense nucleic acid to achieve liver-targeted drug delivery in animals, with 10-fold increase in antisense nucleic acid activity after linking (Prakash, T. P. et al., Nucleic Acids Res. 42, 8796-807.).

SUMMARY

By intensive research and inventive effort, the present inventors have obtained a compound with an ASGPR ligand that can be used to modify oligonucleotides, thereby obtaining a modified oligonucleotide comprising a conjugate group.

Accordingly, in one aspect, the present application provides a compound comprising an oligonucleotide and a conjugate group, having a general formula

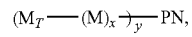

wherein PN is an oligonucleotide, Y is selected from an integer between 1 and 10, X is selected from an integer between 0 and 10, $M_T$ is selected from a conjugate group as shown in formulas (1), (2), (3), and (4), when X is not 0, X M are each independently selected from a conjugate group represented by formulas (1'), (2'), and (3'),

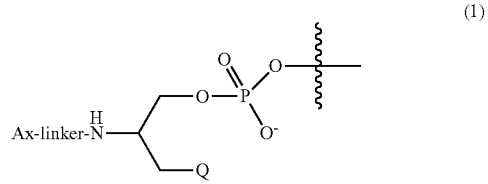

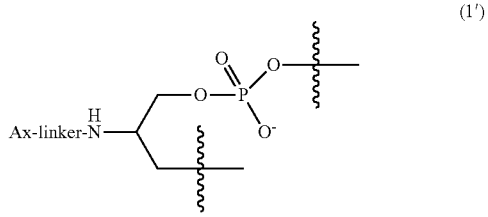

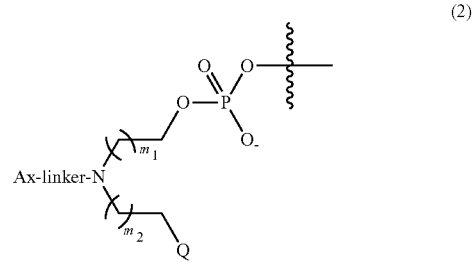

Wherein m1 and m2 are each independently selected from integers 1-10

-continued (2′)
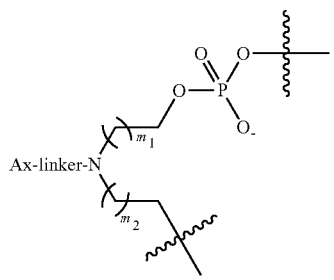

Wherein m1 and m2 are each independently selected from integers 1-10

(3)
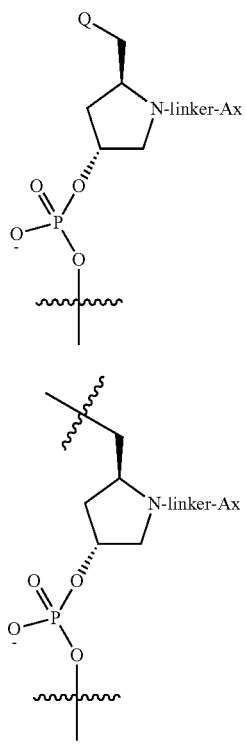

(3′)

(4)
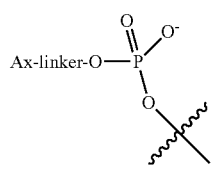

wherein $A_x$ is a ligand, linker is a linker arm, and Q is a hydroxyl group or a modifier.

In certain embodiments, in the conjugate groups represented by formula (1)-(4), and formula (1′)-(3′), $A_x$ is each independently a ligand of a human asialoglycoprotein receptor (ASGPR).

In certain embodiments, in the conjugate groups represented by formulas (1)-(4), and formula (1′)-(3′), $A_x$ is a galactose, an acetylgalactosamine, a galactose-containing polysaccharide, an acetylgalactosamine-containing polysaccharide, a galactose derivative (e.g., an ester of galactose, such as galactoacetate), or an acetylgalactosamine derivative (e.g., an ester of acetylgalactosamine, such as acetylgalactosamine acetate). Optionally, $A_x$ is also each independently provided with a modifying group, such as a carbonylalkyl or an esteralkyl, preferably an alkyl portion of the carbonylalkyl or the esteralkyl is a $C_{1-6}$ alkyl or a $C_{6-12}$ alkyl.

In certain embodiments, $A_x$ is selected from:

$A_1$
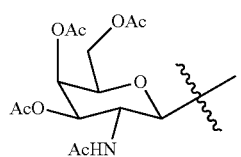

$A_{1′}$
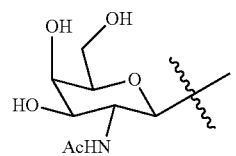

$A_2$
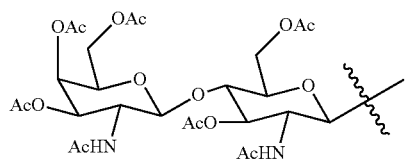

$A_{2′}$
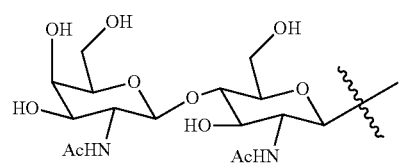

$A_3$
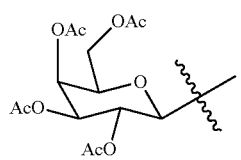

$A_{3′}$
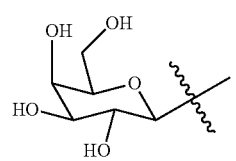

$A_4$
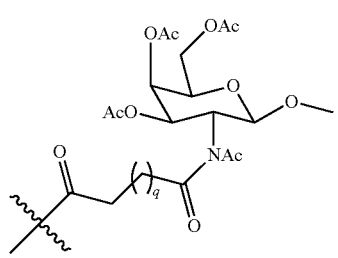

Wherein q is selected from an integer between 1 and 10

-continued

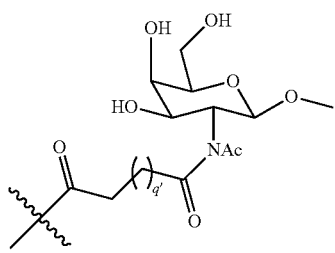

A₄'

Wherein q is selected from an integer between 1 and 10

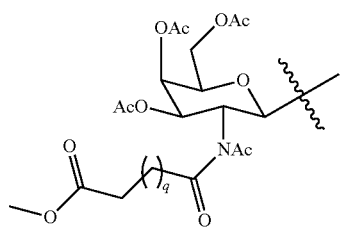

A₅

Wherein q is selected from an integer between 1 and 10

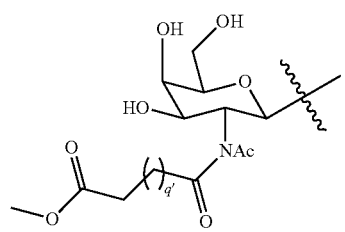

A₅'

Wherein q is selected from an integer between 1 and 10.

In certain embodiments, in the conjugate groups represented by formulas (1)-(4), and formula (1')-(3'), a structure of the linker is each independently as shown in formulas (i), (ii), (iii), (iv), or (v):

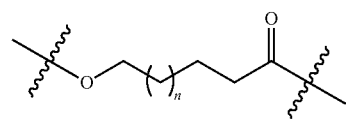
(i)

wherein n is selected from an integer between 1 and 10. In certain embodiments, n is 1 or 6;

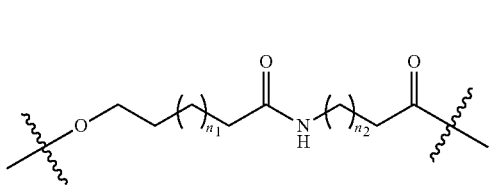
(ii)

wherein $n_1$ and $n_2$ are each independently selected from integers between 1 and 10. In certain embodiments, $n_1$ is 1. In certain embodiments, $n_2$ is 4. In certain embodiments, $n_1$ is 1 and $n_2$ is 4;

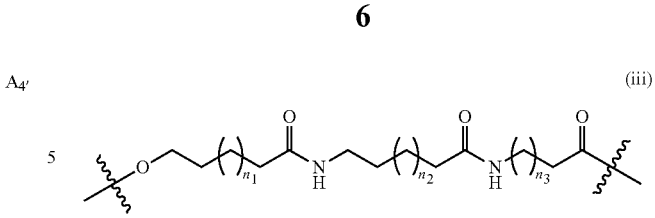
(iii)

wherein $n_1$, $n_2$, and $n_3$ are each independently selected from integers between 1 and 10. In certain embodiments, $n_1$ is 1. In certain embodiments, $n_2$ is 3. In certain embodiments, $n_3$ is 4. In certain embodiments, $n_1$ is 1, $n_2$ is 3, and $n_3$ is 4;

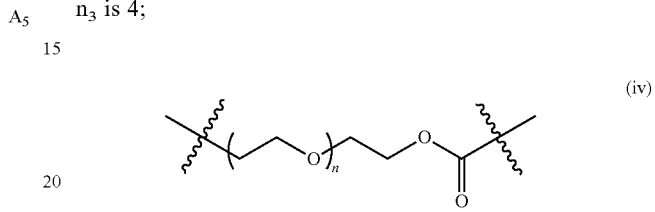
(iv)

wherein n is selected from an integer between 1 and 10. In certain embodiments, n is 1;

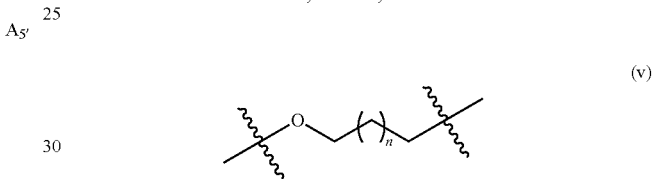
(v)

wherein n is selected from an integer between 1 and 10. In certain embodiments, n is 4.

In certain embodiments, in the conjugate group represented by formula (1) or formula (1'), $A_x$ is each independently selected from $A_1$, $A_2$, $A_3$, $A_1'$, $A_2'$ or $A_3'$, and the structure of the linker is shown in formula (i). In certain embodiments, n is 1 or 6.

In certain embodiments, in the conjugate group represented by formula (1) or formula (1'), $A_x$ is each independently selected from $A_1$ or $A_1'$, and the structure of the linker is shown in formula (ii). In certain embodiments, $n_1$ is 1 and $n_2$ is 4.

In certain embodiments, in the conjugate group represented by formula (1) or formula (1'), $A_x$ is each independently selected from $A_1$, or $A_1'$, and the structure of the linker is shown in formula (iii). In certain embodiments, $n_1$ is 1, $n_2$ is 3, and $n_3$ is 4.

In certain embodiments, in the conjugate group represented by formula (1) or formula (1'), $A_x$ is each independently selected from $A_1$ or $A_1'$, and the structure of the linker is shown in formula (iv). In certain embodiments, n is 1.

In certain embodiments, in the conjugate group represented by formula (2) or (2'), $A_x$ is each independently selected from $A_1$, $A_2$, $A_3$, $A_1'$, $A_2'$ or $A_3'$, and the structure of the linker is shown in formula (i). In certain embodiments, n is 1 or 6.

In certain embodiments, in the conjugate group represented by formula (2) or (2'), $A_x$ is each independently selected from $A_1$ or $A_1'$, and the structure of the linker is shown in formula (ii). In certain embodiments, $n_1$ is 1 and $n_2$ is 4.

In certain embodiments, in the conjugate group represented by formula (3) or (3'), $A_x$ is each independently selected from $A_1, A_2, A_3, A_1', A_2'$ or $A_3'$, and the structure of the linker is shown in formula (i). In certain embodiments, n is 1 or 6.

In certain embodiments, in the conjugate group represented by formula (4), $A_x$ is each independently selected from $A_1$ or $A_1'$, and the structure of the linker is shown in formula (v). In certain embodiments, n is 4.

In certain embodiments, in the conjugate groups represented by formulas (1)-(3), and formula (1')-(3'), Q is selected from: cholesterol and derivatives thereof, polyethylene glycol, fluorescent probes, biotin, polypeptides, vitamins and tissue targeting molecules.

In the present disclosure, the oligonucleotide may be a single-stranded oligonucleotide or a double-stranded oligonucleotide. Optionally, oligonucleotides of the present disclosure may comprise one or more modified nucleotides. In certain embodiments, the one or more modified nucleotides are each independently selected from: 2'-methoxyethyl modified nucleotides, 2'-O-alkyl modified nucleotides (e.g. 2'-O-methyl modified nucleotides), 2'-O-allyl modified nucleotides, 2'-C-allyl modified nucleotides, 2'-fluoro modified nucleotides, 2'-deoxy modified nucleotides, 2'-hydroxy modified nucleotides, locked nucleotides, hexitol nucleic acids (HNAs), and unlocked nucleic acids (UNAs). In certain embodiments, the modified nucleotide is selected from 2'-O-alkyl modified nucleotides, 2'-fluoro modified nucleotides.

In certain embodiments, the oligonucleotide is provided with a terminal modifier, preferably the terminal modifier is selected from: cholesterol, polyethylene glycol, fluorescent probes, biotin, polypeptides, vitamins, tissue targeting molecules and any combination thereof.

In certain embodiments, the phosphate-containing backbone of the oligonucleotide is modified, preferably the modification is a phosphorthioate modification.

In certain embodiments, the oligonucleotide is a siRNA. In certain embodiments, the siRNA comprises a sense strand and an antisense strand complementary to form a double strand. In certain embodiments, the siRNA comprises a sequence as shown in SEQ ID NO: 1, SEQ ID NO: 2, SEQ ID NO: 3, or SEQ ID NO: 4.

In the modified oligonucleotides of the present disclosure, the conjugate groups may be linked at different positions on the oligonucleotide.

In certain embodiments,

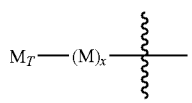

is each independently linked to the 3' terminal, 5' terminal, or sequence middle of any strand of the oligonucleotide. In certain embodiments,

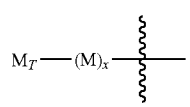

is linked to the oligonucleotide via a phosphotriester. In certain embodiments, the linkage between M and $M_T$ or between M and M is via a phosphotriester.

In certain embodiments, the oligonucleotide is a single-stranded oligonucleotide. In certain embodiments, Y is 1,

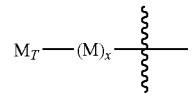

is linked to the 3' terminal or 5' terminal of the oligonucleotide. In certain embodiments, Y is 2, and 2

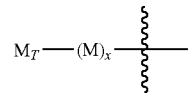

are each linked to the 3' terminal and 5' terminal of the oligonucleotide.

In certain embodiments, the oligonucleotide is a double-stranded oligonucleotide. In certain embodiments, Y is 1,

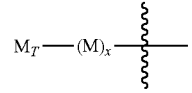

is linked to either the 3' terminal or 5' terminal of any of the strands in the oligonucleotide. In certain embodiments, Y is 2, 2

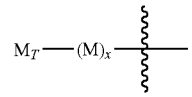

are each linked to the 3' terminal and 5' terminal of the same strand in the oligonucleotide. In certain embodiments, Y is 2, 2

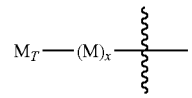

are each linked to the 3' terminals of two strands in the oligonucleotide. In certain embodiments, Y is 2, 2

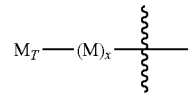

are each linked to the 5' terminals of two strands in the oligonucleotide. In certain embodiments, Y is 3

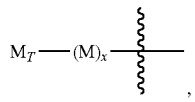

, two of the three are respectively linked with the 3' terminal and 5' terminal of the same strand in the oligonucleotide, and the third is linked with the 3' terminal or 5' terminal of the other strand. In certain embodiments, Y is 4, 4

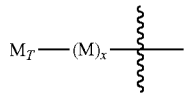

are each linked to the 3' terminals and 5' terminals of two strands in the oligonucleotide.

In the modified oligonucleotide of the present disclosure, the structures between $M_T$ and M or between a plurality of M may have the same or different structures. In certain embodiments, X is not 0, $M_T$ and at least one M has the same $A_x$ and/or linker structure. In certain embodiments, X is greater than 1, and X M have the same or different structures. In certain embodiments, Y is greater than 1 and Y

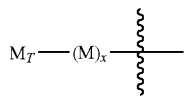

have the same or different structures.

The modified oligonucleotide of the present disclosure may include one or more

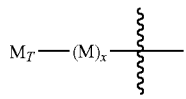

and the structure of M or $M_T$, the number of M, or the number of

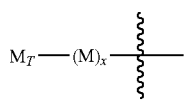

may be adjusted.

In certain embodiments, Y is 1, X is 0, and the compound has one of the following characteristics:

(1) the structure of $M_T$ is shown in formula (1), $A_x$ is $A_1'$, $A_2'$ or $A_3'$, the structure of the linker is shown in formula (i), and preferably, n is 1 or 6;

(2) the structure of $M_T$ is shown in formula (1), $A_x$ is $A_1'$, the structure of the linker is shown in formula (ii), and preferably, $n_1$ is 1 and $n_2$ is 4;

(3) the structure of $M_T$ is shown in formula (1), $A_x$ is $A_1'$, the structure of the linker is shown in formula (iii), and preferably, $n_1$ is 1, $n_2$ is 3 and $n_3$ is 4;

(4) the structure of $M_T$ is shown in formula (1), $A_x$ is $A_1'$, the structure of the linker is shown in formula (iv), and preferably, n is 1;

(5) the structure of $M_T$ is shown in formula (2), $A_x$ is $A_1'$, $A_2'$ or $A_3'$, the structure of the linker is shown in formula (i), and preferably, n is 1 or 6;

(6) the structure of $M_T$ is shown in formula (2), $A_x$ is $A_1'$, the structure of the linker is shown in formula (ii), and preferably, $n_1$ is 1 and $n_2$ is 4;

(7) the structure of $M_T$ is shown in formula (3), $A_x$ is $A_1'$, $A_2'$ or $A_3'$, the structure of the linker is shown in formula (i), and preferably, n is 1 or 6;

(8) the structure of $M_T$ is shown in formula (4), $A_x$ is $A_1'$, the structure of the linker is shown in formula (v), and preferably, n is 1; and (9) the structure of $M_T$ is shown in formula (2), $A_x$ is $A_1'$, the structure of the linker is shown in formula (iii), and preferably, $n_1$ is 1, $n_2$ is 3 and $n_3$ is 4.

In certain embodiments, Y is 1, X is 1, 2, or 3, when X is 2 or 3, each M has the same structure, and the compound has one of the following characteristics:

(1) the structure of M is shown in formula (1'), $A_x$ is $A_1'$, the structure of the linker is shown in formula (i), and preferably, n is 1 or 6; and the structure of $M_T$ is shown in formula (1), $A_x$ is $A_1'$, the structure of the linker is shown in formula (i), and preferably, n is 1 or 6;

(2) the structure of M is shown in formula (1'), $A_x$ is $A_1'$, the structure of the linker is shown in formula (ii), preferably, $n_1$ is 1 and $n_2$ is 4; and the structure of $M_T$ is shown in formula (1), $A_x$ is $A_1'$, the structure of the linker is shown in formula (ii), and preferably, $n_1$ is 1 and $n_2$ is 4;

(3) the structure of M is shown in formula (1'), $A_x$ is $A_1'$, and the structure of the linker is shown in formula (iii), and preferably, $n_1$ is 1, $n_2$ is 3 and $n_3$ is 4; and the structure of $M_T$ is shown in formula (1), $A_x$ is $A_1'$, the structure of the linker is shown in formula (iii), and preferably, $n_1$ is 1, $n_2$ is 3 and $n_3$ is 4;

(4) the structure of M is shown in formula (2'), $A_x$ is $A_1'$, the structure of the linker is shown in formula (i), and preferably, n is 1 or 6; and the structure of $M_T$ is shown in formula (2), $A_x$ is $A_1'$, the structure of the linker is shown in formula (i), and preferably, n is 1 or 6;

(5) the structure of M is shown in formula (1'), $A_x$ is $A_1'$, the structure of the linker is shown in formula (ii), and preferably, $n_1$ is 1 and $n_2$ is 4; and the structure of $M_T$ is shown in formula (1), $A_x$ is $A_1'$, the structure of the linker is shown in formula (ii), and preferably, $n_1$ is 1 and $n_2$ is 4; and (6) the structure of M is shown in formula (1'), $A_x$ is $A_3'$, the structure of the linker is shown in formula (ii), and preferably, $n_1$ is 1 and $n_2$ is 4; and the structure of $M_T$ is shown in formula (1), $A_x$ is $A_3'$, the structure of the linker is shown in formula (ii), and preferably, $n_1$ is 1 and $n_2$ is 4.

In certain embodiments, Y is 1, X is 2, the structure of the two M are the same as shown in formula (1'), $A_x$ is $A_1'$, and the structure of the linker is shown in formula (iv), and preferably, n is 1; structure of $M_T$ is shown in formula (4), $A_x$ is $A_1'$, and the structure of the linker is shown in formula (v); and preferably, n is 4.

Exemplary compounds of the present disclosure include:
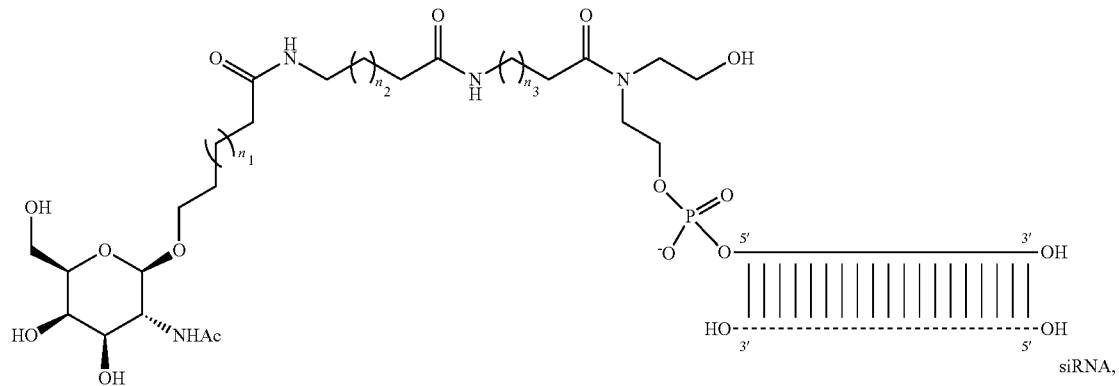
ZW1001
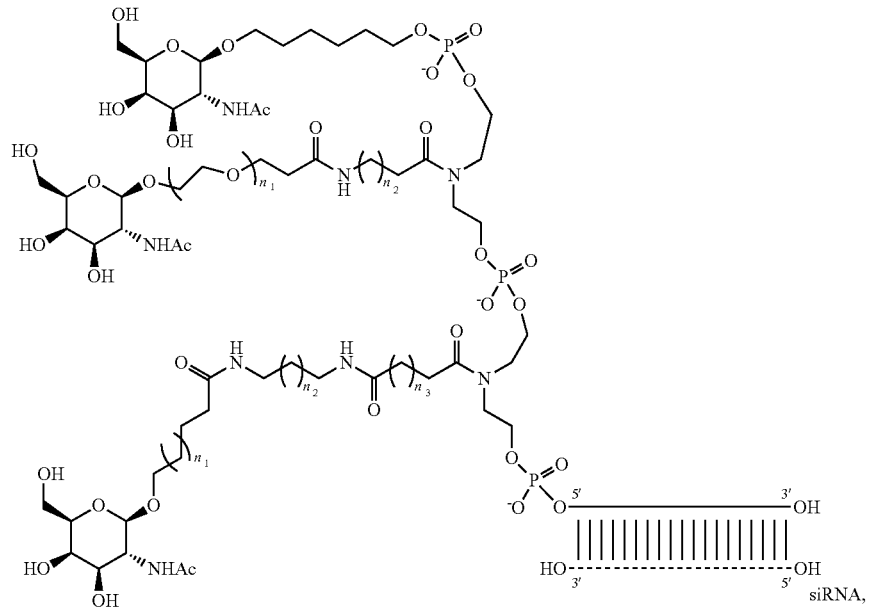
ZW1002
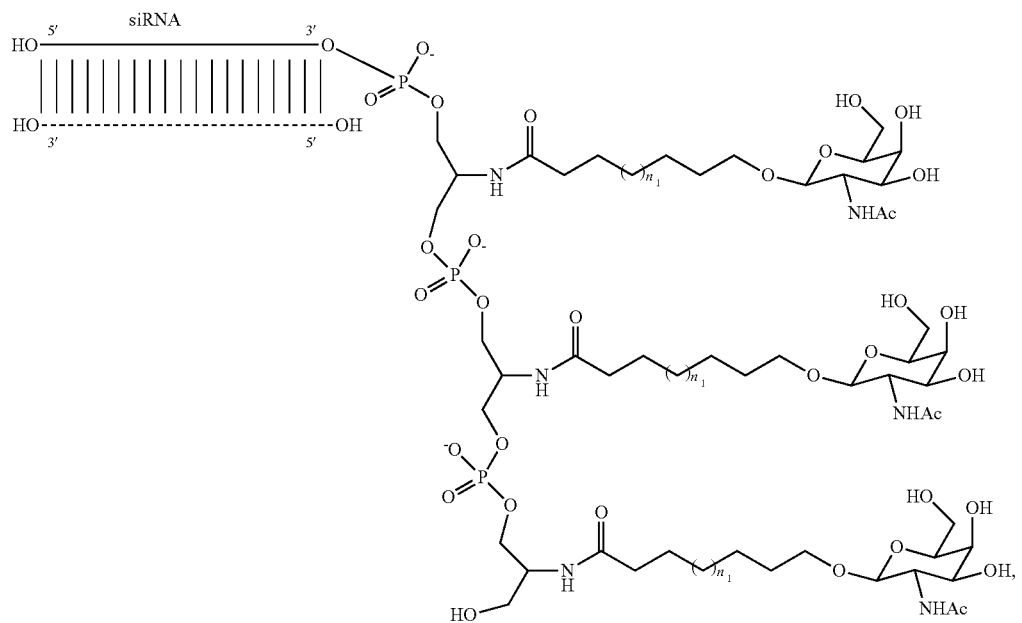
ZW1003

-continued
ZW1004
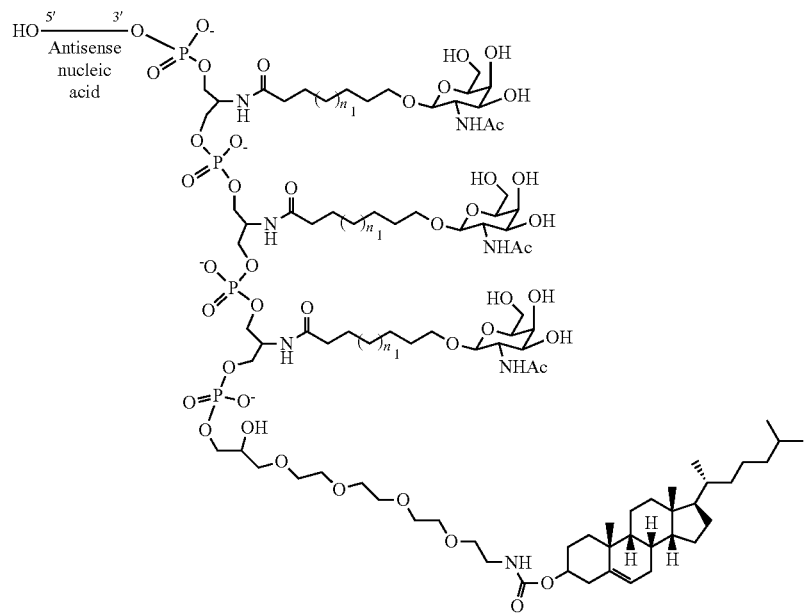
ZW1005
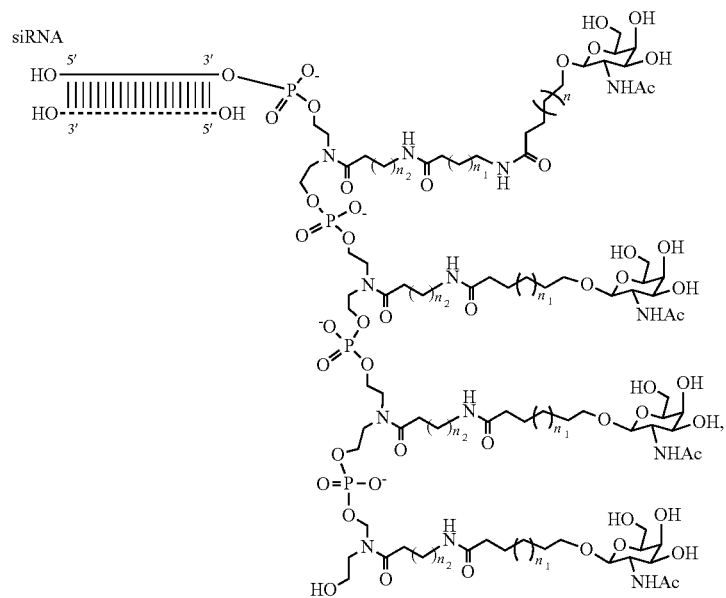

-continued

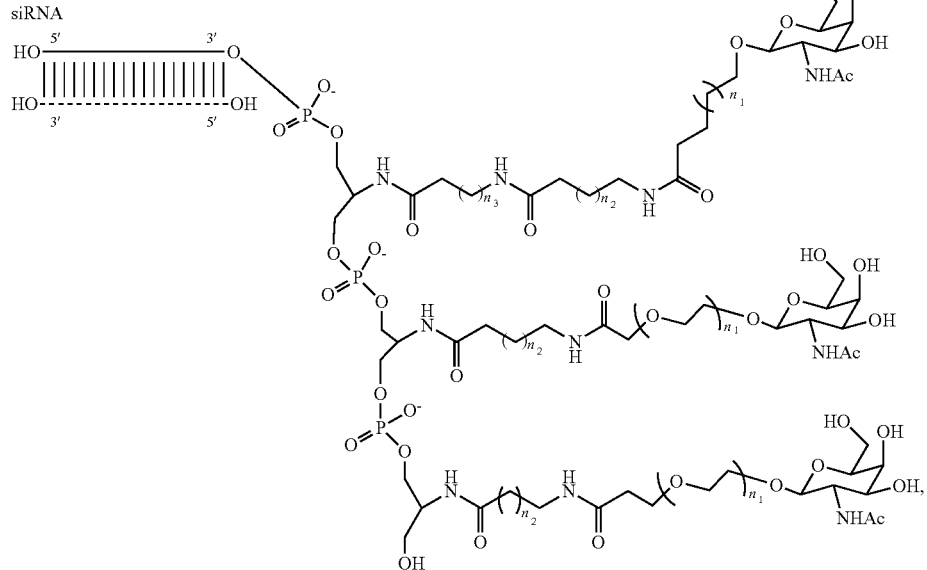

ZW1006

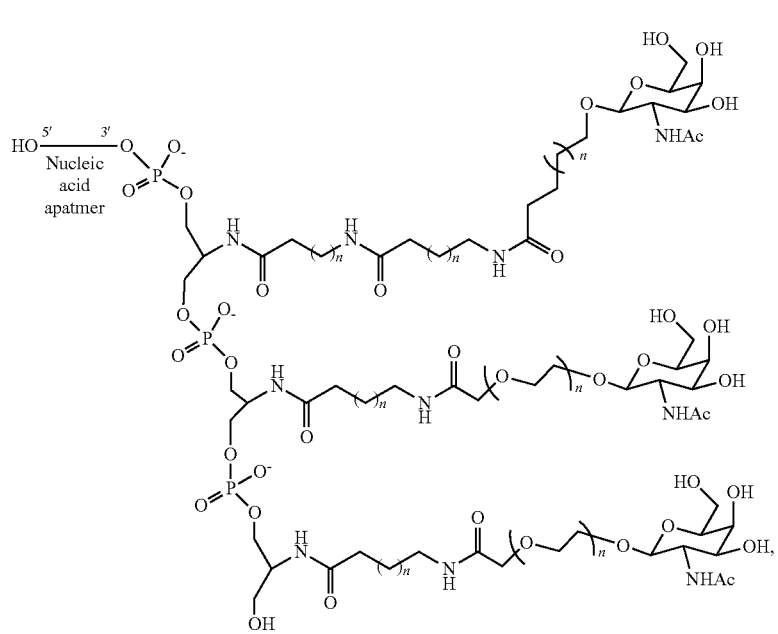

ZW1007 wherein $n_1$, $n_2$, $n_3$ and n are each independently selected from integers between 1 and 10.

In another aspect, the application provides a compound can be used for modifying an oligonucleotide, the compound having a ligand thereon and a chemical group reactive with the oligonucleotide, and a linker arm linking the ligand to the chemical group.

Therefore, the present application relates to compounds having general formulas $A_x$-linker-$R_1$, $A_x$-linker-$R_2$, $A_x$-linker-$R_3$, and $A_x$-linker-$R_4$, wherein $A_x$ is a ligand, and the linker is a linker arm, $R_1$ is

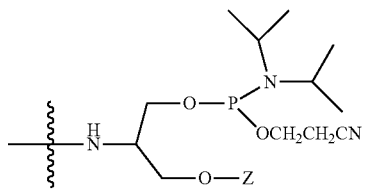

$R_2$ is

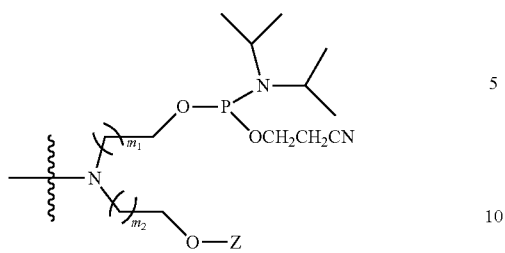

wherein $m_1$ and $m_2$ are each independently selected from integers between 1 and 10.

$R_3$ is

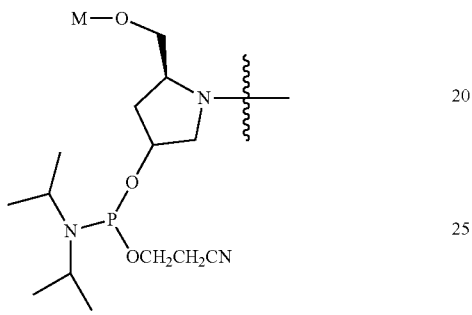

$R_4$ is

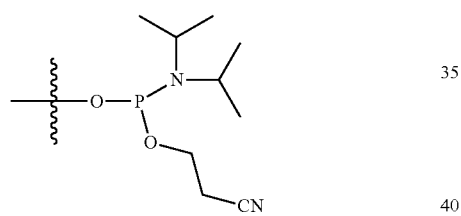

In the $R_1$, $R_2$, and $R_3$, Z is a protecting group for hydroxy, preferably, Z is each independently 4,4-dimethoxytriphenylalkyl (DMTr) or 4-methoxytriphenylchloromethyl (MMT).

In certain embodiments, $A_x$ is a ligand of a human asialoglycoprotein receptor (ASGPR).

In certain embodiments, $A_x$ is galactose, acetylgalactosamine, a galactose-containing polysaccharide, an acetylgalactosamine-containing polysaccharide, galactose derivative (e.g., an ester of galactose, such as galactoacetate), or an acetylgalactosamine derivative (e.g., an ester of acetylgalactosamine, such as acetylgalactosamine acetate). Optionally, $A_x$ is also each independently provided with a modifying group, such as a carbonylalkyl or an esteralkyl, preferably the alkyl portion of the carbonylalkyl or the esteralkyl is a $C_{1-6}$ alkyl or a $C_{6-12}$ alkyl.

In certain embodiments, $A_x$ is selected from:

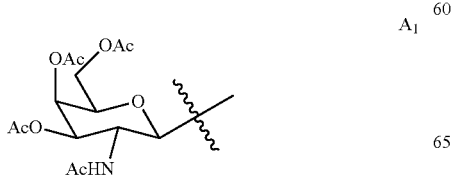
$A_1$

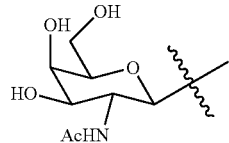
$A_1'$

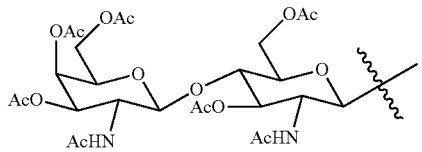
$A_2$

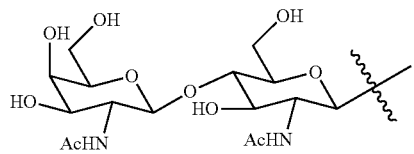
$A_2'$

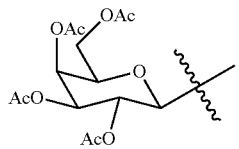
$A_3$

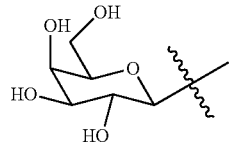
$A_3'$

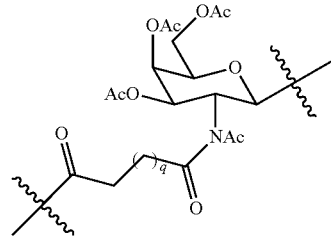
$A_4$

Wherein q ia selected from an integer between 1 and 10

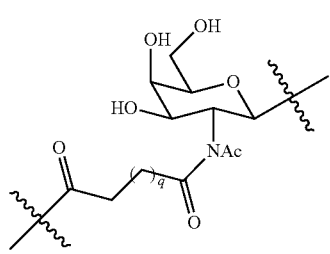
$A_4'$

Wherein q ia selected from an integer between 1 and 10

-continued

A$_5$

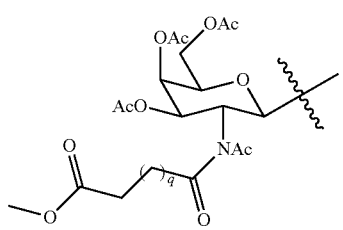

Wherein q ia selected from an integer between 1 and 10

A$_5'$

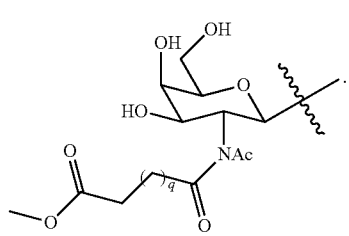

Wherein q ia selected from an integer between 1 and 10

In certain embodiments, the structure of the linker is shown in formula (i), (ii), (iii), (iv), or (v):

(i)

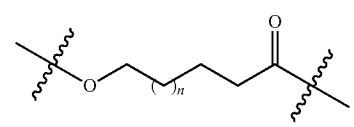

wherein n is selected from an integer between 1 and 10, preferably n is 1 or 6;

(ii)

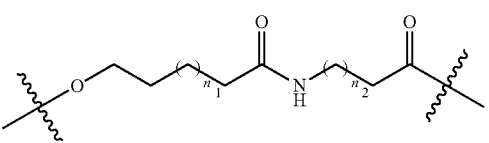

wherein $n_1$ and $n_2$ are each independently selected from integers between 1 and 10, preferably $n_1$ is 1, and preferably $n_2$ is 4;

(iii)

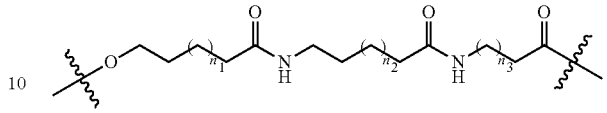

wherein $n_1$, $n_2$, $n_3$ and n are each independently selected from integers between 1 and 10, preferably $n_1$ is 1, preferably $n_2$ is 3, and preferably $n_3$ is 4;

(iv)

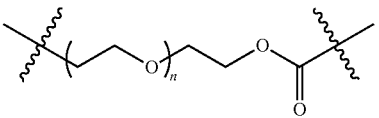

wherein n is selected from an integer between 1 and 10, preferably n is 1;

(v)

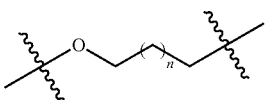

wherein n is selected from an integer between 1 and 10, preferably n is 4.

For the compound having the general formula of A$_x$-linker-R$_1$, in certain embodiments, the compound has one of the following characteristics:

(1) A$_x$ is A$_1$, A$_2$ or A$_3$, the structure of the linker is shown in formula (i), and preferably, n is 1 or 6;

(2) A$_x$ is A$_1$, the structure of the linker is shown in formula (ii), and preferably, $n_1$ is 1 and $n_2$ is 4;

(3) A$_x$ is A$_1$, the structure of the linker is shown in formula (iii), and preferably, $n_1$ is 1, $n_2$ is 3 and $n_3$ is 4;

(4) A$_x$ is A$_1$, the structure of the linker is shown in formula (iv), and preferably, n is 1;

In certain embodiments, the compound having the general formula of A$_x$-linker-R$_1$ is selected:

A$_1$-I-R$_1$

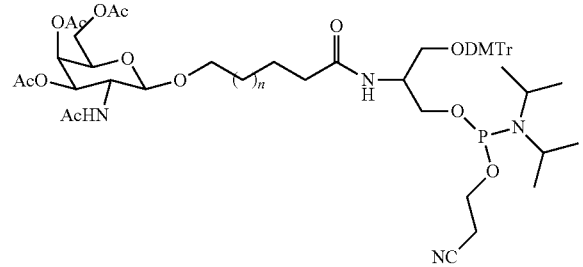

wherein n is selected from an integer between 1 and 10,

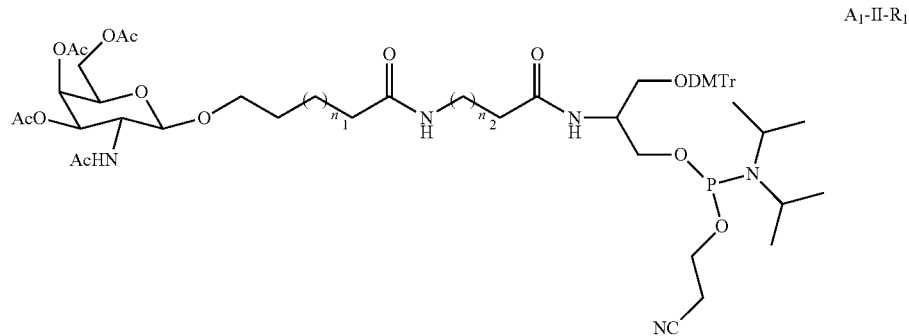

A₁-II-R₁ wherein $n_1$ and $n_2$ are each independently selected from integers between 1 and 10,

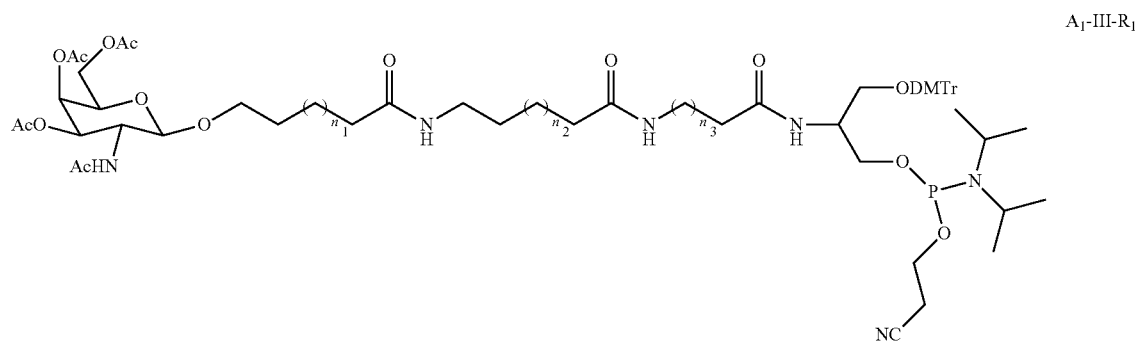

A₁-III-R₁ wherein $n_1$, $n_2$, and $n_3$ are each independently selected from integers between 1 and 10.

For the compound having the general formula of $A_x$-linker-$R_2$, in certain embodiments, the compound has one of the following characteristics:

(1) $A_x$ is $A_1$, $A_2$ or $A_3$, the structure of the linker is shown in formula (i), and preferably, n is 1 or 6; and (2) $A_x$ is $A_1$, the structure of the linker is shown in formula (ii), and preferably, $n_1$ is 1 and $n_2$ is 4.

In certain embodiments, the compound having the general formula of $A_x$-linker-$R_2$ is selected:

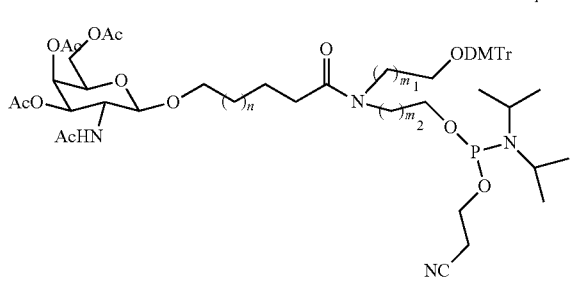

A₁-I-R₂ wherein n, $m_1$ and $m_2$ are each independently selected from integers between 1 and 10, $A_1\text{-II-}R_2$

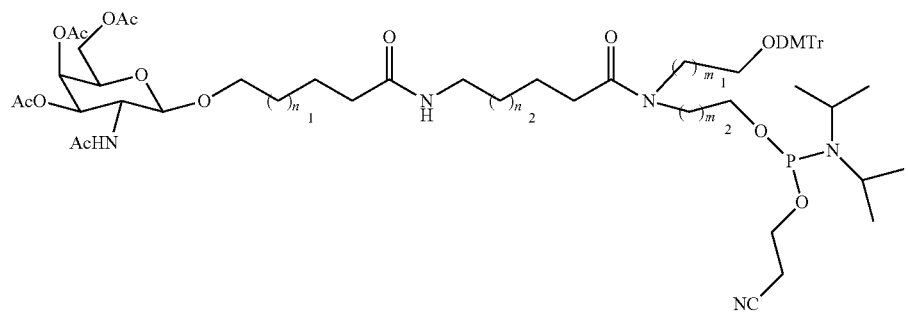

wherein $n_1$, $n_2$, $m_1$ and $m_2$ are each independently selected from integers between 1 and 10, $A_1\text{-III-}R_2$

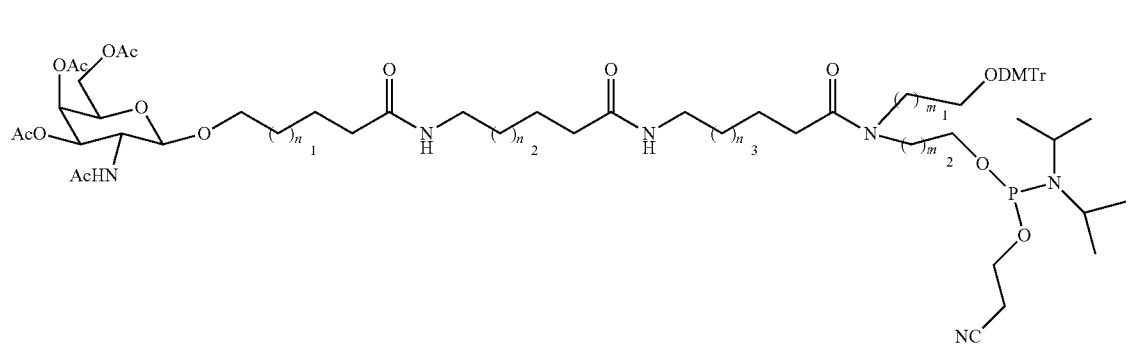

wherein $n_1$, $n_2$, and $n_3$, $m_1$ and $m_2$ are each independently selected from integers between 1 and 10.

For the compound having the general formula of $A_x$-linker-$R_3$, in certain embodiments, $A_x$ is $A_3$, $A_2$ or $A_3$, the structure of the linker is shown in formula (i), and preferably, n is 1 or 6.

For the compound having the general formula of $A_x$-linker-$R_4$, in certain embodiments, $A_x$ is $A_1$, the structure of the linker is shown in formula (v), and preferably, n is 4.

In one aspect, the present application provides a method for modifying an oligonucleotide, comprising linking one or more compounds (e.g., 2, 3, 4, 5, 6, 7, 8, 9 or 10) to the oligonucleotide, the one or more compounds is each independently selected from compounds having general formulas $A_x$-linker-$R_1$, $A_x$-linker-$R_2$, $A_x$-linker-$R_3$, or $A_x$-linker-$R_4$. Preferably, in the method, the linking is achieved by a chemical reaction of the

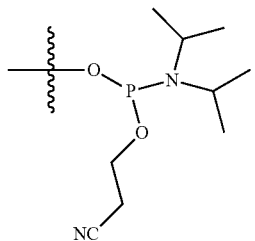

on the compound. In certain embodiments, the method is used for solid phase synthesis.

The application provides another method for modifying oligonucleotides, which comprises the following steps:

step (1): providing an oligonucleotide and linking a first compound to the oligonucleotide to obtain a conjugate M-containing oligonucleotide, the first compound is selected from compounds having general formulas $A_x$-linker-$R_1$, $A_x$-linker-$R_2$, $A_x$-linker-$R_3$, or $A_x$-linker-$R_4$ as defined above; and step (2): linking a second compound to the conjugate M formed in the previous step, the second compound being selected from compounds having general formulas $A_x$-linker-$R_1$, $A_x$-linker-$R_2$, $A_x$-linker-$R_3$, or $A_x$-linker-$R_4$ as defined above.

Optionally, the method further comprises a step (3): repeating step (2) one or more times (e.g., 2-9 times).

Optionally, the method further comprises a step (4): repeating step (1), step (2), and step (3) one or more times (e.g., 2-9 times).

Preferably, in the steps (1) and (2), the linking is achieved by a chemical reaction of the

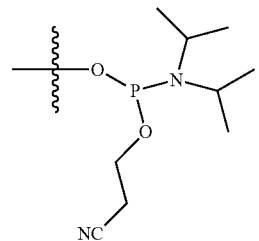 [SMILES: *OP(OCCC#N)N(C(C)C)C(C)C]

on the first compound or the second compound.

The oligonucleotide used in any of the modification methods of the present disclosure may be a single-stranded oligonucleotide or a double-stranded oligonucleotide. Optionally, the oligonucleotide may comprise one or more modified nucleotides. In certain embodiments, the one or more modified nucleotides are each independently selected from: 2'-methoxyethyl modified nucleotides, 2'-O-alkyl modified nucleotides (e.g. 2'-O-methyl modified nucleotides), 2'-O-allyl modified nucleotides, 2'-C-allyl modified nucleotides, 2'-fluoro modified nucleotides, 2'-deoxy modified nucleotides, 2'-hydroxy modified nucleotides, locked nucleotides, HNAs, and UNA. In certain embodiments, the modified nucleotide is selected from 2'-O-alkyl modified nucleotides, 2'-fluoro modified nucleotides.

In certain embodiments, the oligonucleotide is provided with a terminal modifier, preferably the terminal modifier is selected from: cholesterol, polyethylene glycol, fluorescent probes, biotin, polypeptides, vitamins, tissue targeting molecules and any combination thereof.

In certain embodiments, the phosphate-containing backbone of the oligonucleotide is modified, preferably the modification is a phosphorthioate modification.

In certain embodiments, the oligonucleotide is a siRNA. In certain embodiments, the siRNA comprises a sense strand and an antisense strand complementary to form a double strand. In certain embodiments, the siRNA comprises a sequence as shown in SEQ ID NO: 1, SEQ ID NO: 2, SEQ ID NO: 3, or SEQ ID NO: 4.

The application also provides use of a compound having a general formula of $A_x$-linker-$R_1$, $A_x$-linker-$R_2$, $A_x$-linker-$R_3$, or $A_x$-linker-$R_4$ as defined above to modify oligonucleotides. The application also provides a kit comprising at least one selected from a compound having a general formula of $A_x$-linker-$R_1$, $A_x$-linker-$R_2$, $A_x$-linker-$R_3$, or $A_x$-linker-$R_4$ as defined above. In certain embodiments, the kit further comprises a reagent for synthesizing and/or modifying oligonucleotides (e. g: a solid support, DNA monomer, RNA monomer, a modified monomer, an activator, an oxidizer, a deprotection reagent, a buffer, and any combination thereof.

In one aspect, the application provides a pharmaceutical composition comprising a compound of the present disclosure comprising an oligonucleotide and a conjugate group, and optionally a pharmaceutically acceptable carrier. In certain embodiments, the pharmaceutical composition is used to prevent and/or treat a liver-related disease in a subject.

The pharmaceutical compositions of the present disclosure may be formulated in any pharmaceutically acceptable dosage form. In certain embodiments, the dosage form is selected from powders, tablets, granules, capsules, solutions, emulsions, suspensions, injections, sprays, aerosols, and dry powder inhalations. In certain embodiments, the formulations may be administered to a patient or subject in need of prevention and/or treatment in any suitable manner of administration, e.g., oral, parenteral, rectal, pulmonary, or topical administration. When used for oral administration, the formulation may be an oral formulation, e.g., an oral solid formulation such as a tablet, a capsule, a pill, a granule, etc.; alternatively, an oral liquid preparation such as oral solutions, oral suspensions, syrups, etc. The oral formulation may also contain suitable fillers, binders, disintegrants, lubricants and the like. When used for parenteral administration, the formulation may be an injection, including injection solutions, sterile powders for injection and concentrated solutions for injection. For injections, they can be produced by conventional methods known in the pharmaceutical field. When an injection is formulated, no additional agent may be added to the formulation or an appropriate additional agent may be added depending on the nature of the drug.

In one aspect, the application provides the use of a compound of the present disclosure comprising an oligonucleotide and a conjugate group for preventing and/or treating a liver-related disease in a subject.

In one aspect, the application provides a method for preventing and/or treating a liver-related disease in a subject, comprising administering to the subject in need an effective amount of a compound comprising an oligonucleotide and a conjugate group of the present disclosure.

In certain embodiments, the liver-related disease is selected from: hereditary angioedema, familial tyrosinemia type I, Alagille syndrome, α-1-antitrypsin deficiency, bile acid synthesis and metabolic defects, biliary atresia, cystic fibrosis liver disease, idiopathic neonatal hepatitis, mitochondrial liver disease, progressive familial intrahepatic cholestasis, primary sclerosing cholangitis, transthyretin amyloidosis, hemophilia, homozygous familial hypercholesterolemia, hyperlipidemia, steatohepatitis, nonalcoholic steatohepatitis (NASH), nonalcoholic fatty liver disease (NAFLD), hyperglycemia and diseases involving abnormally increased hepatic glucose production similar to type II diabetes, hepatitis, hepatic porphyrins.

In certain embodiments, the subject is a mammal, such as a bovine, equine, ovine, porcine, canine, feline, rodent, primate; for example, the subject is a human.

In the present disclosure, unless otherwise indicated, the scientific and technical terms used herein have the meanings commonly understood by one of ordinary skill in the art. Moreover, the laboratory procedures referred to herein are all conventional procedures widely used in the corresponding field. Meanwhile, in order to better understand the present disclosure, definitions and explanations of related terms are provided below.

As used herein, the term "oligonucleotide" refers to an oligomeric compound containing a plurality of linked chemically modified or unmodified nucleotides having a length of less than about 100 nucleotides (e.g., 1-20 nucleotides or 1-50 nucleotides). In certain embodiments, the oligonucleotide can include a non-nucleic acid conjugate group. In certain embodiments, the oligonucleotide comprises ribonucleic acid (RNA) or deoxyribonucleic acid (DNA). In certain embodiments, the oligonucleotide is double-stranded or single-stranded. In certain embodiments, the oligonucleotide is a siRNA, an aptamer, or an antisense nucleic acid.

As used herein, the term "conjugate" or "conjugate group" means an atom or group of atoms bound to an oligonucleotide. In some cases, the conjugate groups alter one or more properties of the oligonucleotide to which they are linked, including but not limited to pharmacodynamics, pharmacokinetics, binding, absorption, cell distribution, cell uptake, charge, and/or clearance properties.

As used herein, the term "receptor" refers to a biological macromolecule composed of glycoproteins or lipoproteins, present in the cell membrane, cytoplasm, or nucleus of a cell, with different receptors having specific structures and configurations. As used herein, the term "ligand" refers to a substance that has the ability to recognize and bind to a receptor. In certain embodiments, the ligand is a ligand having affinity for an asialoglycoprotein receptor (ASGPR). In certain embodiments, the ligand is a carbohydrate, such as monosaccharides and polysaccharides, including but not limited to: galactose, N-acetylgalactosamine, mannose, glucose, glucosamine and fucose.

As used herein, the term "polysaccharide" refers to a polymer formed from a plurality of monosaccharide groups linked by glycosidic linkages. In the present disclosure, polysaccharides include oligoses and oligosaccharides. Generally, "oligose" refers to a polymer composed of 2-10 monosaccharide groups linked by glycosidic bonds, and "oligosaccharide" refers to a polymer composed of less than 20 monosaccharide groups linked by glycosidic bonds.

As used herein, the term "about" should be understood by those skilled in the art and will vary to some extent depending on the context in which it is used. If, depending on the context in which the term is used, its meaning is not clear to those skilled in the art, then the meaning of "about" is such that the deviation does not exceed plus or minus 10% of the specified value or range.

As used herein, the term "preventing" refers to preventing or delaying the onset of a disease.

As used herein, the term "treating" refers to curing or at least partially arresting the progression of a disease, or alleviating the symptoms of a disease.

As used herein, the term "effective amount" refers to an amount effective to achieve the intended purpose. For example, an amount effective to prevent a disease refers to an amount effective to prevent, arrest, or delay the onset of the disease. Determination of such effective amounts is within the ability of one skilled in the art.

Advantageous Effects of the Present Disclosure

Compared with the prior art, the present disclosure has the following beneficial effects:

Compared with related disclosures of Alnylam Pharmaceuticals and ISIS Pharmaceuticals (US20150119444A1, US20150119445A1, US20150126718A1), the present disclosure has the following remarkable differences:

1. Different Chemical Structure.

The structure designed by two companies is that a multiantennary ASGPR ligand is linked to an oligonucleic acid at one time; the structure designed by the present disclosure is that a single ASGPR ligand is coupled with oligonucleic acid for many times through solid-phase chemical synthesis of nucleic acid phosphoramidite to realize multi-ligand modification. The advantages of multiple solid-phase synthesis couplings of a single ASGPR ligand are that (1) the synthesis steps are shortened, and the scale-up production is easy to realize. The solid phase synthesis linking efficiency of each ligand for the coupling reaction is more than 98%, the linking efficiency of three ligands is more than 94%, the solid phase synthesis can be automatically completed by equipment, and purification is not needed in the connection reaction. Compared with liquid phase synthesis, three ligands are combined into a single molecule to be linked, the efficiency is higher, speed is higher, and scale-up production is easier. (2) Expanded the scope of oligonucleic acid modification. According to the report (lee et al., Carbohydrates in Chemistry and Biology; 4: 549, 2000), the distance between GalNAc and the center in the triantennary structure is 41 Å, 18 Å, 20 Å, and unequal is more favorable for binding with ASGPR receptor. Due to the limitations of the preparation methods, GalNAc is equidistant from the center (17 atoms) in the triantennary structure used by both companies. According to the present disclosure, each ASGPR ligand is independently linked with the oligonucleic acid, which can easily control the spatial distance of the central ligand, adjust the number of ligands, form hundreds of combinations, expand the types of oligo nucleic acid modifications, and help find more active medicine molecules. (3) The ASGPR ligand types are expanded. A series of new ASGPR ligand substrates have been prepared on the basis of GalNAc, and the screening of these new ligands would be beneficial to the development of new oligonucleic acid drugs.

2. Ligands are Covalently Linked to Oligonucleic Acids by Different Synthetic Methods.

Alnylam Pharmaceuticals employed the linking of a triantennary GalNAc ligand to a solid support, the modified solid support is used for solid phase synthesis of oligonucleic acids, thereby linking the ligand to the 3' end of the oligonucleic acid. ISIS pharmaceutics attempted to link a triantennary GalNAc ligand to the 5' end by a nucleic acid phosphoramidite solid-phase synthesis method, but failed due to large steric hindrance (Efficient Synthesis and Biological Evaluation of 5'-GalNAc). Thus they developed a liquid-phase method of a liquid-phase triantennary GalNAc ligand and a terminal amino-modified oligonucleotide, which achieved a reaction time of 3 hours and a reaction efficiency of greater than 95%. According to the method, each ligand is independently linked with the oligonucleic acid, small in the molecular steric hindrance, and high in the connection efficiency.

3. Oligonucleotide Sites and Combinations May be Modified Differently.

Terminal sites in oligonucleic acid drug molecules are often modified with cholesterol, polyethylene glycol (PEG) and the like to improve pharmacokinetic properties. Triantennary GalNAc ligands designed by Alnylam and ISIS Pharmaceuticals are only used for terminal modifier of oligonucleotide strands, occupying the site of terminal modifier and reducing the number of species available for oligonucleotide modification. The novel compound can be used for modifying any position of the oligonucleic acid in solid phase synthesis, and other modifications are not affected by the terminal. The preparation of novel compounds mixed with terminal cholesterol to modify oligonucleic acids is described in the examples of the present disclosure.

Embodiments of the present disclosure will now be described in detail with reference to the accompanying drawings and examples, however, it will be understood by those skilled in the art that the following drawings and examples are merely illustrative of the present disclosure and are not intended to limit the scope of the present disclosure. Various objects and advantageous aspects of the present disclosure will become apparent to those skilled in the art from the accompanying drawings and the following detailed description of the preferred embodiments.

BRIEF DESCRIPTION OF THE DRAWINGS

FIG. 1 shows the GalNAc binding curves for each sample in Example 35.

SEQUENCE OF INFORMATION

Information on the sequences to which the present disclosure relates is provided in the following table:

| Sequence number (SEQ ID NO:) | Description |
| --- | --- |
| 1 | Artificial sequence |
| 2 | Artificial sequence |

| Sequence number (SEQ ID NO:) | Description |
|---|---|
| 3 | Artificial sequence |
| 4 | Artificial sequence |

Sequence 1 (SEQ ID NO: 1): 19nt
CAGCAAGUGUGACAGUCAU

Sequence 2 (SEQ ID NO: 2): 25nt
AUGACUGUCACACUUGCUGGCCUGU

Sequence 3 (SEQ ID NO: 3): 19nt
CAGGCCAGCAAGUGUGACA

Sequence 4 (SEQ ID NO: 4): 21nt
UGUCACACUUGCUGGCCUGUC

DETAILED DESCRIPTION OF THE DISCLOSURE

Embodiments of the present disclosure will be described in detail below with reference to examples, but those skilled in the art will appreciate that the following examples are only illustrative of the present disclosure and are not to be construed as limiting the scope of the present disclosure. Specific conditions which are not noted in the examples are carried out under conventional conditions or conditions recommended by the manufacturer. The reagents or instruments used of which the manufacturer are not noted are conventional products commercially available.

Example 1 Synthesis of Compound R'$_1$-H

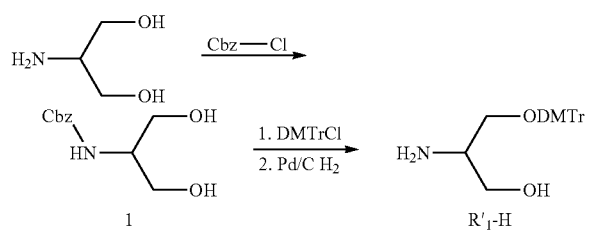

Using serinol as a raw material, compound 1 was prepared according to the reference (Choi J Y, Borch R F. Highly efficient synthesis of enantiomerically enriched 2-hydroxymethylaziridines by enzymatic desymmetrization. [J]. Organic letters, 2007, 9(2):215-218), and compound R'$_1$-H was further prepared to obtain a white solid with a total yield of 49% over two steps. $^1$HNMR (400 MHz, DMSO-d6) δ:7.41-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.16 (s, 2H), 4.63-4.58 (m, 1H), 4.05-3.97 (m, 1H), 3.74 (s, 6H), 3.04-2.99 (m, 2H), 2.95-2.90 (m, 2H). MS(ESI), m/z:416.3 ([M+Na]+).

Example 2 Synthesis of Compound R'$_2$-H

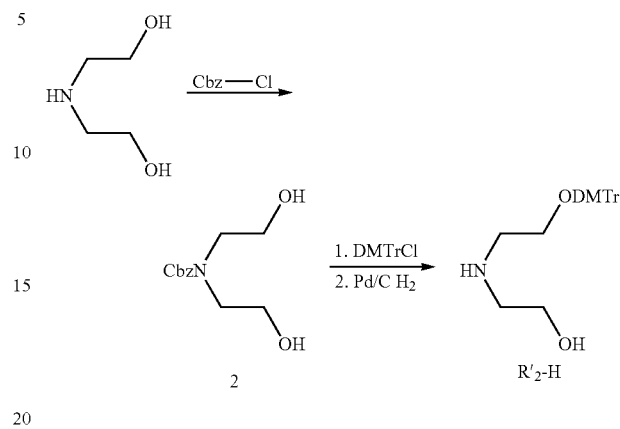

Referring to the method of Example 1, compound R'$_2$-H was prepared as a white solid in 55% yield. $^1$H NMR (400M Hz, DMSO-d6) δ:7.42-7.37 (d, J=7.2 Hz, 2H), 7.35-7.29 (t, J=6.9 Hz, 2H), 7.28-7.19 (m, 5H), 6.92-6.86 (d, J=8.2 Hz, 4H), 5.17 (s, 1H), 4.63-4.59 (m, 1H), 3.74 (s, 6H), 3.05-2.99 (m, 2H), 2.96-2.90 (m, 2H), 2.88-2.81 (m, 4H). MS(ESI), m/z:430.3 ([M+Na]+).

Example 3 Synthesis of Compound R'3-H

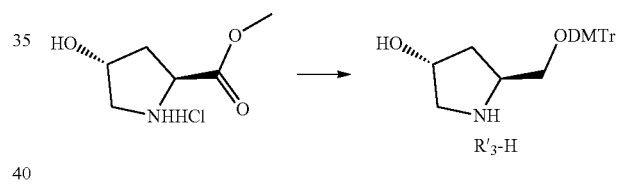

Using L-hydroxyproline methyl ester hydrochloride as a raw material, the compound R'$_3$-H was prepared referring to the method of Example 1 to obtain a white solid with a yield of 45%. $^1$H NMR (400 MHz, DMSO-d6) δ:7.42-7.37 (d, J=7.2 Hz, 2H), 7.35-7.29 (t, J=6.9 Hz, 2H), 7.28-7.19 (m, 5H), 6.92-6.86 (d, J=8.2 Hz, 4H), 5.17 (s, 1H), 4.63-4.59 (m, 1H), 3.74 (s, 6H), 3.05-2.99 (m, 3H), 2.90-2.86 (m, 2H), 2.77-2.71 (m, 1H), 1.88-1.81 (m, 2H). MS(ESI), m/z:442.5 ([M+Na]+).

Example 4 Synthesis of Compound A$_1$-I$_1$

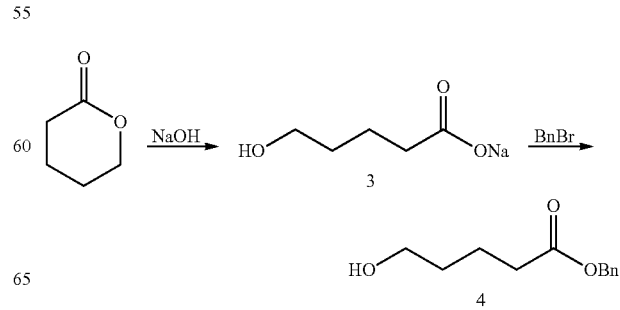

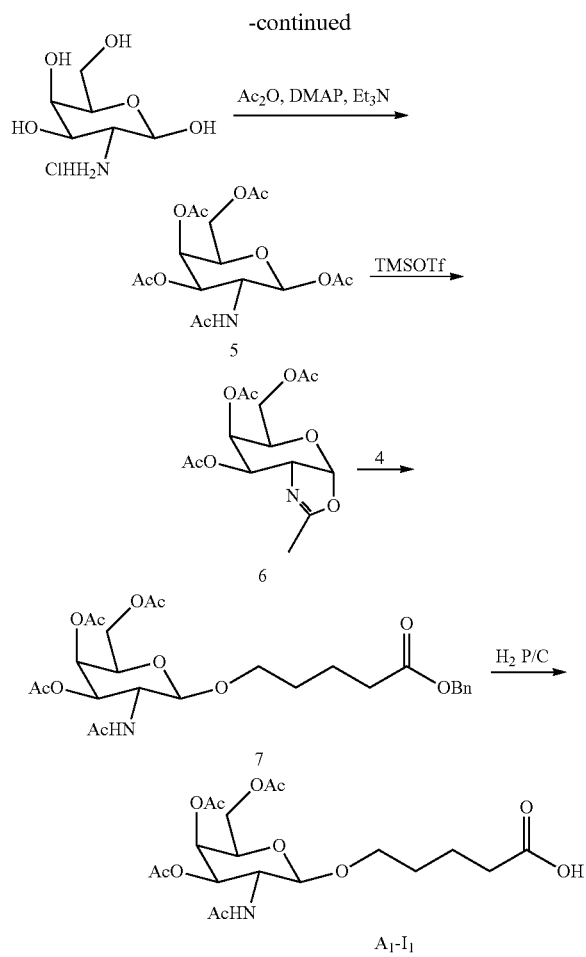

(1) Synthesis of Compound 3

In a 1 L round bottom flask, δ-valerolactone (100 g, 1 mol), sodium hydroxide (40 g, 1 mol) and 400 mL of deionized water were added, mixed, reacted for 6 hours at 70° C., and monitored by TLC until the reaction was completed; the reaction solution was spin-dried, added with 200 mL of toluene, and spin-dried to obtain 140 g of a white solid.

(2) Synthesis of Compound 4

In a 1 L round bottom flask, compound 3 (140 g, 1 mol), 500 mL of anhydrous acetone, benzyl bromide (205.2 g, 1.2 mol), catalyst tetrabutylammonium bromide (16.2 g, 0.05 mol) were added, and refluxed under heating; the reaction was monitored by TLC; after 24 hours, the reaction was complete; the reaction liquid was cooled to room temperature, acetone was removed under reduced pressure, the residue was dissolved in 500 mL of ethyl acetate, and washed with 200 mL of saturated sodium bisulfate solution, 200 mL of saturated sodium bicarbonate solution, and 200 mL of saturated brine successively; and the organic phase was dried over anhydrous sodium sulfate, concentrated, and passed through a silica gel column (petroleum ether:ethyl acetate V:V=1:1) to isolate 175 g of a clear oily liquid with a yield of 84%.

(3) Synthesis of Compound 5

In a 1 L round bottom flask, D-galactose hydrochloride (100 g, 0.46 mol) and 450 mL of anhydrous pyridine were added, and 325 mL of acetic anhydride, triethylamine (64.5 mL, 0.46 mol) and DMAP (2 g, 0.016 mol) were slowly added under an ice bath. After overnight reaction at room temperature, a large amount of solid was precipitated, which was filtered by suction and the filter cake was rinsed with 200 mL of 0.5 N HCl solution to obtain 162.5 g of a white solid with a yield of 90%. $^1$H NMR (400 MHz, DMSO-d6) δ:7.88 (d, J=9.2 Hz, 1H), 5.63 (d, J=8.8 Hz, 1H), 5.26 (d, J=3.1 Hz, 1H), 5.05 (d, J=11.3, 3.3 Hz, 1H), 4.36 (m, 4H), 2.11 (s, 3H), 2.03 (s, 3H), 1.98 (s, 3H), 1.90 (s, 3H), 1.78 (s, 3H).

(4) Synthesis of Compound 6

In a 250 mL round-bottomed flask, compound 5 (10 g, 25.7 mmol) and 100 mL of anhydrous dichloromethane were added, and stirred for 10 min, then added with trimethylsilyl trifluoromethanesulfonate (7 mL, 38.7 mmol), and allowed to react overnight at room temperature; the reaction solution was slowly poured into an aqueous solution (200 mL) of sodium bicarbonate (7 g, 79.5 mmol), and stirred for 0.5 hours; the organic phase was separated, dried over anhydrous sodium sulfate and concentrated under reduced pressure to obtain 7.78 g of a light yellow gum with a yield of 92%.

(5) Synthesis of Compound 7

In a 100 mL round bottom flask, compound 6 (5 g, 15.2 mmol) and compound 4 (3.8 g, 18.25 mmol) were dissolved in 50 mL of anhydrous 1,2-dichloroethane, stirred for 10 min, and trimethylsilyl trifluoromethanesulfonate (0.55 mL, 3 mmol) was added, reacted overnight at room temperature; the reaction solution was extracted with dichloromethane, and the organic phase was washed twice with 50 mL of saturated sodium bicarbonate Solution, dried over anhydrous sodium sulfate, concentrated under reduced pressure, and passed through a silica gel column (petroleum ether: ethyl acetate V:V=3:2) to isolate 6.94 g of a clear oily liquid with a yield of 85%. $^1$HNMR (400 MHz, DMSO-d6) δ:7.69 (d, J=9.3 Hz, 1H), 7.33-7.16 (m, 5H), 5.28 (d, J=5.3 Hz, 1H), 4.95 (s, 2H), 4.93 (q, J=4.2 Hz, 1H), 4.40 (d, J=8.6 Hz, 1H), 4.00-3.86 (m, 3H), 3.73-3.56 (m, 2H), 3.36-3.21 (m, 1H), 2.53 (t, J=8.2 Hz, 2H), 2.11 (s, 3H), 1.89 (s, 3H), 1.83 (s, 3H), 1.65 (s, 3H), 1.59-1.36 (m, 4H). MS(ESI), m/z:560.2 ([M+Na]+).

(6) Synthesis of Compound $A_1$-$I_1$

In a 50 mL round bottom flask, compound 7 (3.3 g, 6.1 mmol), Pd/C (0.33 g, 10%) were dissolved in 5 mL of methanol and 20 mL of ethyl acetate, introduced with a hydrogen balloon and reacted overnight at room temperature. The reaction solution was filtered through diatomite, and rinsed with diatomite methanol; and the filtrate was concentrated under reduced pressure and spin-dried to obtain 2.8 g of a white solid with a yield of 95.5%. $^1$H NMR (400 MHz, DMSO-d6) δ:11.98 (s, 1H), 7.79-7.75 (d, J=8.9 Hz, 1H), 5.20 (s, 1H), 5.0-4.95 (q, J=4.2 Hz, 1H), 4.46-4.51 (d, J=7.2 Hz, 1H), 4.15-4.07 (m, 3H), 3.89-3.79 (m, 1H), 3.80-3.69 (m, 1H), 3.46-3.36 (m, 1H), 2.22-2.14 (t, J=7.2 Hz, 2H), 2.15 (s, 3H), 2.00 (s, 3H), 1.95 (s, 3H), 1.87 (s, 3H), 1.59-1.42 (m, 4H). MS(ESI), m/z:470.5 ([M+Na]$^+$).

Example 5 Synthesis of Compounds $A_1$-$I_2$

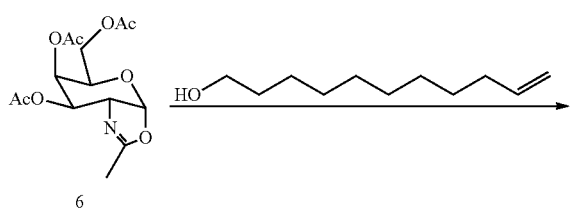

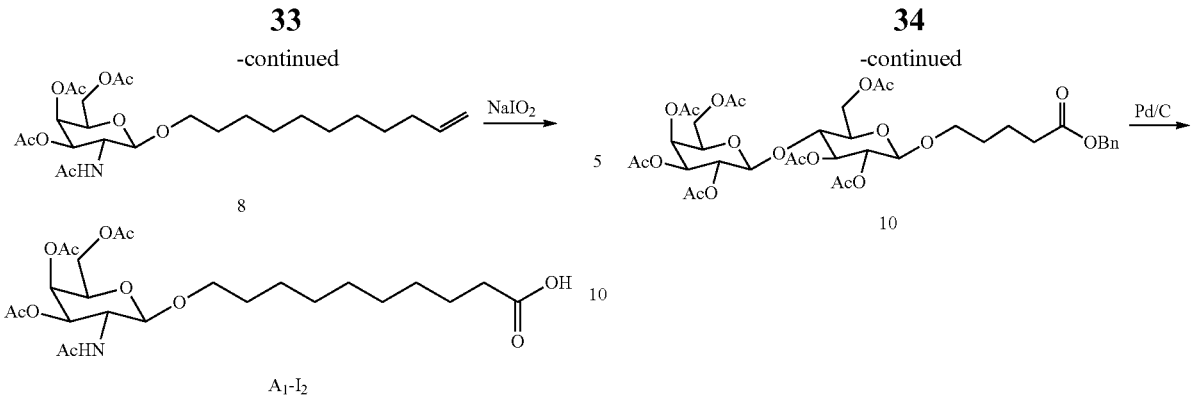

(1) Synthesis of Compound 8

In a 100 mL round bottom flask, compound 6 (5 g, 15.2 mmol) and 10-undecenol (3.1 g, 18.24 mmol) were dissolved in 50 mL of anhydrous dichloromethane, stirred for 10 min, and trimethylsilyl trifluoromethanesulfonate (0.55 mL, 3.0 mmol was added), and reacted overnight at room temperature; the reaction solution was extracted with dichloromethane, and the organic phase was washed twice with 50 mL of saturated sodium bicarbonate solution, dried over anhydrous sodium sulfate, concentrated under reduced pressure, and passed through a silica gel column (petroleum ether:ethyl acetate V:V=3:2) to isolate 6.59 g of a white solid with a yield of 87%. $^1$H NMR (400 MHz, DMSO-d6) δ:7.82 (d, J=3.3 Hz, 1H), 5.86-5.73 (m, 1H), 5.22 (s, 1H), 5.02-4.9 (m, 3H), 4.5-4.98 (s, J=3.5 Hz, 1H), 4.08-3.99 (m, 3H), 3.9-3.88 (m, 1H), 3.73-3.65 (m, 1H), 3.48-3.38 (m, 1H), 2.12 (s, 3H), 2.05-2.01 (m, 2H), 2.00 (s, 3H), 1.88 (s, 3H), 1.66 (s, 3H), 1.5-1.4 (m, 2H), 1.39-1.3 (m, 2H), 1.29-1.19 (m, 10H). MS(ESI), m/z:522.4 ([M+Na]+).

(2) Synthesis of compounds $A_1$-$I_2$

In a 100 mL round bottom flask, compound 8 (4 g, 8.02 mmol), 50 mL of dichloromethane, 50 mL of acetonitrile, and 70 mL of deionized water were added; NaIO$_4$ (6.86 g, 32.1 mmol) was added portionwise; the reaction was carried out at room temperature for 48 h, and the completion of the reaction was monitored by TLC. The reaction solution was added with deionized water (100 mL), and extracted three times with dichloromethane (50 mL×3); the organic phases were combined, dried over anhydrous sodium sulfate, concentrated under reduced pressure and spin-dried to obtain 4.1 g of a light brown gummy product with a yield of 99%. $^1$HNMR (400 MHz, DMSO-d6) δ:11.99 (s, 1H), 7.82 (d, J=3.3 Hz, 1H), 5.22 (s, 1H), 5.02-4.9 (m, 1H), 4.5-4.98 (s, J=3.5 Hz, 1H), 4.08-3.99 (m, 3H), 3.9-3.88 (m, 1H), 3.73-3.65 (m, 1H), 3.48-3.38 (m, 1H), 2.12 (s, 3H), 2.05-2.01 (m, 2H), 2.00 (s, 3H), 1.88 (s, 3H), 1.66 (s, 3H), 1.5-1.4 (m, 2H), 1.39-1.3 (m, 2H), 1.29-1.19 (m, 10H). MS(ESI), m/z:540.26 ([M+Na]+).

Example 6 Synthesis of Compounds $A_2$-$I_2$

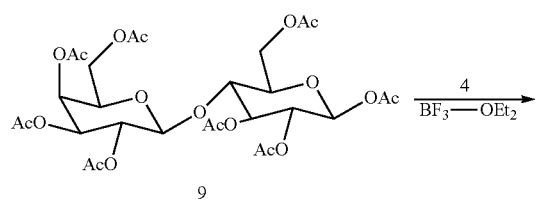

(1) Synthesis of Compound 9

Compound 9 was synthesized with reference to [2] Hudson, C. S.; Johnson, J. J. Am. Chem. Soc. 1915, 37, 1270-1275.

$^1$HNMR (400 MHz, DMSO-d6) δ:5.20 (s, 2H), 4.95 (q, J=4.2 Hz, 2H), 4.51 (d, J=7.2 Hz, 1H), 4.46 (d, J=7.2 Hz, 1H), 4.15-3.97 (m, 6H), 3.89-3.79 (m, 2H), 2.23 (s, 3H), 2.15 (s, 6H), 2.00 (s, 6H), 1.95 (s, 6H), 1.87 (s, 3H). MS(ESI), m/z:701.6 ([M+Na]+).

(2) Synthesis of Compound 10

In a 500 mL round bottom flask, compound 9 (20 g, 29.5 mmol), and compound 4 (9.2 g, 44.3 mmol) were dissolved in 200 mL of anhydrous dichloromethane; BF$_3$—OEt$_2$ (14.8 mL) was added dropwise in an ice bath; the reaction was maintained in an ice bath for 24 h and the completion of the reaction was monitored by TLC. The reaction was filtered by diatomite; and the filtrate was dissolved in 500 mL of ethyl acetate and washed with 200 mL saturated sodium bicarbonate solution and 200 mL saturated brine successively. The organic phase was dried over anhydrous magnesium sulfate, concentrated under reduced pressure and passed through a silica gel column (petroleum ether:ethyl acetate V:V=3:2) to isolate 17.06 g of a white solid with a yield of 70%. MS(ESI), m/z:849.26 ([M+Na]+).

(3) Synthesis of Compound $A_2$-$I_1$

In a 100 mL round bottom flask, compound 10 (10 g, 12.1 mmol), Pd/C (1 g, 10%) were dissolved in 10 mL of methanol and 50 mL of ethyl acetate, charged with nitrogen to replace air, introduced with a hydrogen balloon and reacted overnight at room temperature. The reaction solution was filtered through diatomite, and rinsed with diatomite methanol; and the filtrate was spin-dried under reduced pressure to obtain 8.5 g of a white solid with a yield of 95.5%. H NMR (400 MHz, DMSO-d6) δ:11.98 (s, 1H), 5.20 (s, 2H), 4.95 (q, J=4.2 Hz, 2H), 4.51 (d, J=7.2 Hz, 1H), 4.46 (d, J=7.2 Hz, 1H), 4.15-3.97 (m, 6H), 3.89-3.79 (m, 2H), 3.80-3.69 (m, 1H), 3.46-3.36 (m, 1H), 2.22-2.14 (t, J=7.2 Hz, 2H), 2.15 (s, 6H), 2.00 (s, 6H), 1.95 (s, 6H), 1.87 (s, 3H), 1.59-1.42 (m, 4H). MS(ESI), m/z:759.26 ([M+Na]+).

Example 7 Synthesis of Compounds A$_2$-I$_2$

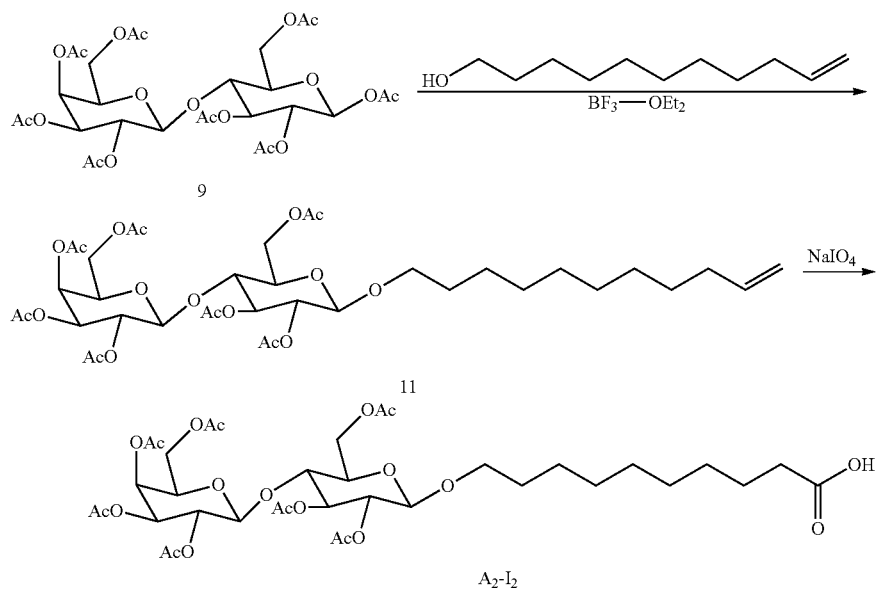

(1) Synthesis of Compound 11

In a 500 mL round bottom flask, compound 9 (20 g, 29.5 mmol), and 10-undecenol (6 g, 35.4 mmol) were dissolved in 200 mL of anhydrous DCM; BF$_3$—OEt$_2$ (14.8 mL) was added dropwise in an ice bath; the reaction was maintained in an ice bath for 24 hours and the completion of the reaction was monitored by TLC. The reaction was filtered by diatomite; and the filtrate was dissolved in 500 mL of ethyl acetate and washed with 200 mL saturated sodium bicarbonate solution and 200 mL saturated brine successively. The organic phase was dried over anhydrous magnesium sulfate, concentrated under reduced pressure and passed through a silica gel column (petroleum ether:ethyl acetate V:V=3:2) to isolate 19.5 g of a white solid with a yield of 83.9%, MS(ESI), m/z:811.25 ([M+Na]$^+$).

(2) Synthesis of Compound A$_2$-I$_2$

Using compound 11 as a raw material, synthesis was performed with reference to A$_1$-I$_2$. The yield was 87%. $^1$HNMR (400 MHz, DMSO-d6) δ:11.82 (s, 1H), 5.86-5.73 (m, 1H), 5.22 (s, 1H), 5.2-4.9 (m, 6H), 4.5-4.98 (s, J=3.5 Hz, 2H), 4.08-3.99 (m, 3H), 3.9-3.88 (m, 2H), 3.73-3.65 (m, 2H), 3.48-3.38 (m, 1H), 2.12 (s, 6H), 2.05-2.01 (m, 2H), 2.00 (s, 6H), 1.88 (s, 6H), 1.66 (s, 3H), 1.5-1.4 (m, 2H), 1.39-1.3 (m, 2H), 1.29-1.19 (m, 8H). MS(ESI), m/z:829.7 ([M+Na]$^+$).

Example 8 Synthesis of Compounds A$_3$-I$_1$

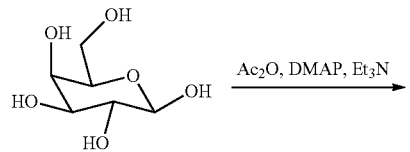

(1) Synthesis of Compound 12

Reference synthesis of compound 5, a white solid was obtained with a yield of 91%. $^1$HNMR (400 MHz, DMSO-d6) δ:5.63 (d, J=8.8 Hz, 1H), 5.26 (d, J=3.1 Hz, 1H), 5.05 (d, J=11.3, 3.3 Hz, 1H), 4.36 (m, 4H), 2.11 (s, 3H), 2.03 (s, 3H), 1.98 (s, 3H), 1.90 (s, 3H), 1.78 (s, 3H). MS(ESI), m/z:391.21 ([M+1]$^+$).

(2) Synthesis of Compound 13

The synthesis of compound 13 was with reference to the synthesis of compound 10 using compound 12 as the raw material. A clear oily liquid was obtained with a yield of 86%.

$^1$HNMR (400 MHz, DMSO-d6) δ:7.33-7.16 (m, 5H), 5.28 (d, J=5.3 Hz, 1H), 4.95 (s, 2H), 4.93 (q, J=4.2 Hz, 1H), 4.40 (d, J=8.6 Hz, 1H), 4.00-3.86 (m, 3H), 3.73-3.56 (m, 1H), 3.36-3.21 (m, 2H), 2.53 (t, J=8.2 Hz, 2H), 2.11 (s, 3H), 1.89

(s, 3H), 1.83 (s, 3H), 1.65 (s, 3H), 1.59-1.36 (m, 4H). MS(ESI), m/z:561.2 ([M+Na]⁺).

(3) Synthesis of Compound $A_3$-$I_1$

The synthesis of compound $A_3$-$I_1$ was with reference to the synthesis of compound $A_1$-$I_1$ using compound 13 as the raw material. A white solid was obtained with a yield of 93.5%. ¹HNMR (400 MHz, DMSO-d6) δ: 11.98 (s, 1H), 5.20 (s, 1H), 4.95 (q, J=4.2 Hz, 1H), 4.51 (d, J=7.2 Hz, 1H), 4.15-3.97 (m, 3H), 3.89-3.79 (m, 1H), 3.80-3.69 (m, 1H), 3.46-3.36 (m, 1H), 2.22-2.14 (t, J=7.2 Hz, 2H), 2.15 (s, 3H), 2.00 (s, 3H), 1.95 (s, 3H), 1.87 (s, 3H), 1.59-1.42 (m, 4H). MS(ESI), m/z:471.5 ([M+Na]⁺).

Example 9 Synthesis of Compounds $A_3$-$I_2$

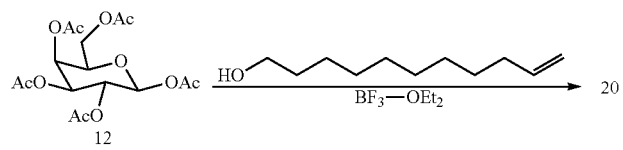

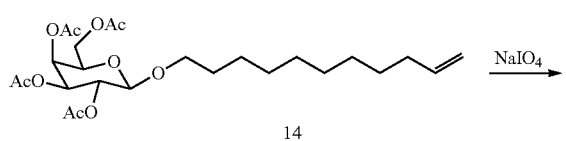

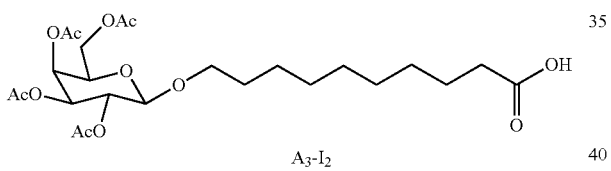

(1) Synthesis of Compound 14

The synthesis of compound 14 was with reference to the synthesis of compound 11 using compound 12 as the raw material. A white solid was obtained with a yield of 88%.

¹HNMR (400 MHz, DMSO-d6) δ:5.86-5.73 (m, 1H), 5.22 (s, 1H), 5.2-4.9 (m, 3H), 4.5-4.98 (s, J=3.5 Hz, 1H), 4.08-3.99 (m, 3H), 3.9-3.88 (m, 1H), 3.73-3.65 (m, 1H), 3.48-3.38 (m, 1H), 2.12 (s, 3H), 2.05-2.01 (m, 2H), 2.00 (s, 3H), 1.88 (s, 3H), 1.66 (s, 3H), 1.5-1.4 (m, 2H), 1.39-1.3 (m, 2H), 1.29-1.19 (m, 10H). MS(ESI), m/z:523.5 ([M+Na]⁺).

(2) Synthesis of Compounds $A_3$-$I_2$

The synthesis of compound $A_3$-$I_2$ was with reference to the synthesis of compound $A_1$-$I_2$ using compound 14 as the raw material. A light brown gummy product was obtained with a yield of 97%.

¹HNMR (400 MHz, DMSO-d6) δ:11.99 (s, 1H), 5.22 (s, 1H), 5.02-4.9 (m, 1H), 4.5-4.98 (s, J=3.5 Hz, 1H), 4.08-3.99 (m, 3H), 3.9-3.88 (m, 1H), 3.73-3.65 (m, 1H), 3.48-3.38 (m, 1H), 2.12 (s, 3H), 2.05-2.01 (m, 2H), 2.00 (s, 3H), 1.88 (s, 3H), 1.66 (s, 3H), 1.5-1.4 (m, 2H), 1.39-1.3 (m, 2H), 1.29-1.19 (m, 10H). MS(ESI), m/z:541.3 ([M+Na]⁺).

Example 10 Synthesis of Compounds $A_1$-$IV_1$

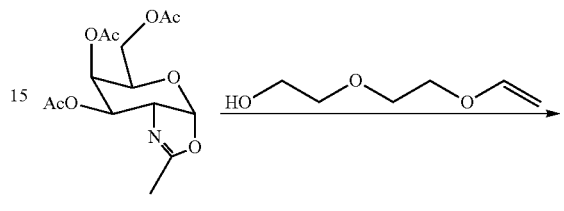

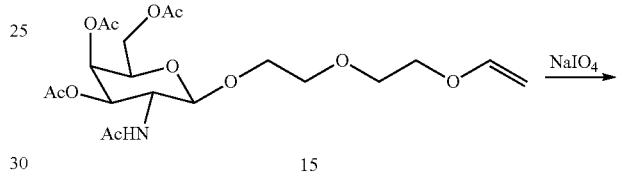

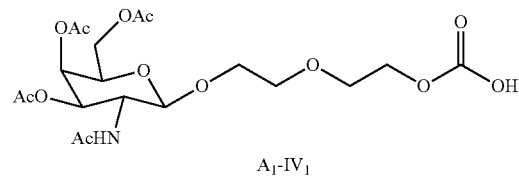

(1) Synthesis of Compound 15

The synthesis of compound 15 was with reference to the synthesis of compound 8 using compound 6 as the raw material. MS(ESI), m/z: 484.2 ([M+1]⁺).

(2) Synthesis of Compound $A_1$-$IV_1$

The synthesis of compound $A_1$-$IV_1$ was with reference to the synthesis of compound $A_1$-$I_2$ using compound 15 as the raw material. ¹HNMR (400 MHz, DMSO-d6) δ:11.88 (s, 1H), 7.77-7.73 (d, J=8.9 Hz, 1H), 5.21 (s, 1H), 5.0-4.96 (q, J=4.2 Hz, 1H), 4.45-4.51 (d, J=7.2 Hz, 1H), 4.12-4.07 (m, 3H), 3.88-3.78 (m, 1H), 3.72-3.68 (m, 2H), 3.62-3.58 (m, 2H), 3.56-3.46 (m, 4H), 2.15 (s, 3H), 2.00 (s, 3H), 1.95 (s, 3H), 1.87 (s, 3H). MS(ESI), m/z:502.6 ([M+1]⁺).

Example 11 Synthesis of Compound $A_1$-$I_1$-$R_1$

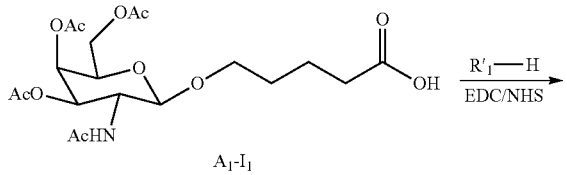

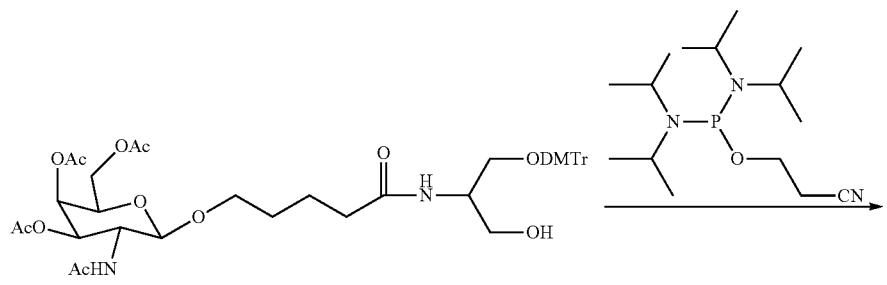

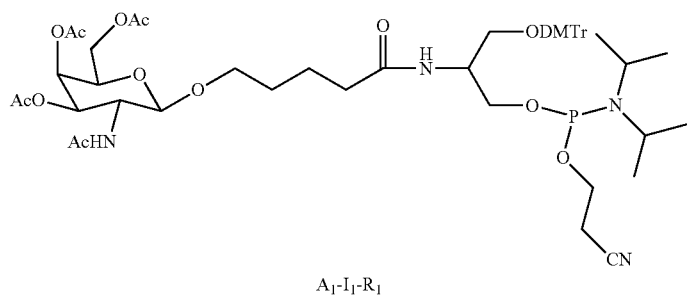

$A_1$-$I_1$-$R_1$ (1) Synthesis of Compound 16

In a 250 mL round bottom flask, compound $A_1$-$I_1$ (10 g, 22.35 mmol), 1-ethyl-(3-dimethylaminopropyl) carbonyldiimine hydrochloride (EDC. HCL) (5.14 g, 26.82 mmol), N-hydroxysuccinimide (2.83 g, 24.59 mmol), and dichloromethane 100 mL were added. After stirring for the reaction at room temperature for 0.5 h, compound $R_1$-H (8.79 g, 22.35 mmol) was added, and the reaction was monitored by TLC and was complete after 4 h. The reaction liquid was washed successively with 50 mL of saturated sodium bicarbonate solution and 50 mL of saturated brine, the organic phase was dried over anhydrous sodium sulfate, then concentrated, and passed through a silica gel column (dichloromethane:methanol V:V=20:1) to isolate 15.8 g of a white solid with a yield of 86%. MS (ESI), m/z:845.2 ([M+Na]$^+$).

(2) Synthesis of Compound $A_1$-$I_1$-$R_1$

In a 250 mL two-necked flask, compound 16 (5 g, 6.08 mmol) under nitrogen protection, 100 mL anhydrous acetonitrile, and bis (diisopropylamino)(2-cyanoethoxy) phosphine (3.66 g, 12.16 mmol) were added, and a solution of ethylthiotetrazole in acetonitrile (2.5M) (1.22 mL, 3.04 mmol) was slowly added dropwise with stirring for a reaction for 0.5 h; the reaction was monitored by TLC and was complete after 0.5 h. The reaction was concentrated under reduced pressure to remove acetonitrile, added with 100 mL of dichloromethane to be dissolved and washed with 100 mL of saturated brine. The organic phase was dried over anhydrous sodium sulfate, concentrated and passed through a silica gel column (petroleum ether:ethyl acetate V:V=1:3) to isolate 5.16 g of a white solid with a yield of 83%. $^1$H NMR (400 MHz, DMSO-d6) δ:7.84-7.79 (d, J=8.9 Hz, 1H), 7.65-7.60 (d, J=8.9 Hz, 1H), 7.41-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.20 (s, 1H), 5.0-4.95 (q, J=4.2 Hz, 1H), 4.51-4.46 (d, J=7.2 Hz, 1H), 4.15-4.06 (m, 3H), 4.05-3.96 (m, 1H), 3.84-3.80 (m, 2H), 3.89-3.79 (m, 1H), 3.74 (s, 6H), 3.71-3.69 (m, 1H), 3.46-3.36 (m, 1H), 3.04-2.99 (m, 2H), 2.95-2.90 (m, 2H), 2.88-2.84 (m, 2H), 2.59-2.54 (m, 21-1), 2.22-2.14 (t, J=7.2 Hz, 2H), 2.15 (s, 3H), 2.00 (s, 3H), 1.95 (s, 3H), 1.87 (s, 3H), 1.77 (s, 12H), 1.59-1.42 (m, 4H). MS(ESI), m/z:1045.5 ([M+Na]$^+$).

Example 12 Synthesis of Compound $A_1$-$I_1$-$R_2$

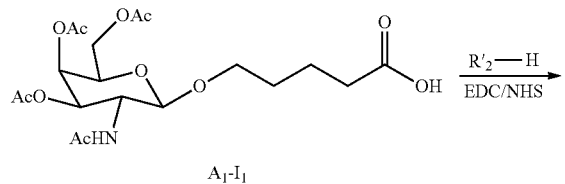

$A_1$-$I_1$

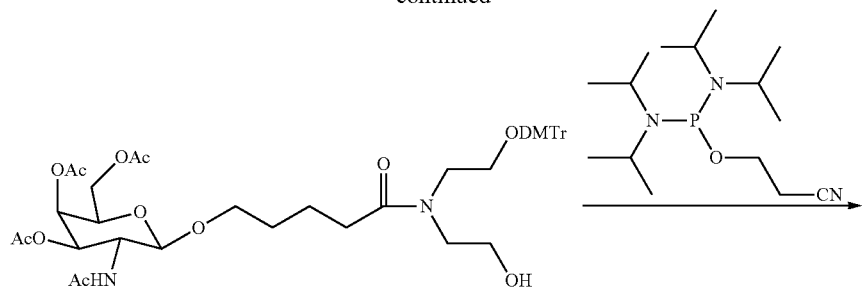

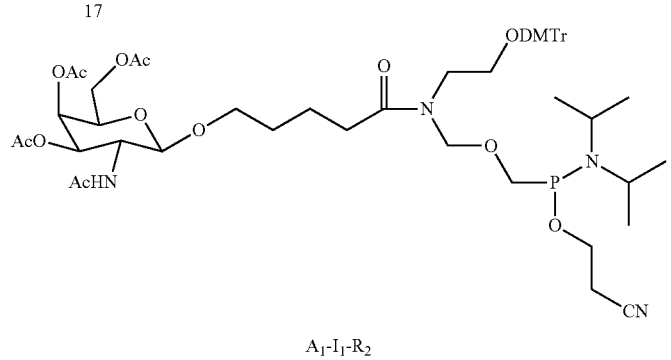

$A_1$-$I_1$-$R_2$ (1) Synthesis of Compound 17

The synthesis of compound 17 was with reference to the synthesis of compound 16 using compound $A_1$-$I_1$ as the raw material. A white solid was obtained with a yield of 82.5%. MS(ESI), m/z:859.2 ([M+Na]$^+$).

(2) Synthesis of Compound $A_1$-$I_1$-$R_2$

The synthesis of compound $A_1$-$I_1$-$R_2$ was with reference to the synthesis of compound $A_1$-$I_1$-$R_1$ using compound 17 as the raw material. A white solid was obtained with a yield of 84.2%. $1_H$ NMR (400 MHz, DMSO-d6) δ:7.83-7.79 (d, J=8.8 Hz, 1H), 7.42-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.20 (s, 1H), 5.0-4.95 (q, J=4.2 Hz, 1H), 4.51-4.46 (d, J=7.2 Hz, 1H), 4.15-3.97 (m, 3H), 4.05-3.96 (m, 1H), 3.84-3.80 (m, 2H), 3.89-3.79 (m, 1H), 3.74 (s, 6H), 3.71-3.69 (m, 1H), 3.46-3.36 (m, 1H), 3.04-2.99 (m, 2H), 2.98-2.95 (m, 2H), 2.89-2.93 (m, 4H), 2.88-2.84 (m, 2H), 2.60-2.55 (m, 2H), 2.22-2.14 (t, J=7.2 Hz, 2H), 2.15 (s, 3H), 2.00 (s, 3H), 1.95 (s, 3H), 1.87 (s, 3H), 1.77 (s, 12H), 1.59-1.42 (m, 4H). MS(ESI), m/z:1059.6 ([M+Na]$^+$).

Example 13 Synthesis of Compound $A_1$-$I_1$-$R_3$

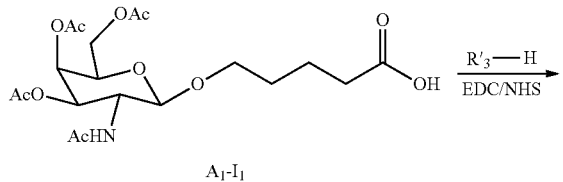

$A_1$-$I_1$

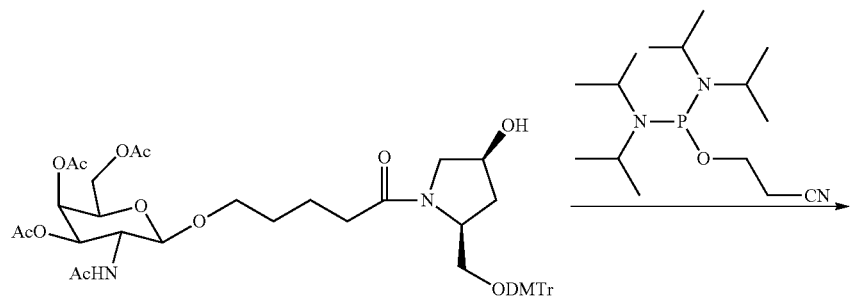

18

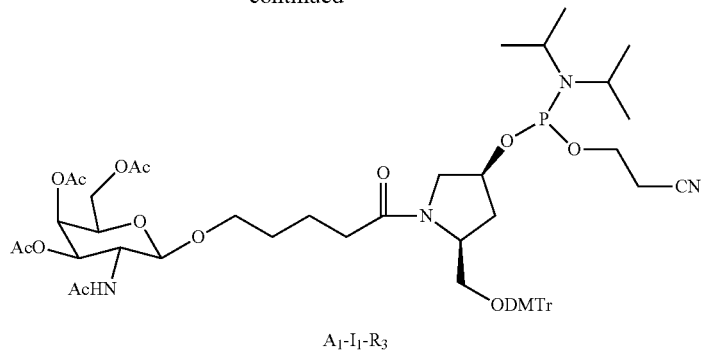

A₁-I₁-R₃

(1) Synthesis of Compound 18

The synthesis of compound 18 was with reference to the synthesis of compound 16 using compound A₁-I₁ as the raw material. A white solid was obtained with a yield of 86%. MS(ESI), m/z:871.2 ([M+Na]⁺).

(2) Synthesis of Compound A₁-I₁-R₃

The synthesis of compound A₁-I₁-R₃ was with reference to the synthesis of compound A1-I₁-R₁ using compound 18 as the raw material. A white solid was obtained with a yield of 84.2%.

¹HNMR (400 MHz, DMSO-d6) δ:7.73-7.70 (d, J=7.9 Hz, 1H), 7.42-7.37 (d, J=7.2 Hz, 2H), 7.35-7.29 (t, J=6.9 Hz, 2H), 7.28-7.19 (m, 5H), 6.92-6.86 (d, J=8.2 Hz, 4H), 5.20 (s, 1H), 5.0-4.95 (q, J=4.2 Hz, 1H), 4.51-4.46 (d, J=7.2 Hz, 1H), 4.15-3.97 (m, 3H), 3.89-3.79 (m, 3H), 3.74 (s, 6H), 3.70-3.67 (m, 1H), 3.46-3.36 (m, 1H), 3.05-2.99 (m, 3H), 2.90-2.86 (m, 3H), 2.77-2.71 (m, 1H), 2.60-2.55 (m, 2H), 2.22-2.14 (t, J=7.2 Hz, 2H), 2.15 (s, 3H), 2.00 (s, 3H), 1.95 (s, 3H), 1.87 (s, 3H), 1.88-1.81 (m, 2H), 1.77 (s, 12H), 1.59-1.42 (m, 4H). MS(ESI), m/z:1071.4 ([M+Na]⁺).

Example 14 Synthesis of Compound A₁-I₂-R₁

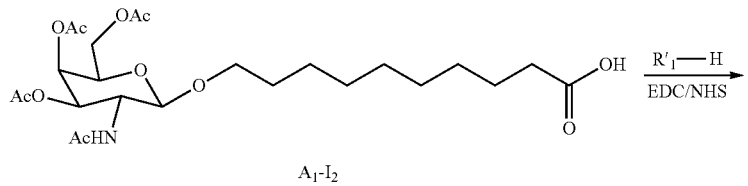

A₁-I₂

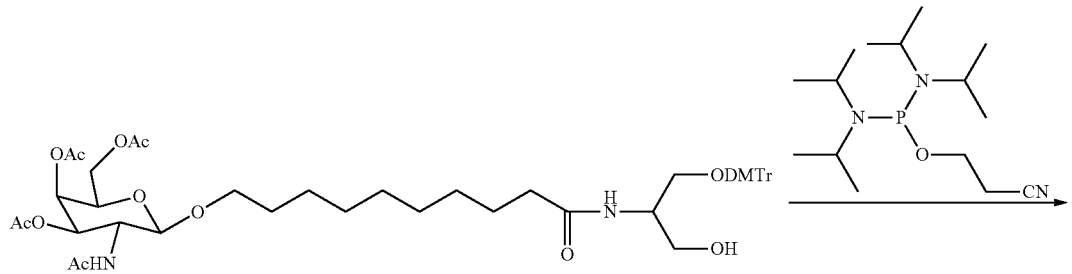

19

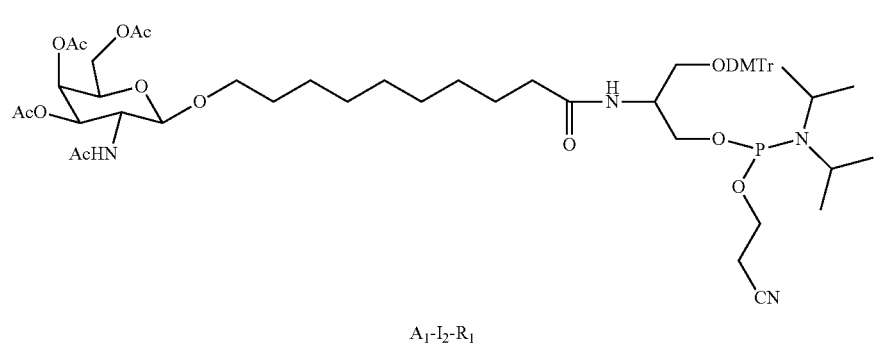

A₁-I₂-R₁

(1) Synthesis of Compound 19

The synthesis of Compound 19 was with reference to the synthesis of compound 16 using compound $A_1$-$I_2$ as the raw material. A white solid was obtained with a yield of 85.6%. MS(ESI), m/z:915.5 ([M+Na]$^+$).

(2) Synthesis of Compound $A_1$-$I_2$-$R_1$

The synthesis of compound $A_1$-$I_2$-$R_1$ was with reference to the synthesis of compound $A_1$-$I_1$-$R_1$ using compound 19 as the raw material. A white solid was obtained with a yield of 82.1%.

$^1$HNMR (400 MHz, DMSO-d6) δ:7.82-7.78 (d, J=7.3 Hz, 1H), 7.69-7.63 (d, J=7.3 Hz, 1H), 7.41-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.22 (s, 1H), 5.02-4.9 (m, 1H), 4.5-4.98 (s, J=3.5 Hz, 1H), 4.08-3.99 (m, 3H), 4.05-3.97 (m, 1H), 3.9-3.88 (m, 1H), 3.84-3.80 (m, 2H), 3.74 (s, 6H), 3.73-3.65 (m, 1H), 3.48-3.38 (m, 1H), 3.04-2.99 (m, 2H), 2.95-2.90 (m, 2H), 2.88-2.84 (m, 2H), 2.61-2.55 (m, 2H), 2.12 (s, 3H), 2.05-2.01 (m, 2H), 2.00 (s, 3H), 1.88 (s, 3H), 1.77 (s, 12H), 1.66 (s, 3H), 1.5-1.4 (m, 2H), 1.39-1.3 (m, 2H), 1.29-1.19 (m, 10H). MS(ESI), m/z:1115.2 ([M+Na]$^+$).

Example 15 Synthesis of Compound $A_1$-$I_2$-$R_2$ (1) Synthesis of Compound 20

The synthesis of compound 20 was with reference to the synthesis of compound 16 using compound $A_1$-$I_2$ as the raw material. A white solid was obtained with a yield of 84.2%. MS(ESI), m/z:929.3 ([M+Na]$^+$).

(2) Synthesis of Compound $A_1$-$I_2$-$R_2$

The synthesis of compound $A_1$-$I_2$-$R_2$ was with reference to the synthesis of compound $A_1$-$I_1$-$R_1$ using compound 20 as the raw material. A white solid was obtained with a yield of 81.1%. $^1$HNMR (400 MHz, DMSO-d6) δ:7.83-7.77 (d, J=7.3 Hz, 1H), 7.41-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.22 (s, 1H), 5.02-4.9 (m, 1H), 4.5-4.98 (s, J=3.5 Hz, 1H), 4.08-3.99 (m, 3H), 3.9-3.88 (m, 1H), 3.84-3.80 (m, 2H), 3.74 (s, 6H), 3.73-3.65 (m, 1H), 3.48-3.38 (m, 1H), 3.15-3.11 (m, 4H), 3.04-2.99 (m, 2H), 2.95-2.90 (m, 2H), 2.88-2.84 (m, 2H), 2.61-2.55 (m, 2H), 2.12 (s, 3H), 2.05-2.01 (m, 2H), 2.00 (s, 3H), 1.88 (s, 3H), 1.77 (s, 12H), 1.66 (s, 3H), 1.5-1.4 (m, 2H), 1.39-1.3 (m, 2H), 1.29-1.19 (m, 10H). MS(ESI), m/z:1129.4 ([M+Na]$^+$).

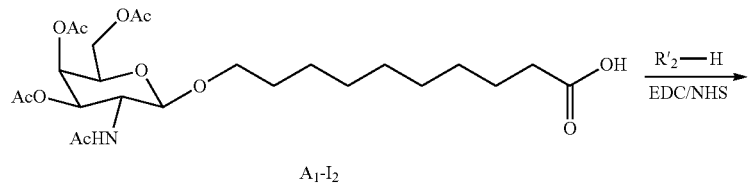

$A_1$-$I_2$

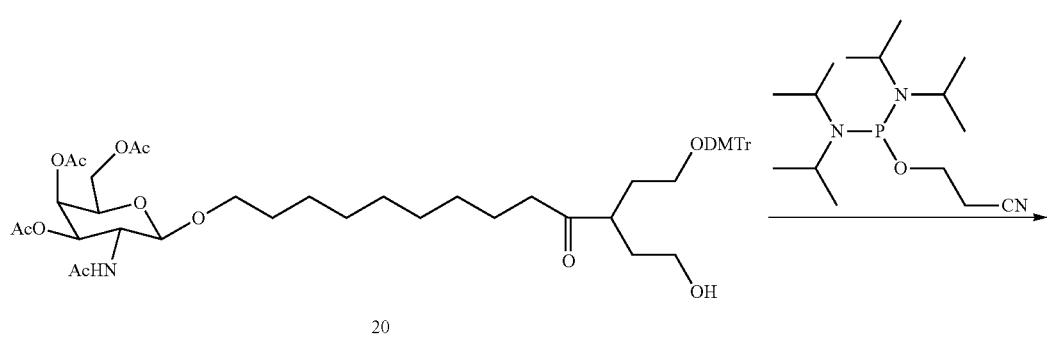

20

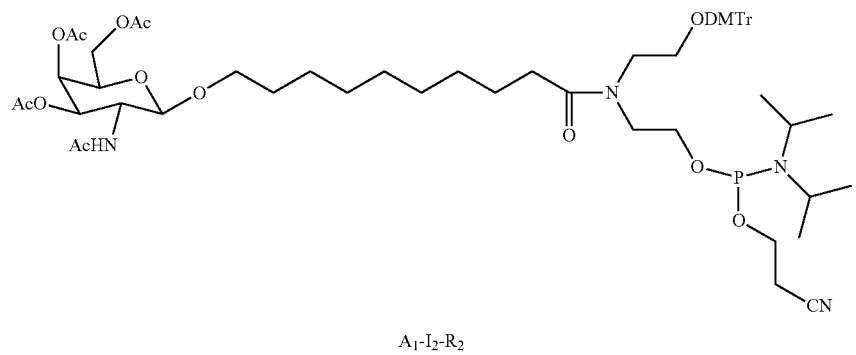

$A_1$-$I_2$-$R_2$

Example 16 Synthesis of Compound $A_1$-$I_2$-$R_3$

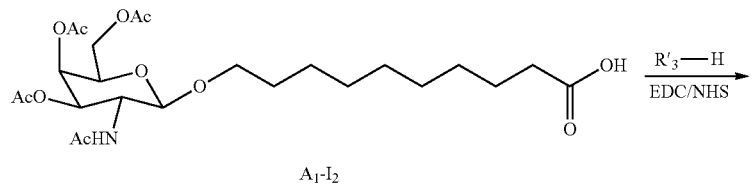

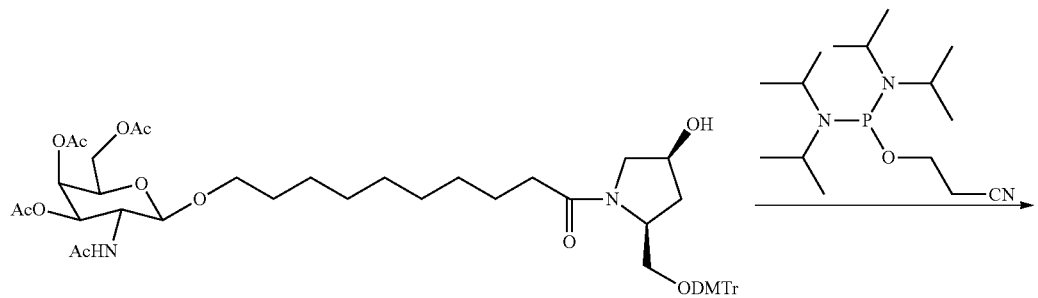

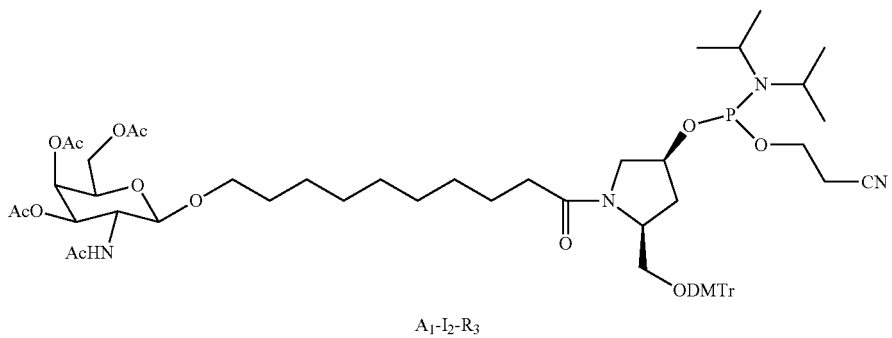

(1) Synthesis of Compound 21

The synthesis of compound 21 was with reference to the synthesis of compound 16 using compound $A_1$-$I_2$ as the raw material. A white solid was obtained with a yield of 80.5%. MS(ESI), m/Z:941.1 ([M+Na]$^+$).

(2) Synthesis of Compound $A_1$-$I_2$-$R_3$

The synthesis of compound $A_1$-$I_2$-$R_3$ was with reference to the synthesis of compound $A_1$-$I_1$-$R_1$ using compound 21 as the raw material. A white solid was obtained with a yield of 81.1% $^1$HNMR (400 MHz, DMSO-d6) δ:7.82 (d, J=3.3 Hz, 1H), 7.42-7.37 (d, J=7.2 Hz, 2H), 7.35-7.29 (t, J=6.9 Hz, 2H), 7.28-7.19 (m, 5H), 6.92-6.86 (d, J=8.2 Hz, 4H), 5.22 (s, 1H), 5.02-4.9 (m, 1H), 4.5-4.98 (s, J=3.5 Hz, 1H), 4.08-3.99 (m, 3H), 3.9-3.88 (m, 1H), 3.84-3.80 (m, 2H), 3.76 (s, 6H), 3.73-3.65 (m, 1H), 3.48-3.38 (m, 1H), 3.05-2.99 (m, 3H), 2.90-2.84 (m, 4H), 2.77-2.71 (m, 1H), 2.62-2.56 (m, 2H), 2.12 (s, 3H), 2.05-2.01 (m, 2H), 2.00 (s, 3H), 1.88 (s, 3H), 1.87-1.81 (m, 2H), 1.77 (s, 12H), 1.66 (s, 3H), 1.5-1.4 (m, 2H), 1.39-1.3 (m, 2H), 1.29-1.19 (m, 10H). MS(ESI), m/z: 1141.2 ([M+Na]$^+$).

Example 17 Synthesis of Compound $A_2$-$I_1$-$R_1$

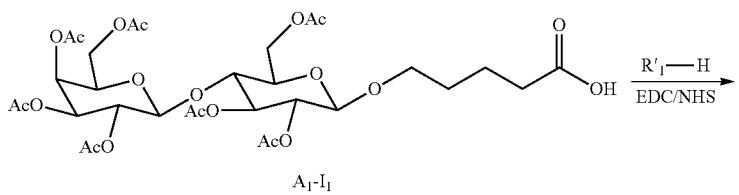

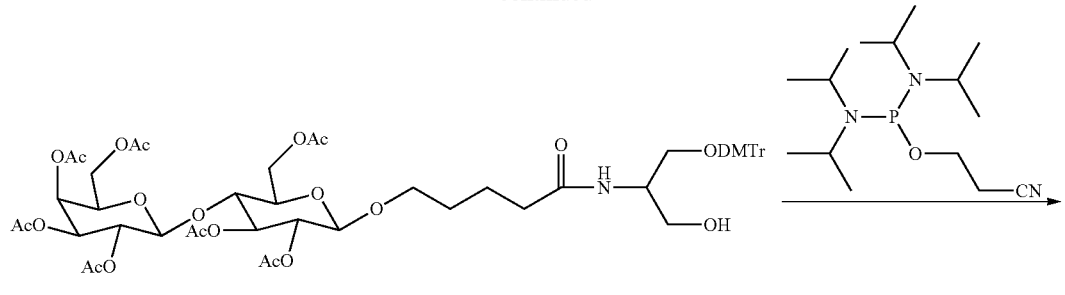

22

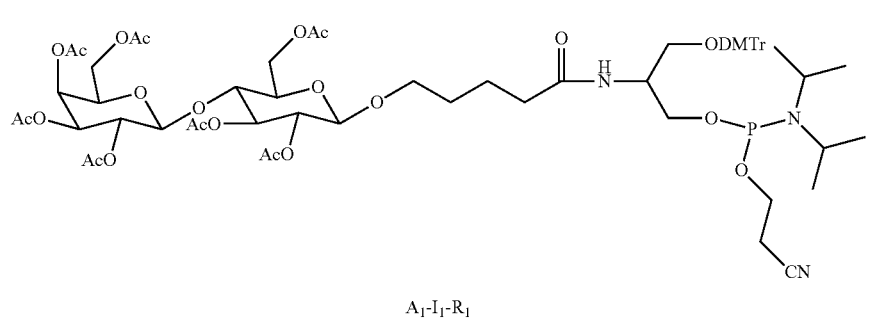

A₁-I₁-R₁

(1) Synthesis of Compound 22

The synthesis of compound 22 was with reference to the synthesis of compound 16 using compound A₂-I₁ as the raw material. A white solid was obtained with a yield of 80.4%. MS(ESI), m/z:1134.7 ([M+Na]⁺).

(2) Synthesis of Compound A₂-I₁-R₁

The synthesis of compound A₂-I₁-R₁ was with reference to the synthesis of compound A₁-I₁-R₁ using compound 22 as the raw material. A white solid was obtained with a yield of 81.3%. H NMR (400 MHz, DMSO-d6) δ:7.61-7.57 (d, J=7.2 Hz, 1H), 7.41-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.20 (s, 2H), 4.95 (q, J=4.2 Hz, 2H), 4.51 (d, J=7.2 Hz, 1H), 4.46 (d, J=7.2 Hz, 1H), 4.15-3.97 (m, 6H), 4.05-3.97 (m, 1H), 3.89-3.79 (m, 4H), 3.75 (s, 6H), 3.80-3.69 (m, 1H), 3.46-3.36 (m, 1H), 3.04-2.99 (m, 2H), 2.95-2.90 (m, 2H), 2.88-2.84 (m, 2H), 2.61-2.55 (m, 2H), 2.22-2.14 (t, J=7.2 Hz, 2H), 2.15 (s, 6H), 2.00 (s, 6H), 1.95 (s, 6H), 1.87 (s, 3H), 1.77 (s, 12H), 1.59-1.42 (m, 4H). MS(ESI), m/z:1334.2 ([M+Na]⁺).

Example 18 Synthesis of Compound A₂-I₁-R₂

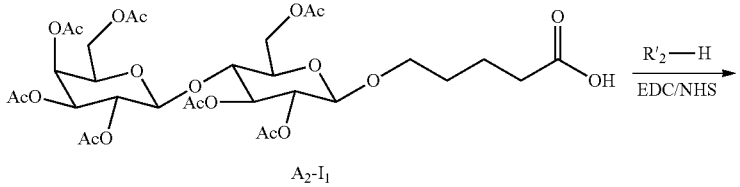

A₂-I₁

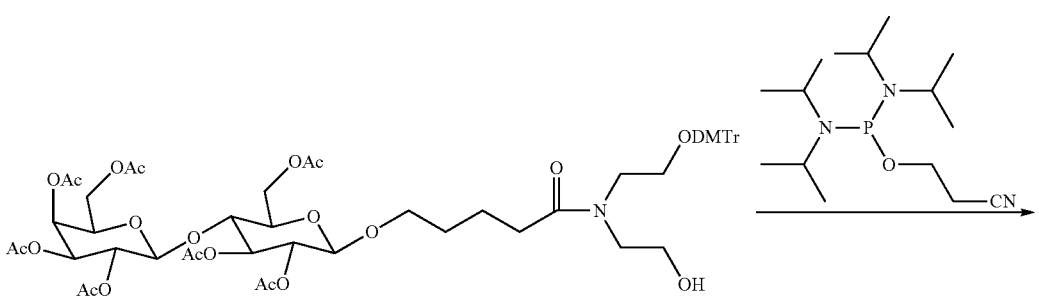

23

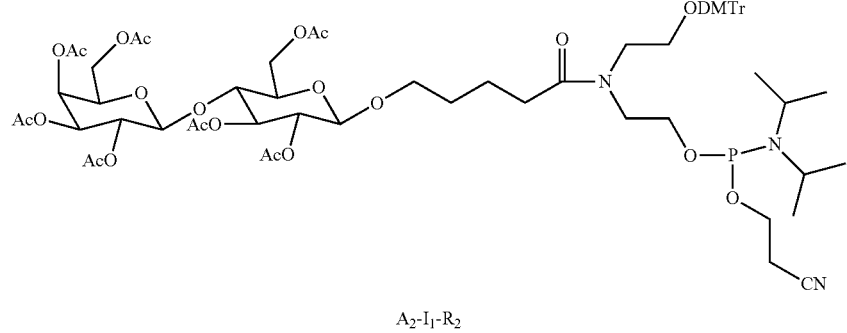

$A_2$-$I_1$-$R_2$ (1) Synthesis of Compound 23

The synthesis of compound 23 was with reference to the synthesis of compound 16 using compound $A_2$-$I_1$ as the raw material. A white solid was obtained with a yield of 86.1%. MS(ESI), m/z:1148.3 ([M+Na]$^+$).

(2) Synthesis of Compound $A_2$-$I_1$-$R_2$

The synthesis of compound $A_2$-$I_1$-$R_2$ was with reference to the synthesis of compound $A_1$-$I_1$-$R_1$ using compound 23 as the raw material. A white solid was obtained with a yield of 82.3%. H NMR (400M Hz, DMSO-d6) δ:7.40-7.36 (d, J=7.2 Hz, 2H), 7.33-7.28 (t, J=6.9 Hz, 2H), 7.27-7.19 (m, 5H), 6.91-6.86 (d, J=8.2 Hz, 4H), 5.20 (s, 2H), 4.95 (q, J=4.2 Hz, 2H), 4.51 (d, J=7.2 Hz, 1H), 4.46 (d, J=7.2 Hz, 1H), 4.15-3.97 (m, 6H), 3.89-3.79 (m, 4H), 3.75 (s, 6H), 3.80-3.69 (m, 1H), 3.46-3.41 (m, 4H), 3.46-3.36 (m, 1H), 3.04-2.99 (m, 2H), 2.95-2.90 (m, 2H), 2.88-2.84 (m, 2H), 2.61-2.55 (m, 2H), 2.22-2.14 (t, J=7.2 Hz, 2H), 2.15 (s, 6H), 2.00 (s, 6H), 1.95 (s, 6H), 1.87 (s, 3H), 1.77 (s, 12H), 1.59-1.42 (m, 4H). MS(ESI), m/z:1348.2 ([M+Na]$^+$).

Example 19 Synthesis of Compound $A_2$-$I_1$-$R_3$

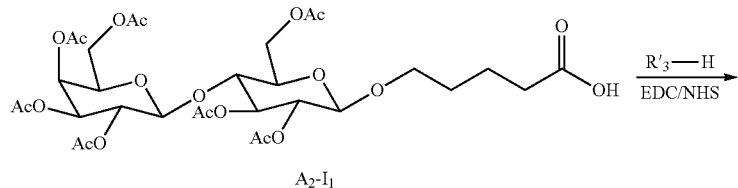

$A_2$-$I_1$

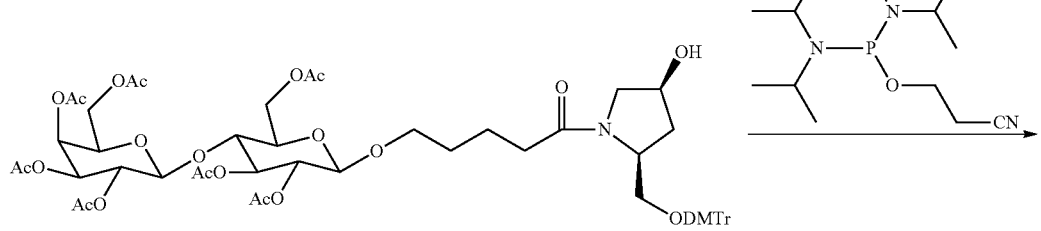

24

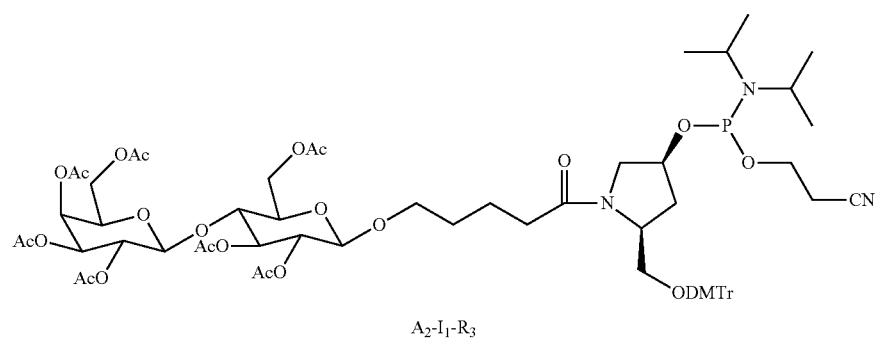

$A_2$-$I_1$-$R_3$ (1) Synthesis of Compound 24

The synthesis of compound 24 was with reference to the synthesis of compound 16 using compound $A_2$-$I_1$ as the raw material. A white solid was obtained with a yield of 82.9%. MS(ESI), m/z:1160.5 ([M+Na]$^+$).

(2) Synthesis of Compound $A_2$-$I_1$-$R_3$

The synthesis of compound $A_2$-$I_1$-$R_3$ was with reference to the synthesis of compound $A_1$-$I_1$-$R_1$ using compound 24 as the raw material. A white solid was obtained with a yield of 82.3%. H NMR (400 MHz, DMSO-d6) δ:7.44-7.39 (d, J=7.2 Hz, 2H), 7.36-7.30 (t, J=6.9 Hz, 2H), 7.28-7.19 (m, 5H), 6.92-6.86 (d, J=8.2 Hz, 4H), 5.20 (s, 2H), 4.95 (q, J=4.2 Hz, 2H), 4.51 (d, J=7.2 Hz, 1H), 4.46 (d, J=7.2 Hz, 1H), 4.15-3.97 (m, 6H), 3.89-3.82 (m, 4H), 3.80-3.76 (m, 1H), 3.74 (s, 6H), 3.46-3.36 (m, 1H), 3.05-2.99 (m, 3H), 2.90-2.86 (m, 2H), 2.77-2.71 (m, 1H), 2.61-2.56 (m, 2H, 2.22-2.14 (t, J=7.2 Hz, 2H), 2.15 (s, 6H), 2.00 (s, 6H), 1.95 (s, 6H), 1.87 (s, 3H), 1.86-1.81 (m, 2H), 1.77 (s, 12H), 1.59-1.42 (m, 4H). MS(ESI), m/z:1360.26 ([M+Na]$^+$).

Example 20 Synthesis of Compound $A_2$-$I_2$-$R_1$ (1) Synthesis of Compound 25

The synthesis of compound 25 was with reference to the synthesis of compound 16 using compound $A_2$-$I_2$ as the raw material. A white solid was obtained with a yield of 86.3%. MS(ESI), m/z:1204.6 ([M+Na]$^+$).

(2) Synthesis of Compound $A_2$-$I_2$-$R_1$

The synthesis of compound $A_2$-$I_2$-$R_1$ was with reference to the synthesis of compound $A_1$-$I_1$-$R_1$ using compound 25 as the raw material. A white solid was obtained with a yield of 80.3%. $^1$H NMR (400 MHz, DMSO-d6) δ:7.71-7.66 (d, J=7.2 Hz, 1H), 7.41-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.86-5.73 (m, 1H), 5.22 (s, 1H), 5.2-4.9 (m, 6H), 4.5-4.98 (s, J=3.5 Hz, 2H), 4.08-3.99 (m, 4H), 3.9-3.88 (m, 2H), 3.84-3.80 (m, 2H), 3.75 (s, 6H), 3.73-3.65 (m, 2H), 3.48-3.38 (m, 1H), 3.04-2.99 (m, 2H), 2.95-2.90 (m, 2H), 2.88-2.84 (m, 2H), 2.59-2.55 (m, 2H), 2.12 (s, 6H), 2.05-2.01 (m, 2H), 2.00 (s, 6H), 1.88 (s, 6H), 1.77 (s, 12H), 1.66 (s, 3H), 1.5-1.4 (m, 2H), 1.39-1.3 (m, 2H), 1.29-1.19 (m, 8H). MS(ESI), m/z:1404.7 ([M+Na]$^+$).

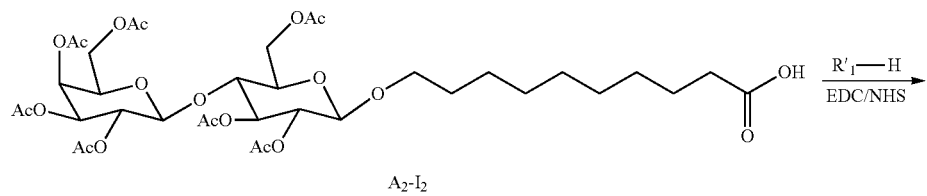

$A_2$-$I_2$

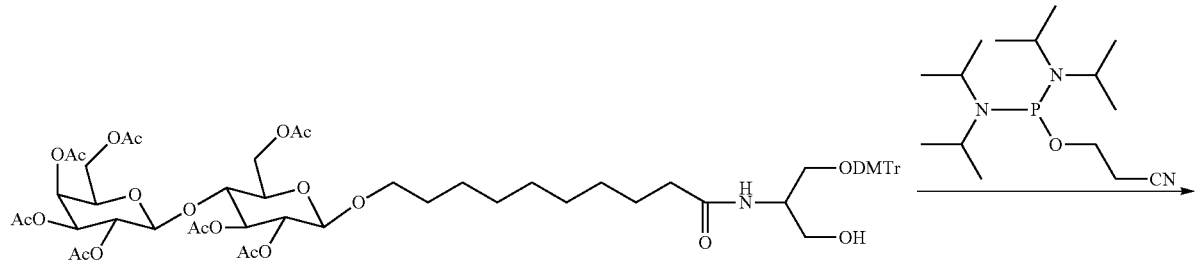

25

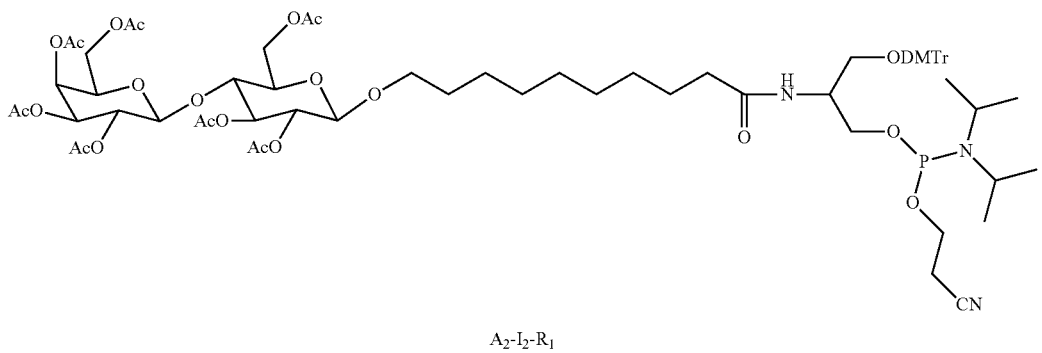

$A_2$-$I_2$-$R_1$

Example 21 Synthesis of Compound A$_2$-I$_2$-R$_2$

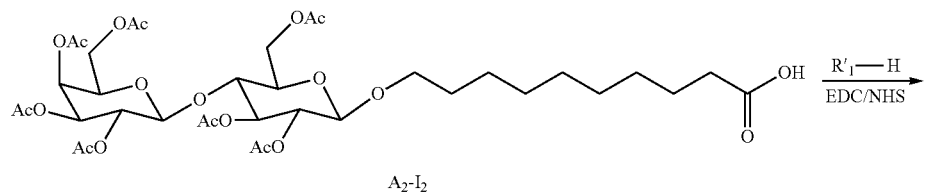

A$_2$-I$_2$

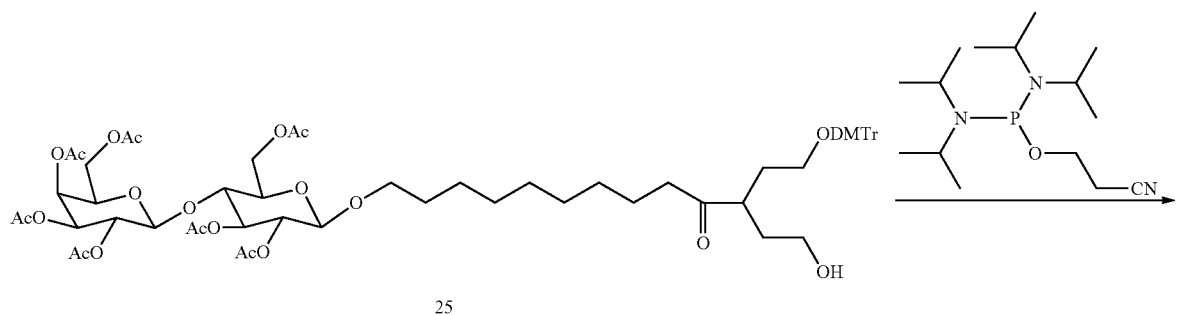

25

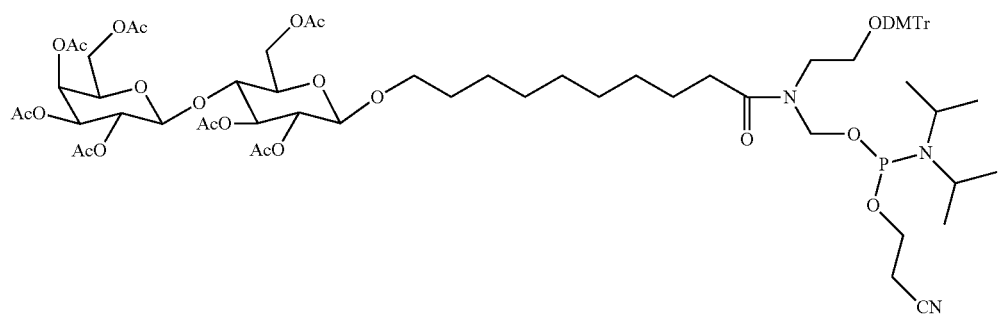

A$_2$-I$_2$-R$_2$

45

(1) Synthesis of Compound 26

The synthesis of compound 26 was with reference to the synthesis of compound 16 using compound A$_2$-I$_2$ as the raw material. A white solid was obtained with a yield of 87.3%. MS(ESI), m/z:1218.4 ([M+Na]$^+$).

(2) Synthesis of Compound A$_2$-I$_2$-R$_2$

The synthesis of compound A$_2$-I$_2$-R$_2$ was with reference to the synthesis of compound A$_1$-I$_1$-R$_1$ using compound 26 as the raw material. A white solid was obtained with a yield of 84.3%. $^1$H NMR (400 MHz, DMSO-d6) δ:7.41-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.86-5.73 (m, 1H), 5.22 (s, 1H), 5.2-4.9 (m, 6H), 4.5-4.98 (s, J=3.5 Hz, 2H), 3.9-3.88 (m, 2H), 3.84-3.80 (m, 2H), 3.75 (s, 6H), 3.73-3.65 (m, 2H), 3.48-3.38 (m, 1H), 3.3.16-3.12 (m, 4H), 3.04-2.99 (m, 2H), 2.95-2.90 (m, 2H), 2.88-2.84 (m, 2H), 2.59-2.55 (m, 2H), 2.12 (s, 6H), 2.05-2.01 (m, 2H), 2.00 (s, 6H), 1.88 (s, 6H), 1.77 (s, 12H), 1.66 (s, 3H), 1.5-1.4 (m, 2H), 1.39-1.3 (m, 2H), 1.29-1.19 (m, 8H). MS(ESI), m/z:1418.7 ([M+Na]$^+$).

Example 22 Synthesis of Compound A$_2$-I$_2$-R$_3$

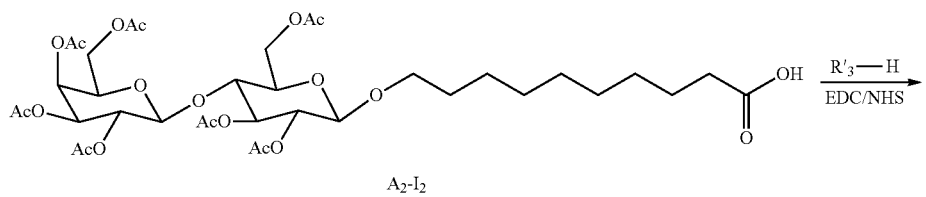

A$_2$-I$_2$

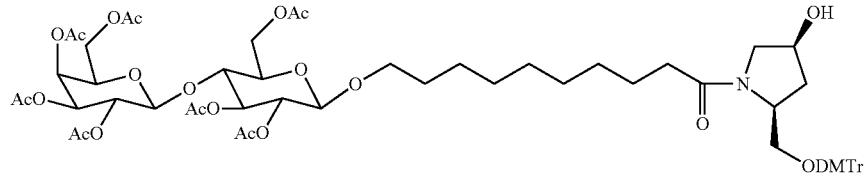
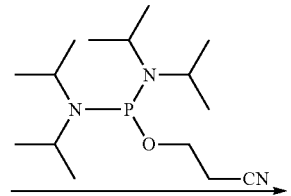

27

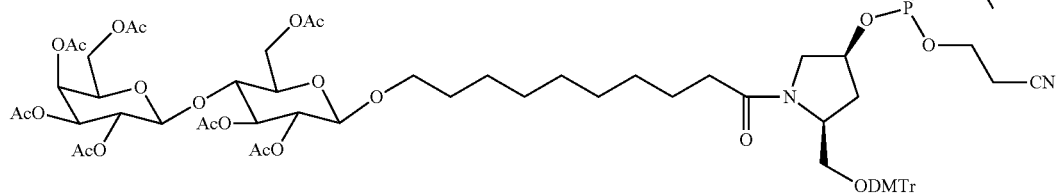

A₂-I₂-R₃

30

(1) Synthesis of Compound 27

The synthesis of compound 27 was with reference to the synthesis of compound 16 using compound A₂-I₂ as the raw material. A white solid was obtained with a yield of 88.0%. MS(ESI), m/z:1230.2 ([M+Na]⁺).

(2) Synthesis of Compound A₂-I₂-R₃

The synthesis of compound A₂-I₂-R₃ was with reference to the synthesis of compound A₁-I₁-R₁ using compound 27 as the raw material. A white solid was obtained with a yield of 87.0%. ¹HNMR (400 MHz, DMSO-d6) δ:7.42-7.37 (d, J=7.2 Hz, 2H), 7.35-7.29 (t, J=6.9 Hz, 2H), 7.28-7.19 (m, 5H), 6.92-6.86 (d, J=8.2 Hz, 4H), 5.86-5.73 (m, 1H), 5.22 (s, 1H), 5.2-4.9 (m, 6H), 4.5-4.98 (s, J=3.5 Hz, 2H), 4.08-3.99 (m, 3H), 3.9-3.88 (m, 2H), 3.84-3.80 (m, 2H), 3.74 (s, 6H), 3.73-3.65 (m, 2H), 3.48-3.38 (m, 1H), 3.05-2.99 (m, 3H), 2.90-2.86 (m, 4H), 2.77-2.71 (m, 1H), 2.60-2.56 (m, 2H), 2.12 (s, 6H), 2.05-2.01 (m, 2H), 2.00 (s, 6H), 1.88 (s, 6H), 1.86-1.81 (m, 2H), 1.77 (s, 12H), 1.66 (s, 3H), 1.5-1.4 (m, 2H), 1.39-1.3 (m, 2H), 1.29-1.19 (m, 8H). MS(ESI), m/z: 1430.2 ([M+Na]⁺).

Example 23 Synthesis of Compound A₃-I₁-R₁

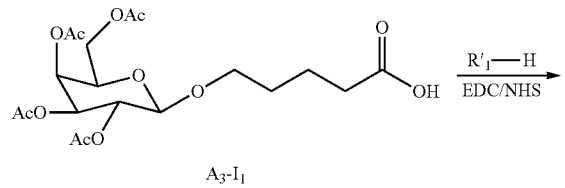

A₃-I₁

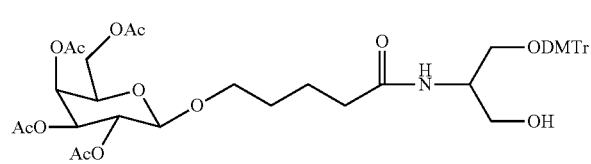
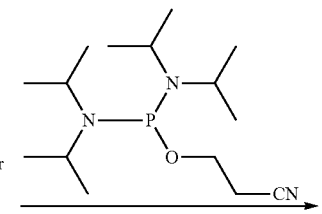

28

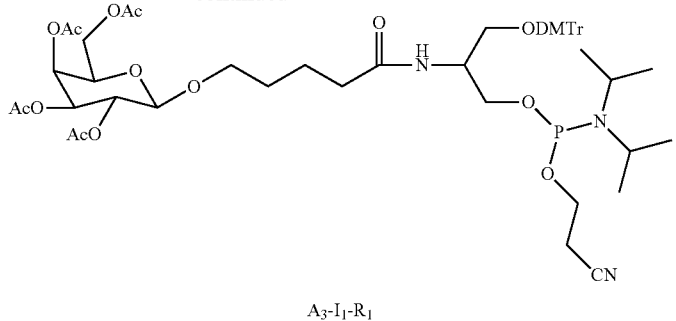

A₃-I₁-R₁

(1) Synthesis of Compound 28

The synthesis of compound 28 was with reference to the synthesis of compound 16 using compound A₃-I₁ as the raw material. A white solid was obtained with a yield of 88.2%. MS(ESI), m/z:846.3 ([M+Na]⁺).

(2) Synthesis of Compound A₃-I₁-R₁

The synthesis of compound A₃-I₁-R₁ was with reference to the synthesis of compound A₁-I₁-R₁ using compound 28 as the raw material. A white solid was obtained with a yield of 84.2%. ¹HNMR (400 MHz, DMSO-d6) δ:7.61-7.56 (d, J=7.2 Hz, 1H), 7.41-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.20 (s, 1H), 4.95 (q, J=4.2 Hz, 1H), 4.51 (d, J=7.2 Hz, 1H), 4.15-3.97 (m, 4H), 3.89-3.79 (m, 3H), 3.75 (s, 6H), 3.73-3.69 (m, 1H), 3.46-3.36 (m, 1H), 3.04-2.99 (m, 2H), 2.95-2.90 (m, 2H), 2.88-2.84 (m, 2H), 2.59-2.54 (m, 2H), 2.22-2.14 (t, J=7.2 Hz, 2H), 2.15 (s, 3H), 2.00 (s, 3H), 1.95 (s, 3H), 1.87 (s, 3H), 1.77 (s, 12H), 1.59-1.42 (m, 4H). MS(ESI), m/z:1046.5 ([M+Na]⁺).

Example 24 Synthesis of Compound A₃-I₁-R₂

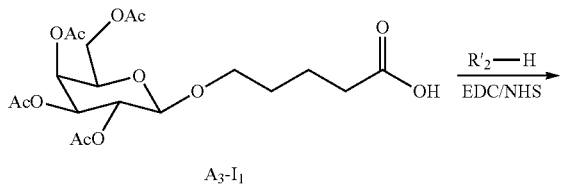

A₃-I₁

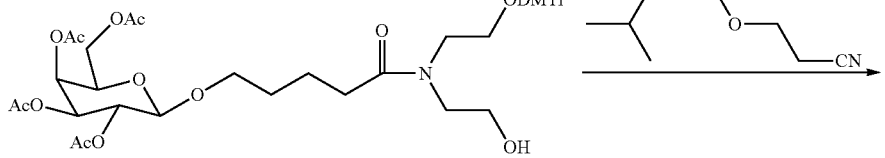

29

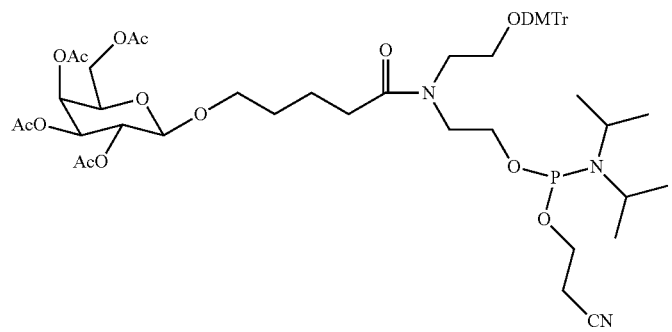

A₃-I₁-R₂

(1) Synthesis of Compound 29

The synthesis of compound 29 was with reference to the synthesis of compound 16 using compound $A_3$-$I_1$ as the raw material. A white solid was obtained with a yield of 88.9%. MS(ESI), m/z:860.3 ([M+Na]$^+$).

(2) Synthesis of Compound $A_3$-$I_1$-$R_2$

The synthesis of compound $A_3$-$I_1$-$R_2$ was with reference to the synthesis of compound $A_1$-$I_1$-$R_1$ using compound 29 as the raw material. A white solid was obtained with a yield of 84.7%. $^1$H NMR (400 MHz, DMSO-d6) δ:7.41-7.37 (d, J=7.2 Hz, 2H), 7.33-7.28 (t, J=6.9 Hz, 2H), 7.27-7.19 (m, 5H), 6.91-6.86 (d, J=8.2 Hz, 4H), 5.20 (s, 1H), 4.95 (q, J=4.2 Hz, 1H), 4.51 (d, J=7.2 Hz, 1H), 3.89-3.79 (m, 3H), 3.75 (s, 6H), 3.73-3.69 (m, 1H), 3.46-3.36 (m, 1H), 3.04-2.99 (m, 2H), 2.95-2.90 (m, 2H), 2.88-2.84 (m, 2H), 2.82-2.78 (m, 4H), 2.59-2.54 (m, 2H), 2.22-2.14 (t, J=7.2 Hz, 2H), 2.15 (s, 3H), 2.00 (s, 3H), 1.95 (s, 3H), 1.87 (s, 3H), 1.77 (s, 12H), 1.59-1.42 (m, 4H). MS(ESI), m/z:1060.5 ([M+Na]$^+$).

Example 25 Synthesis of Compound $A_3$-$I_1$-$R_3$ (1) Synthesis of Compound 30

The synthesis of compound 30 was with reference to the synthesis of compound 16 using compound $A_3$-$I_1$ as the raw material. A white solid was obtained with a yield of 84.3%. MS(ESI), m/z:872.7 ([M+Na]$^+$).

(2) Synthesis of Compound $A_3$-$I_1$-$R_3$

The synthesis of compound $A_3$-$I_1$-$R_3$ was with reference to the synthesis of compound $A_1$-$I_1$-$R_1$ using compound 30 as the raw material. A white solid was obtained with a yield of 86.2%. $^1$H NMR (400 MHz, DMSO-d6) δ:7.46-7.39 (d, J=7.2 Hz, 2H), 7.37-7.31 (t, J=6.9 Hz, 2H), 7.28-7.19 (m, 5H), 6.92-6.86 (d, J=8.2 Hz, 4H), 5.20 (s, 1H), 4.95 (q, J=4.2 Hz, 1H), 4.51 (d, J=7.2 Hz, 1H), 4.15-3.97 (m, 3H), 3.89-3.79 (m, 3H), 3.76 (s, 6H), 3.72-3.68 (m, 1H), 3.46-3.36 (m, 1H), 3.05-2.99 (m, 3H), 2.90-2.86 (m, 2H), 2.88-2.84 (m, 2H), 2.77-2.71 (m, 1H), 2.59-2.54 (m, 2H), 2.22-2.14 (t, J=7.2 Hz, 2H), 2.15 (s, 3H), 2.00 (s, 3H), 1.95 (s, 3H), 1.87 (s, 3H), 1.86-1.81 (m, 2H), 1.77 (s, 12H), 1.59-1.42 (m, 4H). MS(ESI), m/z:1072.8 ([M+Na]$^+$).

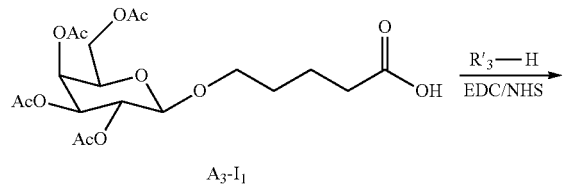

$A_3$-$I_1$

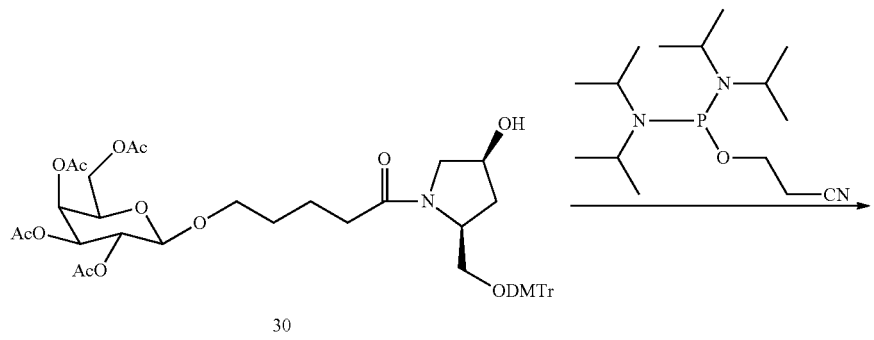

30

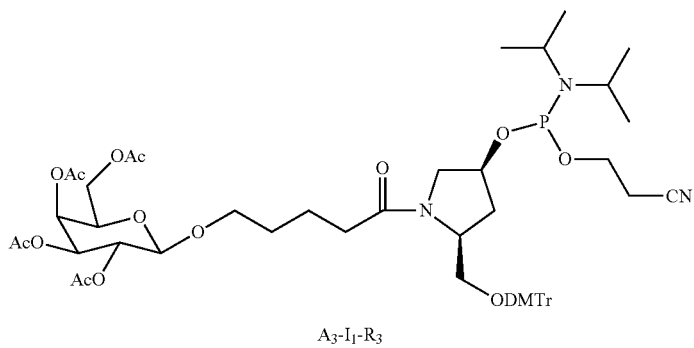

$A_3$-$I_1$-$R_3$

Example 26 Synthesis of Compound $A_3$-$I_2$-$R_1$

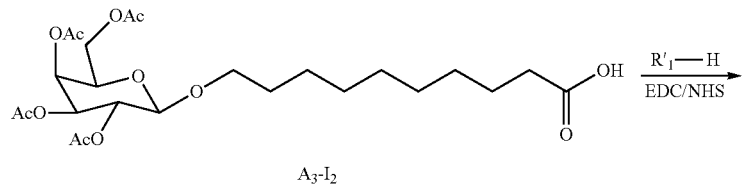

$A_3$-$I_2$

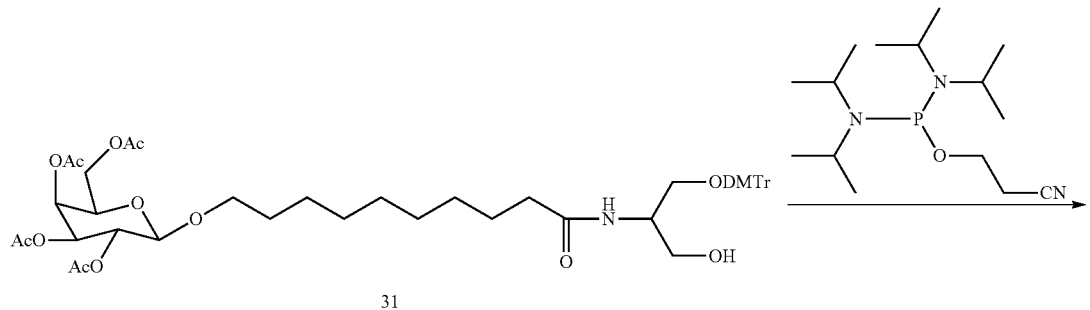

31

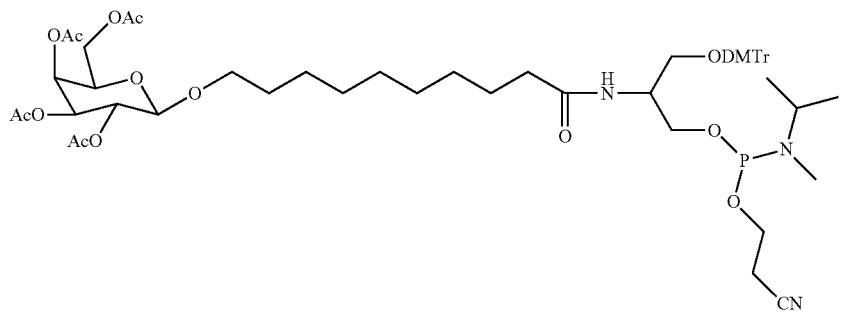

$A_3$-$I_2$-$R_1$ (1) Synthesis of Compound 31

The synthesis of compound 31 was with reference to the synthesis of compound 16 using compound $A_3$-$I_2$ as the raw material. A white solid was obtained with a yield of 86.2%. MS(ESI), m/z:916.4 ([M+Na]$^+$).

(2) Synthesis of Compound $A_3$-$I_2$-$R_1$

The synthesis of compound $A_3$-$I_2$-$R_1$ was with reference to the synthesis of compound $A_1$-$I_1$-$R_1$ using compound 31 as the raw material. A white solid was obtained with a yield of 85.1%. $^1$H NMR (400 MHz, DMSO-d6) δ:7.75-7.71 (d, J=7.2 Hz, 1H), 7.42-7.39 (d, J=7.2 Hz, 2H), 7.32-7.28 (t, J=6.9 Hz, 2H), 7.27-7.19 (m, 5H), 6.91-6.86 (d, J=8.2 Hz, 4H), 5.22 (s, 1H), 5.02-4.9 (m, 1H), 4.5-4.98 (s, J=3.5 Hz, 1H), 4.05-3.99 (m, 4H), 3.9-3.88 (m, 1H), 3.84-3.80 (m, 2H), 3.76 (s, 6H), 3.73-3.65 (m, 1H), 3.48-3.38 (m, 1H), 3.04-2.99 (m, 2H), 2.95-2.90 (m, 2H), 2.87-2.84 (m, 2H), 2.58-2.54 (m, 2H), 2.12 (s, 3H), 2.05-2.01 (m, 2H), 2.00 (s, 3H), 1.88 (s, 3H), 1.77 (s, 12H), 1.66 (s, 3H), 1.5-1.4 (m, 2H), 1.39-1.3 (m, 2H), 1.29-1.19 (m, 10H). MS(ESI), m/z: 1116.6 ([M+Na]$^+$).

Example 27 Synthesis of Compound $A_3$-$I_2$-$R_2$

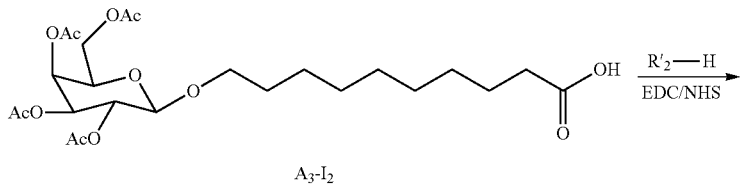

$A_3$-$I_2$

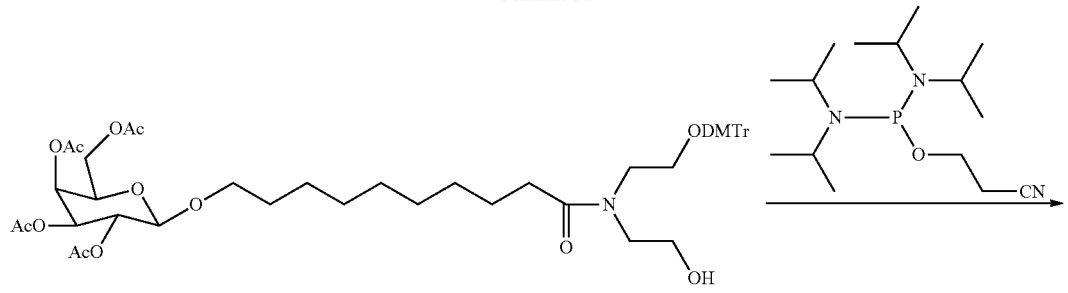

32

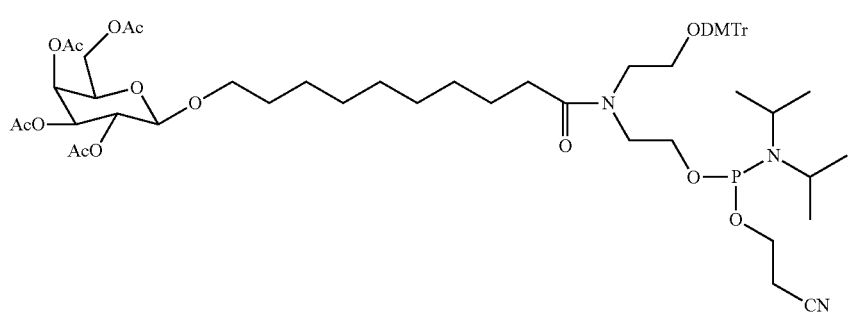

$A_3-I_2-R_2$

30

(1) Synthesis of Compound 32

The synthesis of compound 32 was with reference to the synthesis of compound 16 using compound $A_3-I_2$ as the raw material. A white solid was obtained with a yield of 82.9%. MS(ESI), m/z:930.7 ([M+Na]$^+$).

(2) Synthesis of Compound $A_3-I_2-R_2$

The synthesis of compound $A_3-I_2-R_2$ was with reference to the synthesis of compound $A_1-I_1-R_1$ using compound 32 as the raw material. A white solid was obtained with a yield of 84.3%. $^1$H NMR (400M Hz, DMSO-d6) δ:7.44-7.39 (d, J=7.2 Hz, 2H), 7.32-7.28 (t, J=6.9 Hz, 2H), 7.27-7.19 (m, 5H), 6.91-6.86 (d, J=8.2 Hz, 4H), 5.22 (s, 1H), 5.02-4.9 (m, 1H), 4.5-4.98 (s, J=3.5 Hz, 1H), 3.9-3.88 (m, 1H), 3.84-3.80 (m, 2H), 3.76 (s, 6H), 3.73-3.65 (m, 1H), 3.48-3.38 (m, 1H), 3.04-2.99 (m, 2H), 2.97-2.94 (m, 2H), 2.93-2.88 (m, 4H), 2.87-2.84 (m, 2H), 2.58-2.54 (m, 2H), 2.12 (s, 3H), 2.05-2.01 (m, 2H), 2.00 (s, 3H), 1.88 (s, 3H), 1.77 (s, 12H), 1.66 (s, 3H), 1.5-1.4 (m, 2H), 1.39-1.3 (m, 2H), 1.29-1.19 (m, 10H). MS(ESI), m/z:1130.6 ([M+Na]$^+$).

Example 28 Synthesis of Compound $A_3-I_2-R_3$

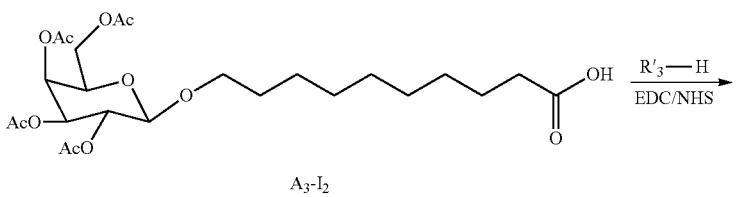

$A_3-I_2$

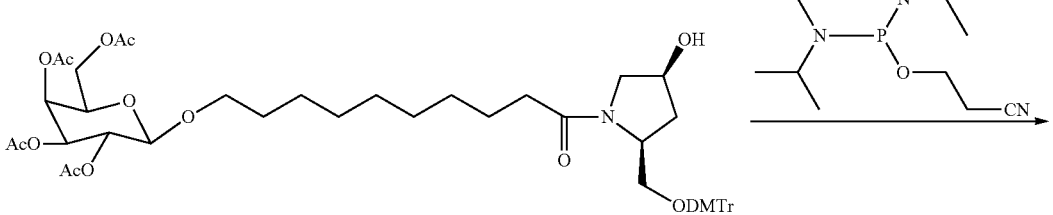

33

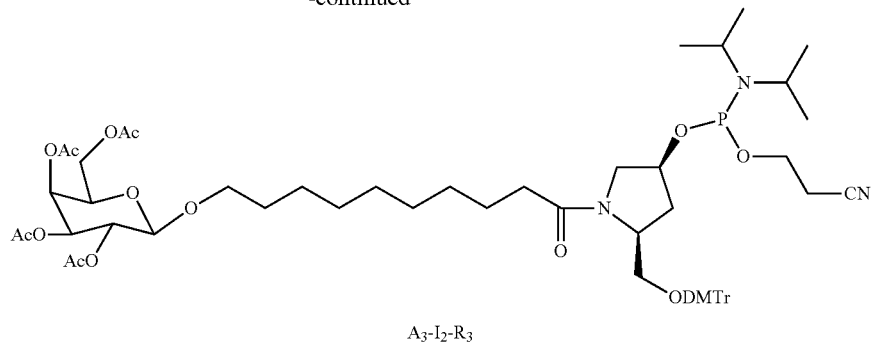

A₃-I₂-R₃

(1) Synthesis of Compound 33

The synthesis of compound 33 was with reference to the synthesis of compound 16 using compound A₃-I₂ as the raw material. A white solid was obtained with a yield of 83.8%. MS(ESI), m/z:942.4 ([M+Na]⁺).

(2) Synthesis of Compound A₃-I₂-R₃

The synthesis of compound A₃-I₂-R₃ was with reference to the synthesis of compound A₁-I₁-R₁ using compound 33 as the raw material. A white solid was obtained with a yield of 85.2%. ¹H NMR (400 MHz, DMSO-d6) δ:7.46-7.41 (d, J=7.2 Hz, 2H), 7.37-7.31 (t, J=6.9 Hz, 2H), 7.28-7.19 (m, 5H), 6.92-6.86 (d, J=8.2 Hz, 4H), 5.22 (s, 1H), 5.02-4.9 (m, 1H), 4.5-4.98 (s, J=3.5 Hz, 1H), 4.08-3.99 (m, 3H), 3.9-3.88 (m, 1H), 3.84-3.80 (m, 2H), 3.75 (s, 6H), 3.73-3.65 (m, 1H), 3.48-3.38 (m, 1H), 3.05-3.00 (m, 3H), 2.91-2.86 (m, 2H), 2.88-2.84 (m, 2H), 2.77-2.71 (m, 1H), 2.59-2.54 (m, 2H), 2.12 (s, 3H), 2.05-2.01 (m, 2H), 2.00 (s, 3H), 1.88 (s, 3H), 1.86-1.81 (m, 2H), 1.77 (s, 12H), 1.66 (s, 3H), 1.5-1.4 (m, 2H), 1.39-1.3 (m, 2H), 1.29-1.19 (m, 10H). MS(ESI), m/z: 1142.5 ([M+Na]⁺).

Example 29 Synthesis of Compound A₁-II₁-R₁

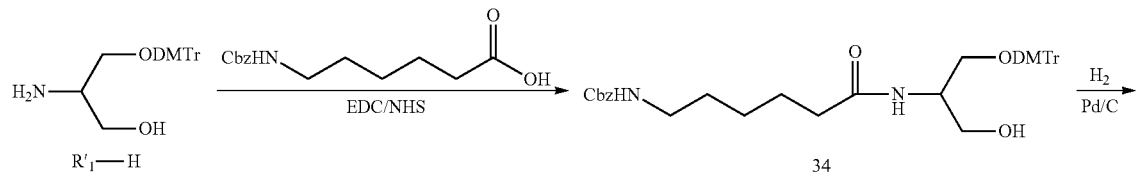

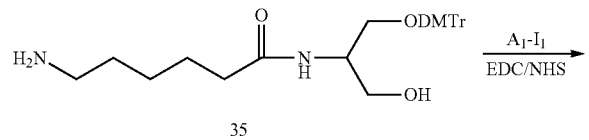

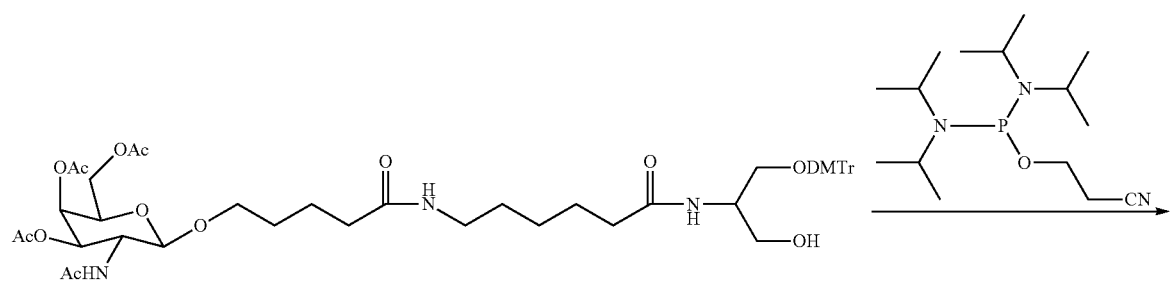

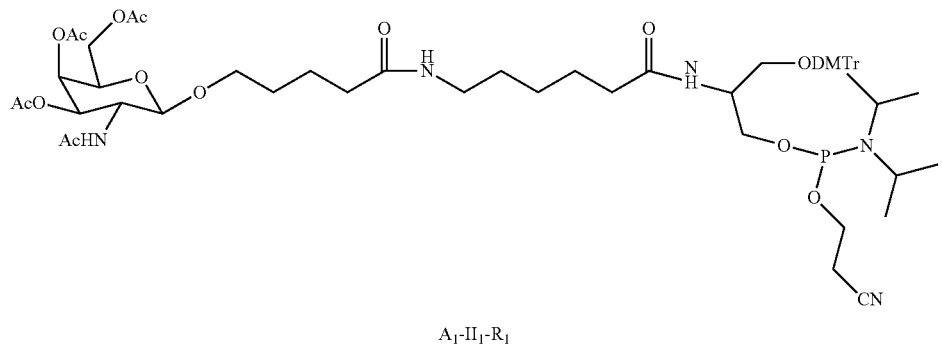

$A_1$-$II_1$-$R_1$ (1) Synthesis of Compound 34

In a 250 mL round bottom flask, N-benzyloxycarbonyl-6-aminocaproic acid (10 g, 37.69 mmol), 1-ethyl-(3-dimethylaminopropyl) carbonyldiimine hydrochloride (EDC.HCL) (8.67 g, 45.23 mmol), N-hydroxysuccinimide (4.67 g, 41.46 mmol), and dichloromethane 100 mL were added. After stirring for the reaction at room temperature for 0.5 hours, compound $R_1$-H (14.8 g, 37.69 mmol) was added, and the reaction was monitored by TLC and was complete after 4 h. The reaction liquid was washed with 50 mL of saturated sodium bicarbonate solution and 50 mL of saturated brine successively, the organic phase was dried over anhydrous sodium sulfate, then concentrated, and passed through a silica gel column (ethyl acetate:petroleum ether V:V=4:1) to isolate 19.8 g of a white solid with a yield of 82.1%. MS(ESI), m/z:663.1 ([M+Na]$^+$).

(2) Synthesis of Compound 35

In a 100 mL round bottom flask, compound 34 (5 g, 7.8 mmol), Pd/C (0.5 g, 10%) were dissolved in 10 mL of methanol and 4.0 mL of ethyl acetate, introduced with a hydrogen balloon for a reaction; the reaction was monitored by TLC and was complete after 6 h. The reaction solution was filtered through diatomite, and rinsed with diatomite methanol; and the filtrate was concentrated under reduced pressure and spin-dried to obtain 3.8 g of a white solid with a yield of 96.1%. $^1$HNMR (400 MHz, DMSO-d6) δ:7.64-7.61 (d, J=7.2 Hz, 1H), 7.43-7.37 (d, J=8.2 Hz, 2H), 7.33-7.28 (t, J=6.9 Hz, 2H), 7.27-7.19 (m, 5H), 6.92-6.87 (d, J=8.2 Hz, 4H), 5.12 (m, 2H), 4.63-4.58 (m, 1H), 4.05-3.97 (m, 1H), 3.73 (s, 6H), 3.5-3.42 (m, 2H), 3.04-2.99 (m, 2H), 2.95-2.90 (m, 2H), 2.12-2.06 (m, 2H), 1.52-1.45 (m, 2H), 1.42-1.35 (m, 2H), 1.28-1.20 (m, 2H). MS(ESI), m/z:529.3 ([M+Na]$^+$).

(3) Synthesis of Compound 36

In a 250 mL round bottom flask, compound $A_1$-$I_1$ (10 g, 22.37 mmol), 1-ethyl-(3-dimethylaminopropyl) carbonyldiimine hydrochloride (EDC. HCL) (5.15 g, 26.85 mmol), N-hydroxysuccinimide (2.83 g, 24.61 mmol) and dichloromethane 100 mL were added. After stirring for the reaction at room temperature for 0.5 hours, compound 35 (11.32 g, 22.37 mmol) was added, and the reaction was monitored by TLC and was complete after 6 h. The reaction liquid was washed successively with 50 mL of saturated sodium bicarbonate solution and 50 mL of saturated brine, the organic phase was dried over anhydrous sodium sulfate, then concentrated, and passed through a silica gel column (dichloromethane:methanol V:V=20:1) to isolate 17.3 g of a white solid with a yield of 82.7%. MS (ESI), m/z:958 ([M+Na]$^+$).

(4) Synthesis of $A_1$-$II_1$-$R_1$

The synthesis of compound $A_1$-$II_1$-$R_1$ was with reference to the synthesis of compound $A_1$-$I_1$-$R_1$ using compound 36 as the raw material. A white solid was obtained with a yield of 84.7%. $^1$HNMR (400 MHz, DMSO-d6) δ:7.84-7.80 (d, J=7.2 Hz, 1H), 7.72-7.66 (m, 1H), 7.64-7.61 (d, J=7.2 Hz, 1H), 7.43-7.37 (d, J=8.2 Hz, 2H), 7.33-7.28 (t, J=6.9 Hz, 2H), 7.27-7.19 (m, 5H), 6.92-6.87 (d, J=8.2 Hz, 4H), 5.20 (s, 1H), 5.0-4.95 (q, J=4.2 Hz, 1H), 4.51-4.46 (d, J=7.2 Hz, 1H), 4.15-4.11 (m, 3H), 4.05-3.97 (m, 1H), 3.89-3.79 (m, 3H), 3.76 (s, 6H), 3.74-3.69 (m, 1H), 3.54-3.49 (m, 2H), 3.46-3.36 (m, 1H), 3.04-2.99 (m, 2H), 2.95-2.90 (m, 2H), 2.88-2.84 (m, 2H), 2.59-2.54 (m, 2H), 2.22-2.14 (t, J=7.2 Hz, 2H), 2.15 (s, 3H), 2.12-2.06 (m, 2H), 2.00 (s, 3H), 1.95 (s, 3H), 1.87 (s, 3H), 1.77 (s, 12H), 1.59-1.42 (m, 6H), 1.41-1.35 (m, 2H), 1.28-1.20 (m, 2H). MS(ESI), m/z:1158.5 ([M+Na]$^+$).

Example 30 Synthesis of Compound $A_1$-$II_1$-$R_2$

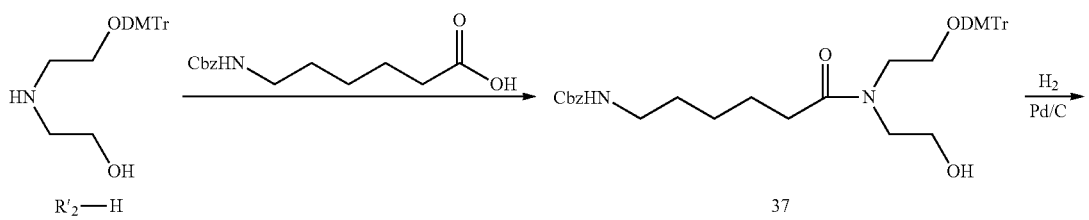

37

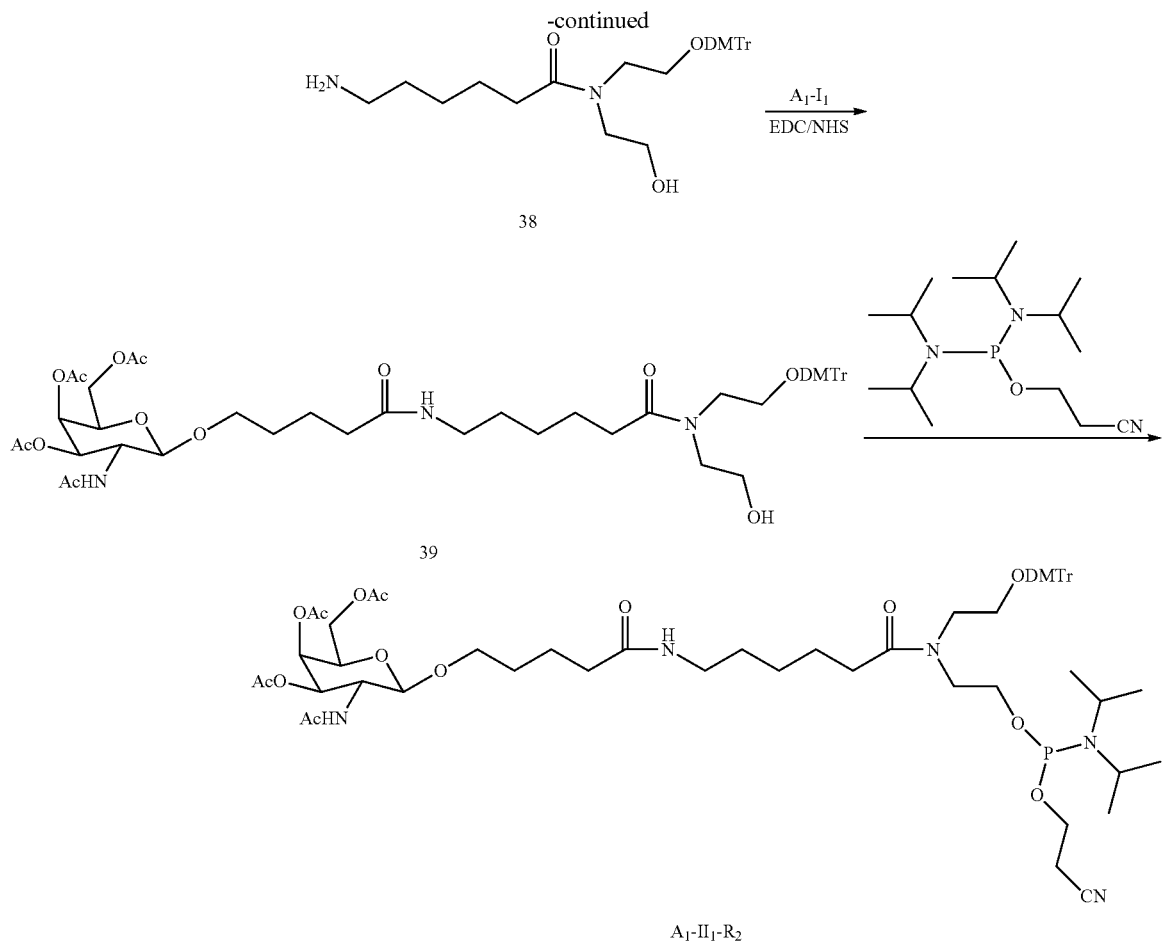

(1) Synthesis of Compound 37

The synthesis of compound 37 was with reference to the synthesis of compound 34 using compound R'$_2$-H as the raw material. A white solid was obtained with a yield of 84.3%. MS(ESI), m/z:677.5 ([M+Na]$^+$).

(2) Synthesis of Compound 38

The synthesis of compound 38 was with reference to the synthesis of compound 35 using compound 37 as the raw material. A white solid was obtained with a yield of 88.2%.

$^1$HNMR (400M Hz, DMSO-d6) δ:7.44-7.38 (d, J=8.2 Hz, 2H), 7.34-7.29 (t, J=6.9 Hz, 2H), 7.28-7.20 (m, 5H), 6.92-6.87 (d, J=8.2 Hz, 4H), 5.12 (m, 2H), 4.63-4.58 (m, 1H), 3.73 (s, 6H), 3.5-3.42 (m, 2H), 3.04-2.99 (m, 2H), 2.95-2.90 (m, 2H), 2.88-2.82 (m, 4H), 2.12-2.06 (m, 2H), 1.52-1.45 (m, 2H), 1.42-1.35 (m, 2H), 1.28-1.20 (m, 2H). MS(ESI), m/z:543.3 ([M+Na]$^+$).

(3) Synthesis of Compound 39

The synthesis of compound 39 was with reference to the synthesis of compound 36 using compound 38 as the raw material. A white solid was obtained with a yield of 80.7%. MS(ESI), m/z:972.6 ([M+Na]$^+$).

(4) Synthesis of Compound $A_1$-II$_1$-R$_2$

The synthesis of compound $A_1$-II$_1$-R$_2$ was with reference to the synthesis of compound $A_1$-I$_1$-R$_1$ using compound 39 as the raw material. A white solid was obtained with a yield of 84.1%. $^1$HNMR (400 MHz, DMSO-d6) δ:7.83-7.79 (d, J=7.2 Hz, 1H), 7.72-7.66 (m, 1H), 7.42-7.36 (d, J=8.2 Hz, 2H), 7.33-7.28 (t, J=6.9 Hz, 2H), 7.27-7.19 (m, 5H), 6.92-6.87 (d, J=8.2 Hz, 4H), 5.20 (s, 1H), 5.0-4.95 (q, J=4.2 Hz, 1H), 4.51-4.46 (d, J=7.2 Hz, 1H), 4.15-4.10 (m, 3H), 3.89-3.79 (m, 3H), 3.76 (s, 6H), 3.74-3.69 (m, 1H), 3.54-3.49 (m, 2H), 3.46-3.36 (m, 1H), 3.04-2.99 (m, 2H), 2.95-2.90 (m, 2H), 2.88-2.84 (m, 6H), 2.59-2.54 (m, 2H), 2.22-2.14 (t, J=7.2 Hz, 2H), 2.15 (s, 3H), 2.12-2.06 (m, 2H), 2.00 (s, 3H), 1.95 (s, 3H), 1.87 (s, 3H), 1.77 (s, 12H), 1.59-1.42 (m, 6H) 1.41-1.35 (m, 2H), 1.28-1.20 (m, 2H). MS(ESI), m/z:1172.7 ([M+Na]$^+$).

Example 31 Synthesis of Compound $A_1$-III$_1$-R$_1$

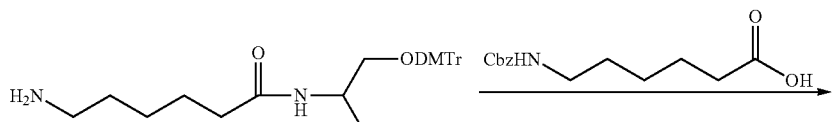

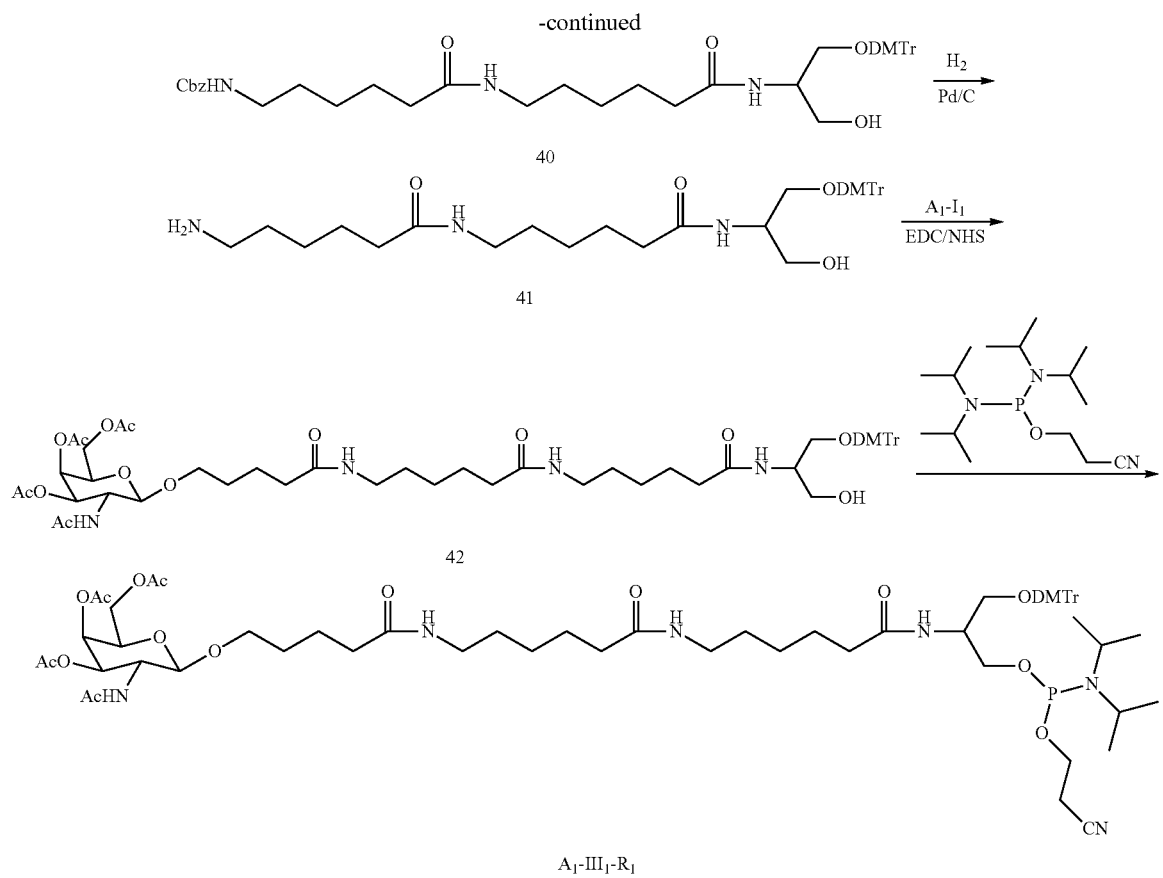

(1) Synthesis of Compound 40

The synthesis of compound 40 was with reference to the synthesis of compound 34 using compound 35 as the raw material. A white solid was obtained with a yield of 82.6%. MS(ESI), m/z:776.7 ([M+Na]$^+$).

(2) Synthesis of Compound 41

The synthesis of compound 41 was with reference to the synthesis of compound 35 using compound 40 as the raw material. A white solid was obtained with a yield of 96.7%.

$^1$HNMR (400 MHz, DMSO-d6) δ:7.71-7.67 (m, 1H), 7.65-7.62 (d, J=7.2 Hz, 1H), 7.45-7.39 (d, J=8.2 Hz, 2H), 7.34-7.29 (t, J=6.9 Hz, 2H), 7.26-7.19 (m, 5H), 6.93-6.88 (d, J=8.2 Hz, 4H), 5.14 (m, 2H), 4.64-4.58 (m, 1H), 4.05-3.98 (m, 1H), 3.72 (s, 6H), 3.5-3.43 (m, 4H), 3.05-2.99 (m, 2H), 2.95-2.90 (m, 2H), 2.12-2.06 (m, 4H), 1.52-1.45 (m, 4H), 1.41-1.35 (m, 4H), 1.29-1.20 (m, 4H). MS(ESI), m/z:642.3 ([M+Na]$^+$).

(3) Synthesis of Compound 42

The synthesis of compound 42 was with reference to the synthesis of compound 36 using compound 41 as the raw material. A white solid was obtained with a yield of 86.3%. MS(ESI), m/z: 1071.4 ([M+Na]$^+$).

(4) Synthesis of Compound $A_1$-$III_1$-$R_1$

The synthesis of compound $A_1$-$III_1$-$R_1$ was with reference to the synthesis of compound $A_1$-$I_1$-$R_1$ using compound 42 as the raw material. A white solid was obtained with a yield of 84.1%. $^1$HNMR (400 MHz, DMSO-d6) δ:7.85-7.81 (d, J=7.2 Hz, 1H), 7.78-7.74 (m, 1H), 7.72-7.66 (m, 1H), 7.65-7.61 (d, J=7.2 Hz, 1H), 7.42-7.38 (d, J=8.2 Hz, 2H), 7.34-7.29 (t, J=6.9 Hz, 2H), 7.27-7.18 (m, 5H), 6.93-6.87 (d, J=8.2 Hz, 4H), 5.22 (s, 1H), 5.0-4.96 (q, J=4.2 Hz, 1H), 4.51-4.46 (d, J=7.2 Hz, 1H), 4.15-4.11 (m, 3H), 4.05-3.97 (m, 1H), 3.89-3.79 (m, 3H), 3.76 (s, 6H), 3.74-3.69 (m, 1H), 3.54-3.49 (m, 4H), 3.46-3.36 (m, 1H), 3.04-2.99 (m, 2H), 2.95-2.90 (m, 2H), 2.88-2.84 (m, 2H), 2.59-2.54 (m, 2H), 2.22-2.14 (t, J=7.2 Hz, 2H), 2.15 (s, 3H), 2.12-2.06 (m, 4H), 2.00 (s, 3H), 1.95 (s, 3H), 1.87 (s, 3H), 1.77 (s, 12H), 1.59-1.42 (m, 8H) 1.41-1.35 (m, 4H), 1.28-1.20 (m, 4H). MS(ESI), m/z:1271.2 ([M+Na]$^+$).

Example 32 Synthesis of Compound $A_1$-$IV_1$-$R_1$

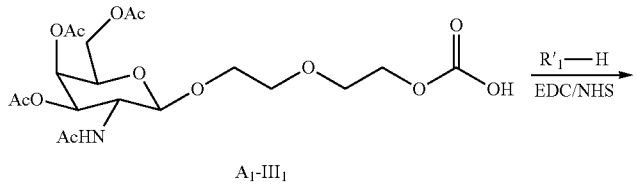

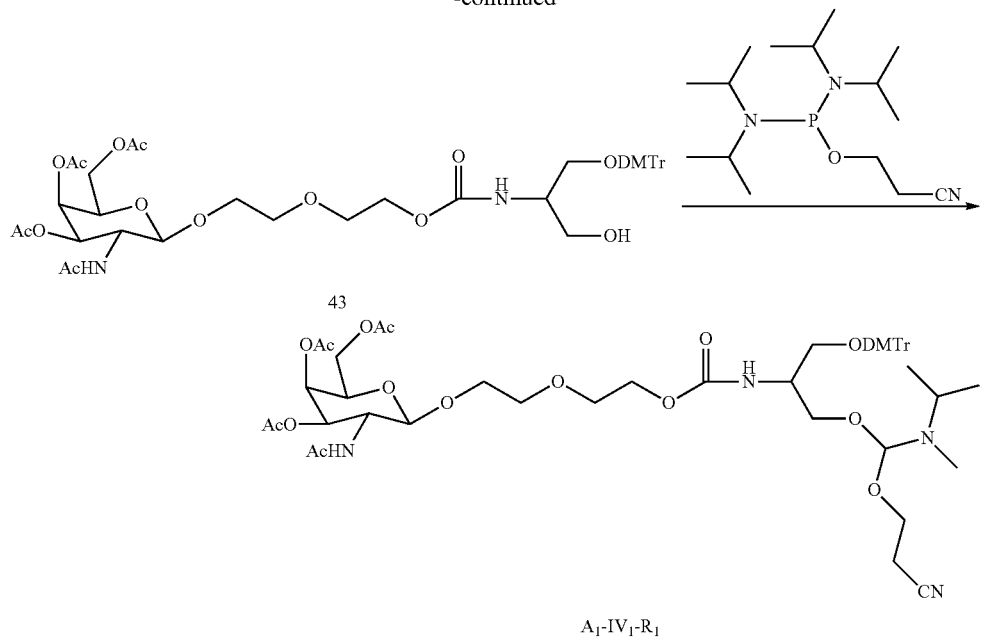

A₁-IV₁-R₁

(1) Synthesis of Compound 43

The synthesis of compound 43 was with reference to the synthesis of compound 16 using compound A₁-III₁ as the raw material. A white solid was obtained with a yield of 82.8%. MS(ESI), m/z:877.4 ([M+Na]⁺).

(2) Synthesis of Compound A₁-III₁-R₁

The synthesis of compound A₁-III₁-R₁ was with reference to the synthesis of compound A₁-I₁-R₁ using compound 40 as the raw material. The yield is 82.9%. ¹HNMR (400 MHz, DMSO-d6) δ:7.76-7.72 (d, J=8.9 Hz, 1H), 7.70-7.66 (d, J=8.0 Hz, 1H), 7.40-7.36 (d, J=7.2 Hz, 2H), 7.32-7.28 (t, J=6.9 Hz, 2H), 7.27-7.19 (m, 5H), 6.91-6.86 (d, J=8.2 Hz, 4H), 5.21 (s, 1H), 5.0-4.96 (q, J=4.2 Hz, 1H), 4.45-4.51 (d, J=7.2 Hz, 1H), 4.12-4.07 (m, 3H), 4.05-3.97 (m, 1H), 3.88-3.78 (m, 3H), 3.74 (s, 6H), 3.72-3.68 (m, 2H), 3.62-3.58 (m, 2H), 3.56-3.46 (m, 4H), 3.04-2.99 (m, 2H), 2.95-2.90 (m, 2H), 2.89-2.85 (m, 2H), 2.58-2.53 (m, 2H), 2.15 (s, 3H), 2.00 (s, 3H), 1.95 (s, 3H), 1.88 (s, 3H), 1.76 (s, 12H). MS(ESI), m/z:1077.3 ([M+Na]⁺).

Example 33 Synthesis of Compound A₁-V₁-R₄

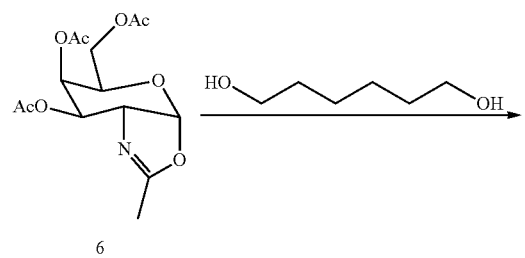

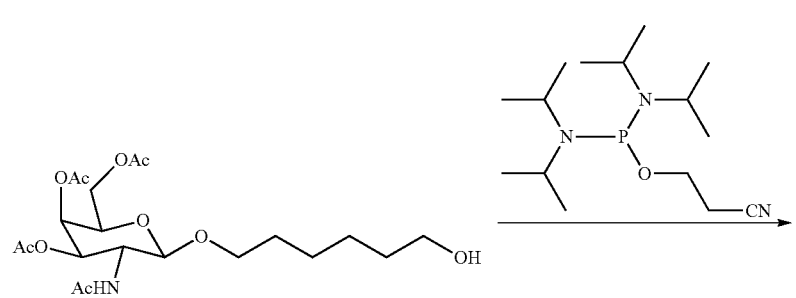

-continued

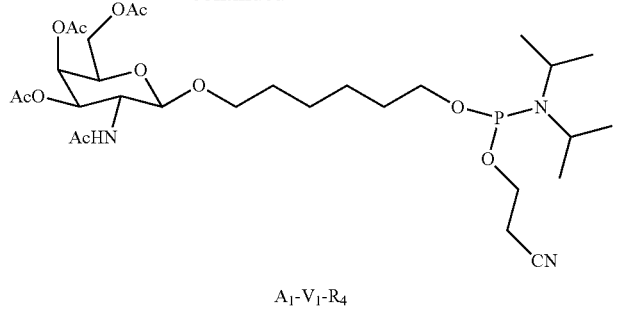

$A_1$-$V_1$-$R_4$ (1) Synthesis of Compound 44

In a 250 mL round bottom flask, compound 6 (5 g, 15.2 mmol) and 1,6-hexanediol (9 g, 76 mmol) were dissolved in 100 mL of anhydrous 1,2-dichloroethane, stirred for 30 min, and added with trimethylsilyl trifluoromethanesulfonate (0.55 mL, 3 mmol); the reaction was reacted overnight at room temperature; the reaction solution was extracted with dichloromethane, and the organic phase was washed twice with 80 mL of saturated sodium bicarbonate solution, dried over anhydrous sodium sulfate, concentrated under reduced pressure, and passed through a silica gel column (petroleum ether:ethyl acetate V:V=3:2) to isolate 5.86 g of a clear oily liquid with a yield of 86.2%. MS(ESI), m/z:470.2 ([M+Na]$^+$).

(2) Synthesis of Compound $A_1$-$V_1$-$R_4$

The synthesis of compound $A_1$-$V_1$-$R_4$ was with reference to the synthesis of compound $A_1$-$I_1$-$R_1$ using compound 41 as the raw material. The yield is 84.1%. $^1$HNMR (400 MHz, DMSO-d6) δ:7.80-7.75 (d, J=8.9 Hz, 1H), 5.21 (s, 1H), 5.02-4.95 (q, J=4.2 Hz, 1H), 4.50-4.76 (d, J=7.2 Hz, 1H), 4.12-4.07 (m, 3H), 3.88-3.79 (m, 3H), 3.80-3.69 (m, 2H), 3.46-3.36 (m, 2H), 2.88-2.84 (m, 2H), 2.59-2.54 (m, 2H), 2.23-2.28 (m, 2H), 2.22-2.14 (m, 2H), 2.15 (s, 3H), 2.00 (s, 3H), 1.95 (s, 3H), 1.87 (s, 3H), 1.79 (s, 12H), 1.58-1.42 (m, 4H). MS(ESI), m/z:870.5 ([M+Na]$^+$).

Example 34 Preparation of Modified Single Stranded Oligonucleotides

In this embodiment, the modified oligonucleotide was synthesized according to the theoretical yield of 1 µmol. The process was as follows:

(1) In anhydrous acetonitrile, the weighed 1 µmol of standard universal solid support CPG or 3'-cholesterol modified CPG (purchased from Chemgenes), 2'-O-TBDMS-protected RNA phosphoramidite monomer, DNA monomer, 2'-methoxy monomer and 2'-fluoro monomer (purchased from Sigma Aldrich) were dissolved to a concentration of 0.2 M. For phosphorothioate backbone modified oligonucleotides, a 0.2 M PADS solution was used as the thionating reagent. A solution of 5-ethylthio-1H-tetrazole (purchased from Chemgenes) in acetonitrile as the activator (0.25 M), a 0.02 M solution of iodine in pyridine/water as the oxidant, and a 3% solution of trichloroacetic acid in dichloromethane as the deprotecting reagent were placed at the designated position of the reagent corresponding to the ABI 394 DNA/RNA automatic synthesizer.

(2) A synthesis procedure was set, a specified oligonucleotide base sequence was input and checked to make sure there was no errors, and cyclic oligonucleotide synthesis was started, wherein the coupling time of each step is 6 minutes, and the coupling time of the galactose ligand corresponding monomer ($A_x$-linker-$R_x$ compound) is 10-20 minutes. After automatic circulation, oligonucleotide solid-phase synthesis was completed.

(3) The CPG was blown dry with dry nitrogen, transferred to a 5 mL EP tube, added with 2 mL of ammonia/ethanol solution (3/1) and heated at 55° C. for 16-18 hours. Centrifugation was carried out at 10,000 rpm for 10 min, the supernatant was taken and concentrated aqueous ammonia/ethanol was pumped to dryness to obtain a white gummy solid. The solid was dissolved in 200 µl of 1 M TBAF in THF and shaken at room temperature for 20 hours. 0.5 mL of 1 M Tris-HCl buffer (pH 7.4) was added, shaken for 15 minutes at room temperature and placed on a centrifugal pump to a volume of ½ of the original volume to remove THF. The solution was extracted twice with 0.5 mL of chloroform, 0.1 mL of 0.1 M TEAA loading solution was added, the mixed solution was poured into a solid phase extraction column, and excess salt in the solution was removed.

(4) The concentration of the obtained oligonucleotide was measured by micro-UV spectrophotometer (K05500). The mass spectrometric analysis was performed on an Oligo HTCS LC-MS system (Novatia) system. Nucleic acid molecular weight was calculated by normalization with Promass software after primary scanning.

Example 35 Preparation of Modified Single Stranded Oligonucleotides

In this embodiment, the modified oligonucleotide was synthesized according to the theoretical yield of 1 µmol. The process was as follows:

(1) In anhydrous acetonitrile, the weighed 1 µmol of standard universal solid support CPG or 3'-cholesterol modified CPG (purchased from Chemgenes), DNA monomer, 2'-methoxy monomer and 2'-fluoro monomer (purchased from Sigma Aldrich) were dissolved to a concentration of 0.2 M. For phosphorothioate backbone modified oligonucleotides, a 0.2 M PADS solution was used as the thionating reagent. A solution of 5-ethylthio-1H-tetrazole (purchased from Chemgenes) in acetonitrile as the activator (0.25 M), a 0.02 M solution of iodine in pyridine/water as the oxidant, and a 3% solution of trichloroacetic acid in dichloromethane as the deprotecting reagent were placed at the designated position of the reagent corresponding to the ABI 394 DNA/RNA automatic synthesizer.

(2) A synthesis procedure was set, a specified oligonucleotide base sequence was input and checked to make sure there was no errors, and cyclic oligonucleotide synthesis was started, wherein the coupling time of each step is 6 minutes, and the coupling time of the galactose ligand corresponding monomer ($A_x$-linker-$R_x$ compound) is 6-10 minutes. After automatic circulation, oligonucleotide solid-phase synthesis was completed.

(3) The CPG was blown dry with dry nitrogen, transferred to a 5 mL EP tube, added with 2 ml of aqueous ammonia solution, and heated at 55° C. for 16-18 hours. Centrifugation was carried out at 10,000 rpm for 10 min, the supernatant was taken and concentrated aqueous ammonia/ethanol was pumped to dryness to obtain a white or yellow gummy solid. Followed by adding 1 mL of 0.1 M TEAA loading solution, the mixed solution was poured onto a solid phase extraction column to remove excess salt from the solution.

(4) The concentration of the obtained oligonucleotide was measured by micro-UV spectrophotometer (K05500). The mass spectrometric analysis was performed on an Oligo HTCS LC-MS system (Novatia) system. Nucleic acid molecular weight were calculated by normalization with Promass software after primary scanning.

Example 36 Preparation of Modified Double Stranded Oligonucleotides

The process was as follows: after the preparation of the modified single-stranded oligonucleotides were completed, the modified single-stranded oligonucleotides were mixed according to an ultraviolet absorption content of 1:1, heated to 95° C. for three minutes, and then cooled to room temperature to form double strands.

In Examples 34-36, the modified oligonucleotides with a crude purity of less than 50% were purified in a linear gradient manner by a DNAPAc PA-100 ion exchange column with mobile phase A: 20 mM NaOH; and mobile phase B: 20 mM NaOH+2M NaCl mixture.

Exemplary modified oligonucleotide sequences and corresponding molecular weight detection results are shown in Table 1.

Abbreviations Description: N=RNA; dN=DNA; mN=2' OMe modification; fN=2'F modification.

TABLE 1

| No. | Structure (5'-3') | Theoretical MW | Observed MW |
|---|---|---|---|
| P8G8-A1 | mCmAdGfCdAmAdGfUdGfUdGmAfCmAmGfUfCmAmU-$(A_1-I_1-R_1)_1$ | 6585.1 | 6585.4 |
| | AfUGAfCfUGfUfCAfCAfCfUfUGfCfUGGfCfCfUGfU | 7941.6 | 7941.0 |
| P8G8-A2 | mCmAdGfCdAmAdGfUdGfUdGmAfCmAmGfUfCmAmU-$(A_1-I_1-R_1)_2$ | 7041.2 | 7042.1 |
| | AfUGAfCfUGfUfCAfCAfCfUfUGfCfUGGfCfCfUGfU | 7941.6 | 7941.9 |
| P8G8-A3 | mCmAdGfCdAmAdGfUdGfUdGmAfCmAmGfUfCmAmU-$(A_1-I_1-R_1)_3$ | 7497.4 | 7496.4 |
| | AfUGAfCfUGfUfCAfCAfCfUfUGfCfUGGfCfCfUGfU | 7941.6 | 7941.2 |
| P8G8-A4 | mCmAdGfCdAmAdGfUdGfUdGmAfCmAmGfUfCmAmU-$(A_1-I_1-R_1)_4$ | 7953.5 | 7954.6 |
| | AfUGAfCfUGfUfCAfCAfCfUfUGfCfUGGfCfCfUGfU | 7941.6 | 7942.3 |
| A3-P8G8 | $(A_1-I_1-{}_1R_1)_3$-mCmAdGfCdAmAdGfUdGfUdGmAfCmAmGfUfCmAmU | 7497.4 | 7497.8 |
| | AfUGAfCfUGfUfCAfCAfCfUfUGfCfUGGfCfCfUGfU | 7941 6 | 7942.7 |
| P8G8-B1 | mCmAdGfCdAmAdGfUdGfUdGmAfCmAmGfUfCmAmU-$(A_1-I_2-R_1)_1$ | 6655.1 | 6653.2 |
| | AfUGAfCfUGfUfCAfCAfCfUfUGfCfUGGfCfCfUGfU | 7941.6 | 7940.3 |
| P8G8-B2 | mCmAdGfCdAmAdGfUdGfUdGmAfCmAmGfUfCmAmU-$(A_1-I_2-R_1)_2$ | 7181.4 | 7182.0 |
| | AfUGAfCfUGfUfCAfCAfCfUfUGfCfUGGfCfCfUGfU | 7941.6 | 7942.5 |
| P8G8-B3 | mCmAdGfCdAmAdGfUdGfUdGmAfCmAmGfUfCmAmU-$(A_1-I_2-R_1)_3$ | 7707.6 | 7709.4 |
| | AfUGAfCfUGfUfCAfCAfCfUfUGfCfUGGfCfCfUGfU | 7941.6 | 7940.6 |
| P8G8-B4 | mCmAdGfCdAmAdGfUdGfUdGmAfCmAmGfUfCmAmU-$(A_1-I_2-R_1)_4$ | 8233.8 | 8234.6 |
| | AfUGAfCfUGfUfCAfCAfCfUfUGfCfUGGfCfCfUGfU | 7941.6 | 7942.7 |
| B3-P8G8 | $(A_1-I_2-R_1)_3$-mCmAdGfCdAmAdGfUdGfUdGmAfCmAmGfUfCmAmU | 7707.6 | 7709.3 |
| | AfUGAfCfUGfUfCAfCAfCfUfUGfCfUGGfCfCfUGfU | 7941.6 | 7942.2 |
| P8G8-C3 | mCmAdGfCdAmAdGfUdGfUdGmAfCmAmGfUfCmAmU-$(A_1-II_1-R_1)_2$ | 7836.6 | 7835.1 |
| | AfUGAfCfUGfUfCAfCAfCfUfUGfCfUGGfCfCfUGfU | 7941.6 | 7942.5 |
| P8G8-D3 | mCmAdGfCdAmAdGfUdGfUdGmAfCmAmGfUfCmAmU-$(A_1-III_1-R_1)_3$ | 8175.9 | 8177.3 |
| | AfUGAfCfUGfUfCAfCAfCfUfUGfCfUGGfCfCfUGfU | 7941.3 | 7940.2 |
| P8G8-E3 | mCmAdGfCdAmAdGfUdGfUdGmAfCmAmGfUfCmAmU-$(A_1-I_1-R_2)_3$ | 7539.4 | 7538.1 |
| | AfUGAfCfUGfUfCAfCAfCfUfUGfCfUGGfCfCfUGfU | 7941.6 | 7942.7 |
| P8G8-F3 | mCmAdGfCdAmAdGfUdGfUdGmAfCmAmGfUfCmAmU-$(A_2-I_2-R_1)_3$ | 8070.7 | 8068.9 |
| | AfUGAfCfUGfUfCAfCAfCfUfUGfCfUGGfCfCfUGfU | 7941.6 | 7940.1 |
| P8G8-G3 | mCmAdGfCdAmAdGfUdGfUdGmAfCmAmGfUfCmAmU-$(A_3-I_2-R_1)_3$ | 7584.5 | 7583.7 |
| | AfUGAfCfUGfUfCAfCAfCfUfUGfCfUGGfCfCfUGfU | 7941.6 | 7941.2 |
| P8G8-H2I | $(A_1-V_1-R_4)-(A_1-IV_1-R_1)_2$-mCmAdGfCdAmAdGfUdGfUdGm AfCmAmGfUfCmAmU | 7488.3 | 7386.5 |
| | AfUGAfCfUGfUfCAfCAfCfUfUGfCfUGGfCfCfUGfU | 7941.6 | 7939.7 |
| P9G20-A3 | CAGGCCAGCAAGUGUGACA-$(A_1-I_1-R_1)_3$ | 7491.3 | 7492.0 |
| | fUmGfUfCfA(s)dC(s)dAmCmUfUfGfC(s)dT(s)dGmGmCfCfUfG(s)mU(s)mC | 6766.4 | 6766.9 |

The modified sequences (not including the compound of modifier, such as $A_1$-$I_1$-$R_1$) of Table 1 are as followings:

Sequence 5 (SEQ ID NO: 5):
mCmAdGfCdAmAdGfUdGfUdGmAfCmAmGfUfCmAmU

Sequence 6 (SEQ ID NO: 6):
AfUGAfCfUGfUfCAfCAfCfUfUGfCfUGGfCfCfUGfU

Sequence 7 (SEQ ID NO: 7):
fUmGfUfCfA(s)dC(s)dAmCmUfUfGfC(s)dT(s)dGmGmCfCfUfG(s)mU(s)mC

Example 37 Cell Targeting Assay of Modified Oligonucleotides

Modified oligonucleotides for animal experiments were filtered through a 0.22 μm membrane before injection.

1, Isolation of Primary Mouse Hepatocytes

The mice were anesthetized, and the skin and muscle layers were dissected to expose the liver, the perfusion catheter was inserted into the portal vein, and the inferior vena cava was dissected to prepare for liver perfusion. Perfusion Solution I (Hank's, 0.5 mM EGTA, pH 8) and Perfusion Solution II (Low-glucose DMEM, 100 U/mL Type IV, pH 7.4) were pre-warmed at 40° C., and Perfusion Solution I of 37° C. was perfused through the portal vein at a flow rate of 7 mL/min for 5 min until the liver turned off-white. Perfusion Solution II of 37° C. was then perfused into the liver at a flow rate of 7 mL/min for 7 min. After perfusion was complete, the liver was removed and placed in Solution III (10% FBS low-glucose DMEM, 4° C.) to stop digestion, then the liver capsule was cut by the forceps, and the hepatocytes was released by gently shaking. The hepatocytes were filtered through a 70 μm cell filter, centrifuged at 50 g for 2 min with the supernatant discarded. The cells were resuspended in Solution IV (40% percoll low-glucose DMEM, 4° C.), centrifuged at 100 g for 2 min with the supernatant discarded. Cells were added with 2% FBS low-glucose DMEM and resuspended for use. Cell viability was identified by Trypan blue staining.

2, Determinations of GalNAc Binding Curves and Kd Values

Freshly isolated mouse primary hepatocytes were plated in 96-well plates at 2×10⁴ cells/well, 100 μl/well. GalNAc-siRNA was added to each well, respectively. Each GalNAc-siRNA was set to a final concentration of 0.9 nM, 2.7 nM, 8.3 nM, 25 nM, 50 nM, or 100 nM. The suspensions were incubated at 4° C. for 2 h, and centrifuged at 50 g for 2 min with the supernatant discarded. The cells were resuspended in 10 μg/ml PI, stained for 10 min and centrifuged at 50 g for 2 min. Cells were washed with pre-cooled PBS and centrifuged at 50 g for 2 min with the supernatant discarded. The cells were resuspended in PBS. The mean fluorescence intensity (MFI) of living cells was measured by a flow cytometry, and nonlinear fitting and $K_d$ value calculation were performed with the GraphPad Prism 5 software. The results are shown in Table 2, Table 3 and FIG. 1. The data showed that GalNAc-siRNA could specifically target hepatocytes; the GalNAc ligand has a Kd value of 7.6-53.4 nM with the cell receptor, showing a higher affinity (Ki value 5.2-51.3 nM) compared with the galactose ligand preferred in the prior art (PCT/US2014/046425). GalNAc-siRNAs with different conjugate structures show a certain difference in binding ability to the receptor, and structures A3 and A4 show a relatively strong affinity for the receptor (the smaller the Kd value, the greater the affinity).

TABLE 2

$K_d$ values (nM) and $B_{max}$ values for each experimental group

| Groups | P8G8-A2 | P8G8-A3 | P8G8A4 | A3-P8G8 | P8G8-B2 | P8G8-B3 | P8G8-B4 | B3-P8G8 |
|---|---|---|---|---|---|---|---|---|
| $B_{max}$ | 101482 | 159404 | 156210 | 159880 | 96906 | 157659 | 167084 | 182089 |
| $K_d$ | 53.69 | 7.58 | 7.22 | 9.82 | 30.07 | 14.45 | 9.02 | 14.27 |

TABLE 3

$K_d$ values (nM) and $B_{max}$ values for each experimental group

| Groups | P8G8-C3 | P8G8-D3 | P8G8-E3 | P8G8-F3 | P8G8-G3 | P8G8-H2I | P9G20-A3 |
|---|---|---|---|---|---|---|---|
| $B_{max}$ | 197556 | 163439 | 169699 | 164021 | 176761 | 138114 | 170152 |
| $K_d$ | 12.26 | 17.56 | 14.90 | 18.54 | 17.87 | 8.89 | 9.87 |

Example 38 In Vivo Liver Targeting Assay

13 Male, 6-7 week old SPF grade Balb/c-nu mice (purchased from Beijing Vital River Laboratory Animal Technology Co., Ltd.) were used for this study, and were randomly divided into 4 groups, blank control group, P8G8 control group (unconjugated ligand), P8G8-A3 group and P8G8-B3 group. The number of animals in each group was 2, 3, 4 and 4 respectively, and administered by tail vein injection at a dose of about 10 mg/kg (see Table 4 for experimental design). All animals were subjected to in vivo imaging, including white light and X-ray imaging, before administration and 5 min, 30 min, 1 hour, 2 hours, 4 hours, 6 hours after administration. After euthanasia 6 hours after the administration, the brain, salivary glands, heart, spleen, lung, liver, kidney, and intestinal tract were removed for imaging of isolated organs.

TABLE 4

Liver targeting experimental design

| Sequence Number | Groupings | Samples for test | Dosing (mg/kg) | Dosing Volume (mL) |
|---|---|---|---|---|
| 1 | Blank control group | Saline | 0 | 0.2 |
| 2 | NC1 | P8G8 | 10 | 0.2 |

TABLE 4-continued

Liver targeting experimental design

| Sequence Number | Groupings | Samples for test | Dosing (mg/kg) | Dosing Volume (mL) |
|---|---|---|---|---|
| 3 | Positive group | P8G8-A3 | 10 | 0.2 |
| 4 | Positive group | P8G8-B3 | 10 | 0.2 |

The in vivo imaging analysis (Tables 5-6) showed that the fluorescence intensity of each liver in the P8G8-A3 and P8G8-B3 groups was higher than that in the negative control group 6 hours after administration. The results showed that P8G8-A3 and P8G8-B3 have a certain targeting to liver.

TABLE 5

Statistical results of in vivo organ fluorescence intensity values after background subtraction ($\times 10^8$ ps/mm$^2$)

| Groups | | Salivary gland | Liver | Kidney | Intestinal tract |
|---|---|---|---|---|---|
| P8G8 | Mean | 8102 | 4627 | 35414 | 15620 |
| | SD | 754 | 452 | 2685 | 1125 |
| P8G8-A3 | Mean | 8520 | 16214 | 39654 | 18564 |
| | SD | 962 | 1025 | 345 | 1265 |
| P8G8-B3 | Mean | 8954 | 13326 | 32584 | 19854 |
| | SD | 1203 | 1657 | 2147 | 2365 |

TABLE 6

Fluorescence intensity ratio results

| | Salivary gland | Liver | Kidney | Intestinal tract |
|---|---|---|---|---|
| P8G8-A3/P8G8 | 1.05 | 3.50 | 1.12 | 1.19 |
| P8G8-B3/P8G8 | 1.10 | 2.88 | 0.92 | 1.30 |

Although specific embodiments of the present disclosure have been described in detail, those skilled in the art will appreciate that various modifications and variations of the details are possible in light of the above teachings and are within the purview of this disclosure. The full scope of the present disclosure is indicated by the appended claims and any equivalents thereof.

What is claimed is:

1. A compound comprising an oligonucleotide and a conjugate group, wherein the modified oligonucleotide has a general formula

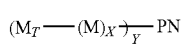

wherein PN is the oligonucleotide, Y is 1, X is 2, $M_T$ is selected from the conjugate group as shown in formulas (4),

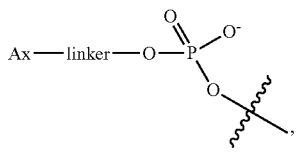

wherein in formulas (4), $A_x$ is $A_1'$, and the structure of the linker is shown in formula (v):

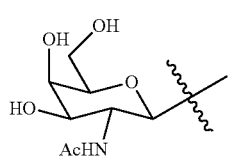

$A_1'$

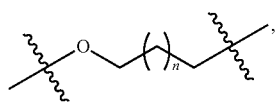

(v)

wherein n is selected from an integer between 1-10;
X is 2, the structure of the two M are the same as shown in formula (1'),

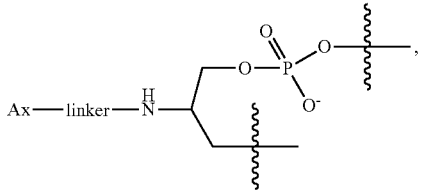

wherein in formula (1'), $A_x$ is the $A_1'$ and the structure of the linker is shown in formula (iv),

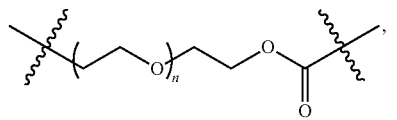

n is 1.

2. A kit comprising the compound as claimed in claim 1.

3. A pharmaceutical composition comprising the modified oligonucleotide as claimed in claim 1, and optionally a pharmaceutically acceptable carrier.

* * * * *

```
                          SEQUENCE LISTING

<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(19)
<223> OTHER INFORMATION: siRNA

<400> SEQUENCE: 1
cagcaagugu gacagucau                                                  19

<210> SEQ ID NO 2
<211> LENGTH: 25
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(25)
<223> OTHER INFORMATION: siRNA

<400> SEQUENCE: 2
augacuguca cacuugcugg ccugu                                           25

<210> SEQ ID NO 3
<211> LENGTH: 19
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(19)
<223> OTHER INFORMATION: siRNA
```

```
<400> SEQUENCE: 3
caggccagca agugugaca                                                    19

<210> SEQ ID NO 4
<211> LENGTH: 21
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(21)
<223> OTHER INFORMATION: siRNA

<400> SEQUENCE: 4
ugucacacuu gctggccugu c                                                 21

<210> SEQ ID NO 5
<211> LENGTH: 19
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(19)
<223> OTHER INFORMATION: Residues at 1, 2, 6, 12,14,15,18 and 19 are 2'
      OMe modification.
<220> FEATURE:
<221> NAME/KEY: misc_feature
<222> LOCATION: (1)..(19)
<223> OTHER INFORMATION: Residues  at  3, 5, 7,9 and 11 are DNA.
<220> FEATURE:
<221> NAME/KEY: misc_feature
<222> LOCATION: (1)..(19)
<223> OTHER INFORMATION: Residues  at  4, 8, 10 , 13, 16 and 17 are 2'F
      modification.

<400> SEQUENCE: 5
cagcaagugu gacagucau                                                    19

<210> SEQ ID NO 6
<211> LENGTH: 25
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(25)
<223> OTHER INFORMATION: Residues at 2, 5, 6, 8-9, 11, 13-15, 17-18,
      21-23 and 25 are 2' Fmodification.

<400> SEQUENCE: 6
augacuguca cacuugcugg ccugu                                             25

<210> SEQ ID NO 7
<211> LENGTH: 21
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: misc_feature
<222> LOCATION: (1)..(21)
<223> OTHER INFORMATION: Residues at 1, 3-5, 10-12 and 17-19 are 2'F
      modification.
```

```
<220> FEATURE:
<221> NAME/KEY: misc_feature
<222> LOCATION: (1)..(21)
<223> OTHER INFORMATION: Residues at 2, 8-9, 15-16 and 20-21 are 2'OMe
      modification.
<220> FEATURE:
<221> NAME/KEY: misc_feature
<222> LOCATION: (1)..(21)
<223> OTHER INFORMATION: Residues at 6-7 and 13-14 are DNA.
<220> FEATURE:
<221> NAME/KEY: misc_feature
<222> LOCATION: (1)..(21)
<223> OTHER INFORMATION: Residues at 6-7, 13-14, and 20-21 are
      phosphorthioate modification.

<400> SEQUENCE: 7
ugucacacuu gctggccugu c                                            21
```